US012196760B2

(12) United States Patent
Marcotte et al.

(10) Patent No.: US 12,196,760 B2
(45) Date of Patent: Jan. 14, 2025

(54) MOLECULAR NEIGHBORHOOD DETECTION BY OLIGONUCLEOTIDES

(71) Applicant: Board of Regents, The University of Texas System, Austin, TX (US)

(72) Inventors: Edward Marcotte, Austin, TX (US); Jagannath Swaminathan, Austin, TX (US); Andrew Ellington, Austin, TX (US); Alexander Boulgakov, Austin, TX (US); Jon Laurent, Austin, TX (US); Raghav Shroff, Austin, TX (US); Erhu Xiong, Austin, TX (US); Sanchita Bhadra, Austin, TX (US); Brendan Floyd, Austin, TX (US); Eric Anslyn, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 1041 days.

(21) Appl. No.: 17/146,165

(22) Filed: Jan. 11, 2021

(65) Prior Publication Data
US 2021/0132076 A1    May 6, 2021

Related U.S. Application Data

(63) Continuation of application No. PCT/US2019/041562, filed on Jul. 12, 2019.

(60) Provisional application No. 62/697,179, filed on Jul. 12, 2018.

(51) Int. Cl.
G01N 33/68    (2006.01)
C12N 15/10    (2006.01)
G16B 15/00    (2019.01)

(52) U.S. Cl.
CPC ..... *G01N 33/6818* (2013.01); *C12N 15/1065* (2013.01); *G16B 15/00* (2019.02); *G01N 2458/00* (2013.01); *G01N 2570/00* (2013.01)

(58) Field of Classification Search
CPC .......... G01N 2570/00; G01N 33/6816; C12N 15/1065
See application file for complete search history.

(56) References Cited

U.S. PATENT DOCUMENTS

| 5,591,646 A | 1/1997 | Hudson et al. |
| 5,605,809 A | 2/1997 | Komoriya et al. |
| 5,902,723 A | 5/1999 | Dower et al. |
| 5,914,313 A | 6/1999 | Bouffard et al. |

(Continued)

FOREIGN PATENT DOCUMENTS

| EP | 1163519 | 12/2001 |
| EP | 2518514 | 10/2012 |

(Continued)

OTHER PUBLICATIONS

"Omniligase™-1", Product Information, Sigma-Aldrich. Downloaded from www.sigmaaldrich.com/deepweb/assets/sigmaaldrich/product/documents/218/840/sae0068pis.pdf on Sep. 8, 2023.

(Continued)

*Primary Examiner* — Samuel C Woolwine
*Assistant Examiner* — Lisa Horth
(74) *Attorney, Agent, or Firm* — Parker Highlander PLLC

(57) ABSTRACT

The present disclosure provides methods for molecular neighborhood detection of molecules, such as by iterative proximity ligation or split-and-pool methods for obtaining positional information.

20 Claims, 40 Drawing Sheets

Specification includes a Sequence Listing.

(56) References Cited

U.S. PATENT DOCUMENTS

| | | |
|---|---|---|
| 6,156,527 A | 12/2000 | Schmidt et al. |
| 6,326,136 B1 | 12/2001 | Lazar et al. |
| 6,902,936 B2 | 6/2005 | Qui et al. |
| 7,329,505 B2 | 2/2008 | Marmé |
| 7,351,540 B1 | 4/2008 | Carr |
| 7,468,258 B2 | 12/2008 | Owen |
| 7,641,862 B2 | 1/2010 | Noetzel et al. |
| 8,268,977 B2 | 9/2012 | Kool et al. |
| 8,569,481 B2 | 10/2013 | Koster et al. |
| 8,609,423 B2 | 12/2013 | Diller et al. |
| 8,778,685 B2 | 7/2014 | Diller et al. |
| 9,011,772 B2 | 4/2015 | Norderhaug et al. |
| 9,175,035 B2 | 11/2015 | Konno et al. |
| 9,188,586 B2 | 11/2015 | Fan et al. |
| 9,435,810 B2 | 9/2016 | Havranek et al. |
| 9,470,680 B2 | 10/2016 | Gonzalez et al. |
| 9,566,335 B1 | 2/2017 | Emili et al. |
| 9,580,736 B2 | 2/2017 | Tan et al. |
| 9,625,469 B2 | 4/2017 | Marcotte et al. |
| 9,689,868 B2 | 6/2017 | Kelts et al. |
| 9,983,211 B2 | 5/2018 | Diller et al. |
| 10,088,488 B2 | 10/2018 | Walker et al. |
| 10,302,591 B2 | 5/2019 | Bogoev et al. |
| 10,473,654 B1 | 11/2019 | Mallick |
| 10,481,162 B2 | 11/2019 | Emili et al. |
| 10,520,515 B2 | 12/2019 | Manneh et al. |
| 10,545,153 B2 | 1/2020 | Marcotte et al. |
| 11,072,816 B2 | 7/2021 | Gaublomme et al. |
| 11,105,812 B2 | 8/2021 | Marcotte et al. |
| 11,136,349 B2 | 10/2021 | Macmillan et al. |
| 11,143,648 B2 | 10/2021 | Ashworth et al. |
| 11,162,952 B2 | 11/2021 | Marcotte et al. |
| 11,435,358 B2 | 9/2022 | Marcotte et al. |
| 2002/0137045 A1 | 9/2002 | Lukhtanov et al. |
| 2002/0168682 A1 | 11/2002 | Goodlett et al. |
| 2002/0182117 A1 | 12/2002 | Coassin et al. |
| 2004/0029181 A1 | 2/2004 | Ueyama et al. |
| 2004/0053356 A1 | 3/2004 | Duewel et al. |
| 2004/0059522 A1 | 3/2004 | Han et al. |
| 2004/0086521 A1 | 5/2004 | Kropshofer et al. |
| 2004/0152155 A1 | 8/2004 | Norioka et al. |
| 2005/0003558 A1 | 1/2005 | Zuckermann et al. |
| 2005/0020810 A1 | 1/2005 | Ternansky et al. |
| 2007/0255455 A1 | 11/2007 | Busacca et al. |
| 2008/0044405 A1 | 2/2008 | Dedecker et al. |
| 2008/0090238 A1 | 4/2008 | Yang et al. |
| 2008/0206141 A1 | 8/2008 | Johannesen et al. |
| 2008/0242838 A1 | 10/2008 | Peters et al. |
| 2009/0264300 A1 | 10/2009 | Franch et al. |
| 2010/0047170 A1 | 2/2010 | Denmeade et al. |
| 2010/0047814 A1 | 2/2010 | Bruce et al. |
| 2010/0233095 A1 | 9/2010 | Duan et al. |
| 2010/0255518 A1 | 10/2010 | Goix et al. |
| 2010/0331199 A1 | 12/2010 | Stoll et al. |
| 2011/0027300 A1 | 2/2011 | Kamil et al. |
| 2012/0100559 A1 | 4/2012 | Hell et al. |
| 2014/0024124 A1 | 1/2014 | Shinohara et al. |
| 2014/0273004 A1 | 9/2014 | Havranek et al. |
| 2014/0349860 A1 | 11/2014 | Marcotte et al. |
| 2014/0378315 A1 | 12/2014 | Hendricks et al. |
| 2015/0065434 A1 | 3/2015 | Woster et al. |
| 2015/0087526 A1 | 3/2015 | Hesselberth |
| 2015/0185199 A1 | 7/2015 | Joo et al. |
| 2015/0330879 A1 | 11/2015 | Mai |
| 2016/0177380 A1 | 6/2016 | Ruan et al. |
| 2016/0194699 A1 | 7/2016 | Borodina et al. |
| 2016/0238612 A1 | 8/2016 | Sims et al. |
| 2016/0244828 A1 | 8/2016 | Mason |
| 2017/0212126 A1 | 7/2017 | Emili et al. |
| 2017/0276686 A1 | 9/2017 | Marcotte et al. |
| 2017/0343545 A1 | 11/2017 | Hadrup et al. |
| 2018/0030531 A1 | 2/2018 | DeRaad |
| 2018/0112212 A1 | 4/2018 | Nicol et al. |
| 2018/0133715 A1 | 5/2018 | Craig et al. |
| 2018/0179248 A1 | 6/2018 | MacMillan et al. |
| 2018/0284125 A1 | 10/2018 | Gordon et al. |
| 2019/0085412 A1 | 3/2019 | Fan et al. |
| 2019/0145982 A1 | 5/2019 | Chee et al. |
| 2020/0018768 A1 | 1/2020 | Marcotte et al. |
| 2020/0123593 A1 | 4/2020 | Rothberg et al. |
| 2020/0123594 A1 | 4/2020 | Rothberg et al. |
| 2020/0124613 A1 | 4/2020 | Marcotte et al. |
| 2020/0209254 A1 | 7/2020 | Reed et al. |
| 2020/0271661 A1 | 8/2020 | Sims |
| 2020/0345599 A1 | 11/2020 | Son et al. |
| 2020/0348307 A1 | 11/2020 | Beierle et al. |
| 2021/0010070 A1 | 1/2021 | Schnall-Levin et al. |
| 2021/0132076 A1 | 5/2021 | Marcotte et al. |
| 2021/0215706 A1 | 7/2021 | Marcotte et al. |
| 2021/0215707 A1 | 7/2021 | Marcotte et al. |
| 2021/0356473 A1 | 11/2021 | Anslyn et al. |
| 2022/0002342 A1 | 1/2022 | MacMillan et al. |
| 2022/0091130 A1 | 3/2022 | Marcotte et al. |
| 2022/0163536 A1 | 5/2022 | Marcotte et al. |

FOREIGN PATENT DOCUMENTS

| | | |
|---|---|---|
| EP | 3219712 | 9/2017 |
| EP | 3821010 | 5/2021 |
| GB | 2610078 | 2/2023 |
| WO | WO 91/00296 | 1/1991 |
| WO | WO 1993/012230 | 6/1993 |
| WO | WO 2007/070021 | 6/2007 |
| WO | WO 2007/104219 | 9/2007 |
| WO | WO 2007/120805 | 10/2007 |
| WO | WO 2008/109176 | 9/2008 |
| WO | WO 2009/090651 | 7/2009 |
| WO | WO 2009/158006 | 12/2009 |
| WO | WO 2010/05322 | 1/2010 |
| WO | WO 2010/044892 | 4/2010 |
| WO | WO 2010/065322 | 6/2010 |
| WO | WO 2010/065531 | 6/2010 |
| WO | WO 2012/019765 | 2/2012 |
| WO | WO 2012/083261 | 6/2012 |
| WO | WO 2012/178023 | 12/2012 |
| WO | WO 2013/112745 | 8/2013 |
| WO | WO 2014/031997 | 2/2014 |
| WO | WO 2014/106957 | 7/2014 |
| WO | WO 2014/124338 | 8/2014 |
| WO | WO 2014/210353 | 12/2014 |
| WO | WO 2015/00893 | 1/2015 |
| WO | WO 2015/035108 | 3/2015 |
| WO | WO 2015/153381 A2 | 10/2015 |
| WO | WO 2015/200893 | 12/2015 |
| WO | WO 2016/069124 | 5/2016 |
| WO | WO 2016/114970 | 7/2016 |
| WO | WO 2016/145416 | 9/2016 |
| WO | WO 2016/164530 | 10/2016 |
| WO | WO 2017/063093 | 4/2017 |
| WO | WO 2017/075265 | 5/2017 |
| WO | WO 2017/079573 | 5/2017 |
| WO | WO 2017/079593 | 5/2017 |
| WO | WO 2017/192633 | 11/2017 |
| WO | WO 2017/219027 | 12/2017 |
| WO | WO 2018/005559 | 1/2018 |
| WO | WO 2018/075693 | 4/2018 |
| WO | WO 2018/119447 | 6/2018 |
| WO | WO 2018/140966 | 8/2018 |
| WO | WO 2019/063827 | 4/2019 |
| WO | WO 2019/089836 | 5/2019 |
| WO | WO 2019/089846 | 5/2019 |
| WO | WO 2019/089851 | 5/2019 |
| WO | WO 2019/125982 | 6/2019 |
| WO | WO 2019/178033 | 9/2019 |
| WO | WO 2020/014586 | 1/2020 |
| WO | WO 2020/023488 | 1/2020 |
| WO | WO 2020/037046 | 2/2020 |
| WO | WO 2020/072907 | 4/2020 |
| WO | WO 2020/102741 | 5/2020 |
| WO | WO 2020/180335 | 9/2020 |
| WO | WO 2020/223133 | 11/2020 |
| WO | WO 2020/014586 A9 | 5/2021 |

(56) References Cited

FOREIGN PATENT DOCUMENTS

| WO | WO 2021/168083 | | 8/2021 |
|---|---|---|---|
| WO | WO 2021/211631 | A2 | 5/2023 |
| WO | WO 2023/091961 | A2 | 5/2023 |

OTHER PUBLICATIONS

"Single-Molecule Bioelectronics", Columbia University, downloaded from https://bioeeweb.ee.columbia.edu/wordpress/single-molecule-bioelectronics/ on Sep. 11, 2023.
Bailey, J. M. & Shively, J. E. Carboxy-terminal sequencing: formation and hydrolysis of C-terminal peptidylthiohydantoins. Biochemistry 29, 3145-56 (1990).
Bottecchia, Cecilia, and Timothy Noël. "Photocatalytic Modification of Amino Acids, Peptides, and Proteins." *Chemistry (Weinheim an der Bergstrasse, Germany)* vol. 25,1 (2019): 26-42.
Bouilly, Delphine et al. "Single-Molecule Reaction Chemistry in Patterned Nanowells." *Nano letters* vol. 16,7 (2016): 4679-85. doi:10.1021/acs.nanolett.6b02149.
Chu et al.: Carboxylic Acids as a Traceless Activation Group for Conjugated Additions: A Three-Step Synthesis of (+/−)-Pregabalin. Journal of the American Chemical Society, Jul. 28, 2014, vol. 136, pp. 10886-10889, entire document.
Hellenkamp, Björn et al. "Precision and accuracy of single-molecule FRET measurements—a multi-laboratory benchmark study." *Nature methods* vol. 15,9 (2018): 669-676. doi:10.1038/s41592-018-0085-0.
Horng, Jia-Cherng, and Ronald T. Raines. "Stereoelectronic effects on polyproline conformation." *Protein Science* 15.1 (2006): 74-83.
Kakinoki, Sachiro, Yoshiaki Hirano, and Masahito Oka. "On the stability of polyproline-I and II structures of proline oligopeptides." *Polymer Bulletin* 53 (2005): 109-115.
Kim et al., "C-terminal de novo sequencing of peptides using oxazolone-based derivation with bromine signature", Analytical Biochemical, 419:211-216, 2011.
Lee, Yoonhee et al. "Electrically Controllable Single-Point Covalent Functionalization of Spin-Cast Carbon-Nanotube Field-Effect Transistor Arrays." *ACS nano* vol. 12,10 (2018): 9922-9930. doi:10.1021/acsnano.8b03073.
MacDonald et al., One-Step Site-Specific Modification of Proteins with 2-Pyridinecarboxaldehyde Derivatives, A Dissertation submitted to University of California, 2016.
Maiti, et al. Bifunctional aryloxyphosphoramidate prodrugs of 2′-C-Me-uridine: synthesis and anti-HCV activity. Organic & biomolecular chemistry vol. 14,37 (2016): 8743-8757.
PCT/US2016/035716 International Search Report and Written Opinion dated Sep. 13, 2016.
PCT/US2021/027155 International Preliminary Report on Patentability dated Oct. 13, 2023.
PCT/US2022/079979 International Search Report and Written Opinion mailed Apr. 14, 2023.
Rauniyar, et al., Isobaric Labeling-based relative quantification in shotgun proteomics. Journal of proteome. 2014.13, 5293-5309.
Schuler, Benjamin et al. "Polyproline and the "spectroscopic ruler" revisited with single-molecule fluorescence." *Proceedings of the National Academy of Sciences of the United States of America* vol. 102,8 (2005): 2754-9. doi:10.1073/pnas.0408164102.
Swaminathan et al., "A theoretical justification for single molecule peptide sequence," PLoS computational biology, 11(2): e1004080 (2015).
Van der Velde, Jasper H M et al. "A simple and versatile design concept for fluorophore derivatives with intramolecular photostabilization." *Nature communications* vol. 7 10144. Jan. 11, 2016.
Vernick, Sefi et al. "Electrostatic melting in a single-molecule field-effect transistor with applications in genomic identification." *Nature communications* vol. 8 15450. May 18, 2017, doi:10.1038/ncomms15450.
Zuo, Zhiwei et al. "Dual catalysis. Merging photoredox with nickel catalysis: coupling of α-carboxyl sp$^3$-carbons with aryl halides." *Science (New York, N.Y.)* vol. 345,6195 (2014): 437-40. doi: 10.1126/science.1255525.
C387. Zuo, Zhiwei, and David W C MacMillan. "Decarboxylative arylation of α-amino acids via photoredox catalysis: a one-step conversion of biomass to drug pharmacophore." *Journal of the American Chemical Society* vol. 136,14 (2014): 5257-60. doi:10.1021/ja501621q.
Office Communication issued in Chinese Patent Application No. 201980049639.X, dated Nov. 28, 2023. English Translation.
"The catalog for Molecular Probes", downloaded from: web.archive.org/web/20101217092018/http://www.mobitec.de/probes/docs/sections/0101.pdf, available 2010.
Abelin et al., "Mass Spectrometry Profiling of HLA-Associated Peptidomes in Mono-allelic Cells Enables More Accurate Epitope Prediction", *Immunity*, 46(2):315-326, 2017.
Aitken et al., "An Oxygen Scavenging System for Improvement of Dye Stability in Single-Molecule Fluorescence Experiments," *Biophysical Journal*, 94(5):1826-1835, 2008.
Alfaro et al., "The emerging landscape of single-molecule protein sequencing technologies", *Nature methods*, 18 (6): 604-617, 2021.
Altman et al., "Enhanced photostability of cyanine fluorophores across the visible spectrum," *Nature Methods*, 9:428-429, 2012.
Altman et al., "Cyanine fluorophore derivatives with enhanced photostability," *Nature Methods*, 9(1): 68-71, 2012.
Andrews et al., "A thermodynamic model for Nap1-histone interactions." *The Journal of biological chemistry*, 283(47): 32412-8, 2008.
Antos et al., "Site-specific protein labeling via sortase-mediated transpeptidation", *Current protocols in protein science*, 89(1):15-3, 2017.
Armbrecht et al., Single-cell protein profiling in microchambers with barcoded beads, *Microsyst Nanoeng*, 5(55), 2019.
Axelrod et al., "Cell-substrate contacts illuminated by total internal reflection fluorescence," *Journal of Cell Biology*, 89(1):141-145, 1981.
Backert & Kohlbacher, "Immunoinformatics and epitope prediction in the age of genomic medicine", *Genome Med.*, 7(119), 2015.
Baez et al., "Mass spectrometry in studies of protein thiol chemistry and signaling: opportunities and caveats", *Free Radic Biol Med.*, 80:191-211, 2015.
Bailey and Shively, "Carboxy-terminal sequencing: formation and hydrolysis of C-terminal peptidylthiohydantoins," *Biochemistry*, 29(12):3145-3156, 1990.
Balister et al., "Percolation, connectivity, coverage and colouring of random geometric graphs", *Handbook of Large-Scale Random Networks*, 18:117-142, 2008.
Bamberger et al., "Protein Footprinting via Covalent Protein Painting Reveals Structural Changes of the Proteome in Alzheimer's Disease", *J Proteome Res.*, 20(5):2762-2771, 2021.
Baslé et al., "Protein Chemical Modification on Endogenous Amino Acids", *Chemistry & Biology*, 17:213-227, 2010.
Bassani-Sternberg et al., "Mass spectrometry of human leukocyte antigen class I peptidomes reveals strong effects of protein abundance and turnover on antigen presentation", *Mol Cell Proteomics*, 14(3):658-73, 2015.
Bendall et al., "Single-Cell Mass Cytometry of Differential Immune and Drug Responses Across a Human Hematopoietic Continuum," *Science*, 332(6030):687-96, 2011.
Berg et al., "Peptide oligomers for holographic data storage," *Nature*, 383: 505-508, 1996.
Bethell et al., "Kinetics and mechanism of the Edman degradation," *Chem. Comm.*, 10:189-190, 1965.
Bhat et al., "The visible touch: in planta visualization of protein-protein interactions by fluorophore-based methods," *Plant Methods*, 2(12), 2006.
Biedka et al., "Reversible Click Chemistry Tag for Universal Proteome Sample Preparation for Top-Down and Bottom-Up Analysis," *Journal of proteome research*, 20(10): 4787-4800, 2021.
Billingsley et al., "Single-molecule studies of DNA transcription using atomic force microscopy," *Phys. Biol.*, 9:021001, 2012.

(56) References Cited

OTHER PUBLICATIONS

Bloom et al., "Decarboxylative alkylation for site-selective bioconjugation of native proteins via oxidation potentials," *Nature Chemistry*, 10(2):2015-2011, 2017.
Bonnet et al., "Amplifying Genetic Logic Gates," *Science*, 340(6132): 599-603, 2013.
Borgo et al., "Computer-aided design of a catalyst for Edman degradation utilizing substrate-assisted catalysis," *Protein Sci.*, 24(4):571-579, 2015.
Bottecchia et al., "Photocatalytic modification of amino acids, peptides, and proteins", *Chemistry*, 25(1): 26-42, 2019.
Bradski et al., "OpenCV: an open-source computer vision library," *Dr. Dobb's Journal of Software Tools*, 2000.
Brandt et al., Quenching processes. www.rose-hulman.edu/~brandt/Fluorescence/Quenching_processes.pdf, downloaded Feb. 18, 2016.
Branton et al., "The potential and challenges of nanopore sequencing," *Nat. Biotechnol.*, 26 (10): 1146-1153, 2008.
Braslavsky et al., "Sequence information can be obtained from single DNA molecules," *Proceedings of the National Academy of Sciences of the United States of America*, 100(7):3960-3964, 2003.
Brennick et al., "Neoepitopes as cancer immunotherapy targets: key challenges and opportunities", *Immunotherapy*, 9(4):361-371, 2017.
Brewis et al., "Proteomics technologies for the global identification and quantification of proteins", *Advances in Protein Chemistry*, 80(1):1-44, 2010.
Brosseron et al., "Stepwise isolation of human peripheral erythrocytes, T lymphocytes, and monocytes for blood cell proteomics," *Proteomics Clin. Appl.*, 6(9-10):497-501, 2012.
Brown et al., "Neo-antigens predicted by tumor genome meta-analysis correlate with increased patient survival." Genome research, 24(5):743-50, 2014.
Buschmann, & Bystrykh et al., "Levenshtein error-correcting barcodes for multiplexed DNA sequencing", *BMC Bioinformatics* 14: 272, 2013.
Cafferty et al., "Storage of information using small organic molecules," *ACS Central Science*, 5: 911-916, 2019.
Cang et al., "Giant suppression of photobleaching for single molecule detection via the Purcell effect," *Nano Letters*, 13(12):5949-5953, 2013.
Cannon et al., "A Dual-Mode Single-Molecule Fluorescence Assay for the Detection of Expanded CGG Repeats in Fragile X Syndrome," *Molecular Biotechnology*, 53(1): 19-28, 2013.
Cao et al. "Selective Enrichment and Quantification of N-Terminal Glycine Peptides via Sortase A Mediated Ligation." *Analytical chemistry*, 90 (24): 14303-14308, 2018.
Caron et al., "A case for a human immuno-peptidome project consortium", *Immunity*, 47(2):203-8, 2017.
Caron et al., "Analysis of Major Histocompatibility Complex (MHC) Immunopeptidomes Using Mass Spectrometry", *Mol Cell Proteomics*, 14(12):3105-17, 2015.
Chalker et al., "Chemical Modification of Proteins at Cysteine: Opportunities in Chemistry and Biology," *Chemistry—An Asian Journal*, 4(5): 630-640, 2009.
Chang et al., "Manual solid phase sequence analysis of polypeptides using 4-N,N-dimethylaminoazobenzene 4'-isothiocyanate," *Biochim. Biophys. Acta*, 578(1):188-195, 1979.
Chelius et al., Capture of peptides with N-terminal serine and threonine: a sequence-specific chemical method for Peptide mixture simplification. *Bioconjug Chem.*, 14(1):205-11, 2003.
Chen et al., "An efficient and versatile approach for the preparation of a rhodamine B ester bioprobe library," *Dyes and Pigments*, 94(2): 296-303, 2012.
Chen et al., "Reactivity of functional groups on the protein surface: development of epoxide probes for protein labeling." *Journal of the American Chemical Society*, 125(27): 8130-8133, 2003.
Chen et al., "Selective chemical labeling of proteins", *Org. Biomol. Chem.* 14: 5417-5439, 2016.
Chen et al., "Spatially resolved, highly multiplexed RNA profiling in single cells", *Science*, 348: 6233, 2015.

Choi et al., "Core-shell silica nanoparticles as fluorescent labels for nanomedicine," *J. of Biomedical Optics*, 12(6): 064007, 2007.
Church et al., "Next-Generation Digital Information Storage in DNA." *Science*, 337(6102), 2012.
Clement et al., "The Dendritic Cell Major Histocompatibility Complex II (MHC II) Peptidome Derives from a Variety of Processing Pathways and Includes Peptides with a Broad Spectrum of HLA-DM Sensitivity." *The Journal of biological chemistry*, 291(11) : 5576-5595, 2016.
Cline et al., "Kinetics and mechanisms of the aminolysis of N-hydroxysuccinimide esters in aqueous buffers," *Journal of Organic Chemistry*, 53(15):3583-3586, 1988.
Cockrill et al., "Efficient micro-recovery and guanidination of peptides directly from MALDI target spots," *BioTechniques*, 38(2):301-304, 2005.
Cohen et al., "Red cell life span heterogeneity in hematologically normal people is sufficient to alter HbA1c," *Blood*, 112(10): 4284-4291, 2008.
Colombani et al., "Polymerization kinetics: monitoring monomer conversion using an internal standard and the key role of sample to." *J. Chem, Ed.*, 88(1):116-121, 2011.
Co-pending U.S. Appl. No. 17/491,485, inventors Marcotte; Edward et al., filed Sep. 30, 2021.
Co-pending U.S. Appl. No. 17/738,281, inventors Marcotte; Edward et al., filed May 6, 2022.
Co-pending U.S. Appl. No. 17/964,201, inventors Somekh; Tal et al., filed Oct. 12, 2022.
Cordes and Blum, "Opportunities and challenges in single-molecule and single-particle fluorescence microscopy for mechanistic studies of chemical reactions," *Nat. Chem.*, 5(12):993-999, 2013.
Cordes et al., "On the Mechanism of Trolox as Antiblinking and Antibleaching Reagent," *Journal of the American Chemical Society*, 131 (14): 5018-19, 2009.
Croop et al., "Single-shot, shadowless total internal reflection fluorescence microscopy via annular fiber bundle", *Optics Letters*, 45(23), 2020.
Cuppoletti et al., "Oligomeric Fluorescent Labels for DNA," *Bioconjugate Chem.*, 16:528-534, 2005.
Czaplyski et al., "Substituent effects on the turn-on kinetics of rhodamine-based fluorescent pH probes," *Organic & Biomolecular Chemistry*, 12(3):526-533, 2014.
Da Costa et al., "How low can you go? A current perspective on low-abundance proteomics," *Trends in Analytical Chemistry*, 93: 171-182, 2017.
D'Amici et al., "Red blood cell storage in SAGM and AS3: a comparison through the membrane two-dimensional electrophoresis proteome," *Blood Transfus.*, 10, No. Suppl 2: s46-s54, 2012.
Declaration of Dr. Edward Marcotte filed in U.S. Appl. No. 14/128,247, filed Jul. 7, 2016.
Declaration of Dr. Edward Marcotte filed in U.S. Appl. No. 14/128,247, filed Sep. 2, 2016.
Declaration of Dr. Jagannath Swaminathan filed in U.S. Appl. No. 14/128,247, filed Jan. 26, 2016.
Dempsey et al., "Evaluation of fluorophores for optimal performance in localization-based super-resolution imaging," *Nat. Methods*, 8(12):1027-1036, 2011.
Dixon et al., "Reversible blocking of amino groups with citraconic anhydride", *Biochem J.*, 109(2):312-4, 1968.
Doll et al., "Visualization of Protein-Specific Glycosylation inside Living Cells", *Angewandte Chemie International Edition*, 55(6): 2262-2266, Supporting Information, 2016.
Dong et al., "Label-free quantitation of glycated hemoglobin in single red blood cells by transient absorption microscopy and phasor analysis", *Sci Adv.*, 5(5): eaav0561, 2019.
Donnert et al., "Major signal increase in fluorescence microscopy through dark-state relaxation," *Nature Methods*, 4 (1): 81-86, 2006.
Doolittle et al., "A simple solid-phase amino acid sequencer employing a thioacetylation stepwise degradation procedure", *Anal Biochem.*, 78(2):491-505, 1977.
Duan et al., "ProC-TEL: Profiling of Protein C-Termini by Enzymatic Labeling", *Protein Terminal Profiling*, 135-144, 2017.
Dudley et al., Adoptive-cell-transfer therapy for the treatment of patients with cancer, *Nat Rev Cancer*, 3(9):666-75, 2003.

(56) References Cited

OTHER PUBLICATIONS

Duffy et al., "Clinical use of biomarkers in breast cancer: Updated guidelines from the European Group on Tumor Markers (EGTM)", *Eur J Cancer*, 75:284-298, 2007.

Dunn et al., "Techniques for phosphopeptide enrichment prior to analysis by mass spectrometry", *Mass Spectrom Rev.*, 29(1):29-54, 2010.

Edman et al., "A Protein Sequenator," *European Journal of Biochemistry*, 1(1): 80-91, 1967.

Edman et al., "Method for determination of the amino acid sequence in peptides," *Acta Chemica Scandinavica*, 4(7): 283-293, 1950.

Edman et al., "A method for the determination of amino acid sequence in peptides," *Archives of Biochemistry*, 22(3):475, 1949.

Edman et al., "Preparation of Phenyl Thiohydantoins from Some Natural Amino Acids", *Acta Chemica Scandinavica*, 277-282, 1950.

Egloff et al., Engineered peptide barcodes for in-depth analyses of binding protein libraries, *Nature Methods*, 16: 421-428, 2018.

Eid et al., "Real-Time DNA Sequencing from Single Polymerase Molecules," *Science*, 323(5910): 133-138, 2009.

Eliason et al., "Temperature effect on reaction rates." *J. Chem. Ed.*, 58(4):354, 1981.

Ellson et al., Graphviz and Dynagraph—Static and Dynamic Graph Drawing Tools, *Graph Drawing Software: Mathematics and Visualization*, 127-148, 2004.

Eng et al., "An approach to correlate tandem mass spectral data of peptides with amino acid sequences in a protein database", *J Am Soc Mass Spectrom.*, 5(11):976-89, 1994.

EP19834092.9 extended European Search Report dated Mar. 18, 2022.

EP19849103.7 Extended European Search Report dated May 16, 2022.

EP19868673.5 Extended European Search Report dated Jul. 19, 2022.

EP20150854171 European Search Report dated Feb. 12, 2018.

EP20150854171 Extended European Search Report dated Jun. 6, 2018.

EP20180215779 European Search Report dated Jul. 26, 2019.

Erdős & Rényi et al., "On the strength of connectedness of a random graph", *Acta Math. Acad. Sci. Hung.*, 12(1):261-267, 1964.

European Search Report issued in European Patent Application No. 19849848.6 mailed Sep. 1, 2022.

Feng et al., "Imaging Neuronal Subsets in Transgenic Mice Expressing Multiple Spectral Variants of GFP," *Neuron*, 28:41-51, 2000.

Fina et al., "The Alpha Effect. A Review" *Int. J. Chem. Kinet.*, 5: 1-26, 1973.

Fields et al., "The interplay of biology and technology," *PNAS*, 98(18):10051-10054, 2001.

Fredkin et al., "Trie memory," *Communications of the ACM*, 3(9):490-499, 1960.

Frey et al., "Chemical Derivatization of Peptide Carboxyl Groups for Highly Efficient Electron Transfer Dissociation," *Journal of the American Society for Mass Spectrometry*, 24(11):1710-1721, 2013.

Fukuzaki et al., "Adsorption of protein onto stainless-steel surfaces," *J. Ferro. Bioeng.*, 80(1):6-11, 1995.

Gajer et al., "A Multi-dimensional Approach to Force-Directed Layouts of Large Graphs", *Lecture notes in Computer Science: International Symposium on Graph Drawing*, 84:211-221, 2002.

Garcia-Parajo et al., "The nature of fluorescence emission in the red fluorescent protein DsRed, revealed by single-molecule detection," *Proceedings of the National Academy of Sciences*, 98(25):14392-14397, 2001.

Garreau et al., "C-Terminal Bioconjugation of Peptides through Photoredox Catalyzed Decarboxylative Alkynylation," *Angewandte Chemie*, 58 (24):8182-8186, 2019.

Gawad et al., "Single-cell genome sequencing: current state of the science", *Nature Reviews Genetics*, 17(3): 175, 2016.

Ghaemmaghami et al., "Global analysis of protein expression in yeast," *Nature*, 425 :737-41, 2003.

Gilmore et al., "N-Terminal Protein Modification through a Biomimetic Transamination Reaction‡," *Angew. Chem. Int. Ed.*, 45:5307-5311, 2006.

Gnjatic et al., "Identifying baseline immune-related biomarkers to predict clinical outcome of immunotherapy", *J Immunother Cancer*, 5:44, 2017.

Godkin et al., "Characterization of novel HLA-DR11-restricted HCV epitopes reveals both qualitative and quantitative differences in HCV-specific CD4+ T cell responses in chronically infected and non-viremic patients", *Eur J Immunol.*, 31(5):1438-46, 2001.

Goodman et al., Tumor Mutational Burden as an Independent Predictor of Response to Immunotherapy in Diverse Cancers, *Mol Cancer Ther.*, 16(11):2598-2608, 2017.

Gooley et al., "Glycosylation sites identified by detection of glycosylated amino acids released from Edman degradation: The identification of Xaa-Pro-Xaa-Xaa as a motif for Thr-O-glycosylation," *Biochemical and Biophysical Research Communications*, 178(3): 1194-1201, 1991.

Gullberg et al., "A sense of closeness: protein detection by proximity ligation", *Current Opinion in Biotechnology*, 14(1): 82-86, 2003.

Gyarmati et al., "Reversible disulphide formation in polymer networks: A versatile functional group from synthesis to applications", *European Polymer Journal*, 49:1268-1286, 2013.

György et al., "Citrullination: a posttranslational modification in health and disease", *Int J Biochem Cell Biol.*, 38(10):1662-77, 2006.

Haab et al., "Applications of antibody array platforms," *Current Opinion in Biotechnology*, 17(4): 415-421, 2006.

Haensch et al., "Chemical modification of self-assembled silane based monolayers by surface reactions", *Chem. Soc. Rev.*, 39: 2323-34, 2010.

Hamada et al., "A novel N-terminal degradation reaction of peptides via N-amidination" *Bioog. Med. Chem. Lett.* 26:1690-1695, 2016.

Han et al., "Current developments in stepwise edman degradation of peptides and proteins," *International Journal of Biochemistry*, 17(4):429-445, 1985.

Hanay et al., "Single-protein nanomechanical mass spectrometry in real time," *Nature Nanotechnology*, 7(9): 602-608, 2012.

Haralambidis et al., "The preparation of polyamide-oligonucleotide probes containing multiple non-radioactive labels", *Nucleic Acids Research*, 18(3), 1990.

Harris et al., "Single-Molecule DNA Sequencing of a Viral Genome," *Science*, 320(5872): 106-109, 2008.

Harris et al., "Immuno-oncology combinations: raising the tail of the survival curve", *Cancer Biol Med.*, 13(2):171-93, 2016.

Hartmann et al., "A universal live cell barcoding-platform for multiplexed human single cell analysis," *Sci Rep.*, 8(1):1-10, 2018.

Havugimana et al., "A Census of Human Soluble Protein Complexes," *Cell*, 150(5): 1068-1081, 2012.

Herbrink et al., "Solid phase Edman degradation. High yield attachment of tryptic protein fragments to aminated supports," *FEBS Letters*, 60(2):313-316, 1975.

Hermanson et al., "Bioconjugate Techniques: Bioconjugate Techniques", *Elsevier*, 2013.

Hernandez et al., "Solution-phase and solid-phase sequential, selective modification of side chains in KDYWEC and KDYWE as models for usage in single-molecule protein sequencing†," *New J. Chem.*, 41(2):462-469, 2017.

Higgins et al., "Kinetic analysis of the nonenzymatic glycosylation of hemoglobin," *J. Biol. Chem.*, 256(10) :5204-5208, 1981.

Hoebe et al., "Controlled light-exposure microscopy reduces photobleaching and phototoxicity in fluorescence live-cell imaging," *Nature Biotechnology*, 25(2):249-253, 2007.

Hong et al., "ProtSeq: Toward high-throughput, single-molecule protein sequencing via amino acid conversion into DNA barcodes", *iScience*, 25(1):103586, 2021.

Horton et al., "A Highly Reactive Colored Reagent with Selectivity for the Tryptophan Residue in Proteins. 2-Hydroxy-5-nitrobenzyl Bromide[1]," *Journal of the American Chemical Society*, 87(5):1126-1132, 1965.

Howard et al., "Solid-Phase Peptide Capture and Release of Bulk and Single-Molecule Proteomics", *bioRxiv*, dx.doi.org/10.1101/2020.01.13.904540, 2020.

(56) References Cited

OTHER PUBLICATIONS

Huang et al., "Super resolution fluorescence microscopy," *Annu. Rev. Biochem.*, 78: 993-1016, 2009.
Huang et al., "Three-Dimensional Super-Resolution Imaging by Stochastic Optical Reconstruction Microscopy," *Science*, 319(5864): 810-813, 2008.
Hughes et al., "Single-cell western blotting", *Nat Methods*, 11(7):749-55. doi: 10.1038/nmeth.2992, 2014.
Hwang et al., "Identification of Missing Proteins in Human Olfactory Epithelial Tissue by Liquid Chromatography-Tandem Mass Spectrometry", *J Proteome Res.*, 17(12):4320-4324, 2018.
Imakyure et al., "A fluorogenic reagent for amino acids in liquid chromatography, 4-(2-cyanoisoindolyl)phenylisothiocyanate," *Anal. Chim. Acta*, 291(1-2):197-204, 1994.
Inglis et al., "Chemical procedures for C-terminal sequencing of peptides and proteins," *Anal. Biochem.*, 195(2):183-96, 1991.
Ingolia et al., "Genome-Wide Analysis in Vivo of Translation with Nucleotide Resolution Using Ribosome Profiling," *Science*, 324(5924):218-223, 2009.
International Search Report and Written Opinion issued in PCT/US2022/017642 on Jul. 19, 2022.
International Search Report and Written Opinion issued in PCT/US2022/031022 on Aug. 19, 2022.
International Search Report and Written Opinion issued in PCT/US2022/74750 on Nov. 7, 2022.
Ireland et al., "Double Coupling Edman Chemistry for High-Sensitivity Automated Protein Sequencing," *J. Protein Chem.*, 16(5):491-93, 1997.
Isidro-Llobet et al., "Amino acid-protecting groups," *Chemical Reviews*, 109(6):2455-2504, 2009.
Jain et al., "Stoichiometry and assembly of mTOR complexes revealed by single-molecule pulldown," *PNAS*, 111(50): 17833-17838, 2014.
Jameson et al., "Fluorescence Polarization/Anisotropy in Diagnostics and Imaging," *Chem. Rev.*, 110 (5):2685-2708, 2010.
Javitt et al., "The proteasome regulator PSME4 drives immune evasion and abrogates anti- tumor immunity in NSCLC", *bioRxiv*, doi.org/10.1101/2021.10.24.464690, 2021.
Jin et al., "Recent advances in dynamic covalent chemistry", *Chem Soc Rev.*, 42(16):6634-54, 2013.
Jin et al., "Study on New Edman-type Reagents," *in Methods in Protein Sequence Analysis (Wittmann-Liebold, B., Ed.)*, 34-41, Springer Berlin Heidelberg, Berlin, Heidelberg, 1989.
Johnson et al. "Reversible macrocyclization of peptides with a conjugate acceptor", *Organic letters*, 19(7): 1654-1657, 2017.
Joo et al., "Advances in single-molecule fluorescence methods for molecular biology," *Annual Review of Biochemistry*, 77:51-76, 2008.
Julka et al., "Quantification in proteomics through stable isotope coding: a review," *Journal of Proteome Research*, 3(3):350-363, 2004.
Jungmann et al., "Quantitative super-resolution imaging with qPAINT," *Nat. Methods*, 13(5):439-442, 2016.
Kamada and Kawai et al., "An algorithm for drawing general undirected graphs", *Inf. Process. Lett.*, 31: 7-15, 1989.
Kamada and Soderberg., "Flow-assisted assembly of nanostructured protein microfibers", *Applied Physical Sciences*, 114(6):1232-1237, 2017.
Katritzky et al., "Fluorescent labeling of peptides on solid phase," *Org. Biomol. Chem.*, 6:4582-4586, 2008.
Kelly et al., "Targeted nanoparticles for imaging incipient pancreatic ductal adenocarcinoma," *PLoS Medicine*, 5(4), e85, 2008.
Keough et al., "Derivatization procedures to facilitate de novo sequencing of lysine-terminated tryptic peptides using postsource decay matrix-assisted laser desorption/ionization mass spectrometry," *Rapid Communications in Mass Spectrometry*, 14(24):2348-2356, 2000.
Kim et al., "C-terminal de novo sequencing of peptides using oxazolone-based derivatization with bromine signature",*Anal. Biochem.*, 419:211-6, 2011.

Kinraide et al., "Use of a Gouy-Chapman-Stern model for membrane-surface electrical potential to interpret some features of mineral rhizotoxicity," *Plant Physiol.*, 106:1583-1592, 1994.
Klement et al., "Enrichment of O-GlcNAc modified proteins by the periodate oxidation-hydrazide resin capture approach", *J Proteome Res.*, 9(5):2200-6, 2010.
Ko et al., "Enhanced electron transfer dissociation of peptides modified at C-terminus with fixed charges," *Journal of American Society for Mass Spectrometry*, 23(11): 1991-2000, 2012.
Koide et al., "Development of NIR fluorescent dyes based on Si-rhodamine for in vivo imaging," *Journal of the American Chemical Society*, 134(11):5029-5031, 2012.
Konry et al., "Droplet-based microfluidic platforms for single T cell secretion analysis of IL-10 cytokine," *Biosens Bioelectron.*, 26(5): 2707-2710, 2011.
Kool et al., "Fast alpha nucleophiles: structures that undergo rapid hydrazone/oxime formation at neutral pH", *Org Lett.*, 16(5):1454-7, 2014.
Koos et al., "Analysis of protein interactions in situ by proximity ligation assays," *Current Topics in Microbiology and Immunology*, 377:111-126, 2014.
Kovalova et al., "Stepwise triple-click functionalization of synthetic peptides", *Organic & biomolecular chemistry*, 16(33): 5960-5964, 2018.
Krusemark et al., "Complete chemical modification of amine and acid functional groups of peptides and small proteins," *Methods in molecular biology*, 753:77-91, 2011.
Kuyama et al., "An approach to quantitative proteome analysis by labeling tryptophan residues," *Rapid Communications in Mass Spectrometry*,17(14):1642-1650, 2003.
Lakowicz et al., "Mechanisms and Dynamics of Fluorescence Quenching," In: *Principles of Fluorescence Spectroscopy*, 331-351. Boston, MA: Springer US, 2006.
Lamesch et al., "hORFeome v3.1: a resource of human open reading frames representing over 10,000 human genes," *Genomics*, 89: 307-315, 2007.
Lang et al., "Cellular incorporation of unnatural amino acids and bioorthogonal labeling of proteins", *Chem Rev.*, 114(9):4764-806, 2014.
Laursen et al., "Solid-Phase Edman Degradation: An Automatic Peptide Sequencer," *European Journal of Biochemistry*, 20(1):89-102, 1971.
Lee et al., "A Simple Outline of Methods for Protein Isolation and Purification", *Endocrinol Metab*, 32(1):18-22, 2017.
Lee et al., "Evidence of preserved collagen in an Early Jurassic sauropodomorph dinosaur revealed by synchrotron FTIR microspectroscopy," *Nature Communications*, 8(1):1-8, 2017.
Lee et al., "Update on Tumor Neoantigens and Their Utility: Why It Is Good to Be Different", *Trends Immunol.*, 39(7):536-548, 2018.
Leigh-Smith et al., "Blood boosting," *British Journal of Sports Medicine*, 38(1): 99-101, 2004.
Li et al. "Synthesis and biological evaluation of nonsymmetrical aromatic disulfides as novel inhibitors of acetohydroxyacid synthase," *Bioorganic & Medicinal Chemistry Letters*, 23(13):3723-3727, 2013.
Li et al., "Selective labeling of histidine by a designed fluorescein-based probe," *Talanta*, 62(2): 367-371, 2004.
Li et al., "Constrained De Novo Sequencing of neo-Epitope Peptides using Tandem Mass Spectrometry", *Res Comut. Mol Bio.*, 10812:138-153, 2018.
Li et al., "N-terminal α-amino group modification of antibodies using a site-selective click chemistry method," *MABS* , 10(5):712-719, 2018.
Lin et al., "Efforts and Challenges in Engineering the Genetic Code", *Life*, 7(1):12, 2017.
Lin et al., "Examining histone posttranslational modification patterns by high-resolution mass spectrometry", *Methods Enzymol.*, 512:3-28, 2012.
Liu et al., "On the dependency of cellular protein levels on mRNA abundance," *Cell*, 165: 535-550, 2016.
Lo et al., "Quantification of protein levels in single living cells," *Cell Reports*, 13:2634-2644, 2015.
Lotze et al., "Peptide-tags for site-specific protein labelling in vitro and in vivo", *Molecular Biosystems*, 12(6):1731-1745, 2016.

(56) References Cited

OTHER PUBLICATIONS

Luchowski et al., "Single molecule studies of multiple-fluorophore labeled antibodies. Effect of homo-FRET on the number of photons available before photobleaching," *Curr. Pharm. Biotechnol.,* 9(5):411-420, 2008.
Lukinavious et al., "A near-infrared fluorophore for live-cell super-resolution microscopy of cellular proteins," *Nature Chemistry,* 5(2):132-139, 2013.
Lyon et al., "Self-hydrolyzing maleimides improve the stability and pharmacological properties of antibody-drug conjugates," *Nat. Biotechnol.,* 32(10):1059-1062, 2014.
Macbeath et al., "Printing small molecules as microarrays and detecting protein-ligand interactions en masse," *Journal of the American Chemical Society,* 121(34):7967-7968, 1999.
MacDonald et al., "One-step site-specific modification of native proteins with 2-pyridinecarboxyaldehydes," *Nat. Chem. Biol.,* 11(5):326-331, 2015.
Maiti et al., "Bifunctional aryloxyphosphoramidate prodrugs of 2'-C-Me-uridine: synthesis and anti-HCV activity", *Organic & biomolecular chemistry,*14(37): 8743-8757, 2016.
Mallam et al., "Systematic discovery of endogenous human ribonucleoprotein complexes," *Cell Rep.,* 29(5): 1351-1368.e5, 2019.
Margulies et al., "Genome sequencing in microfabricated high-density picolitre reactors", *Nature,* 437: 376-380 ,2005.
Martins et al., "Selective Recognition of Amino Acids and Peptides by Small Supramolecular Receptors", *Molecules,* 26(1):106, 2020.
Martos-Maldonado et al., "Selective N-terminal acylation of peptides and proteins with a Gly-His tag sequence", *Nat Commun.,* 9: 3307, 2018.
Matsunaga et al., "Proton: a major factor for the racemization and the dehydration at the cyclization/cleavage stage in the Edman sequencing method," *Anal. Chem.,* 68(17) :2850-2856, 1996.
Maude et al., "Tisagenlecleucel in Children and Young Adults with B-Cell Lymphoblastic Leukemia", *N Engl J Med.,* 378(5):439-448, 2018.
Mazutis et al., "Single-cell analysis and sorting using droplet-based microfluidics," *Nat. Protoc.,* 8(5): 870-891, 2013.
Mazzone et al., "Evaluating Molecular Biomarkers for the Early Detection of Lung Cancer: When Is a Biomarker Ready for Clinical Use? An Official American Thoracic Society Policy Statement." *American journal of respiratory and critical care medicine,* 196(7): e15-e29, 2017.
Mcalpine et al., "Visualizing Functional Group Distribution in Solid-Support Beads by Using Optical Analysis," *Chemistry—A European Journal,* 5(12): 3528-3532, 1999.
Merrifield et al., Solid Phase Peptide Synthesis. I. The Synthesis of a Tetrapeptide, *Journal of the American Chemical Society,* 85 (14): 2149-2154, 1963.
Millington et al., "Aryl hydrazides as linkers for solid phase synthesis which are cleavable under mild oxidative conditions," *Tetrahedron Letters,* 39(39): 7201-7204, 1998.
Miyamoto et al., Peptide barcoding for establishment of new types of genotype-phenotype linkages, PLOS one, Apr. 23, 2019.
Miyashita et al., "Attomole level protein sequencing by Edman degradation coupled with accelerator mass spectrometry," *Proc. Natl. Acad. Sci.,* 98(8):4403-4408, 2001.
Moffett et al., "Tryptophan and the immune response," *Immunology and Cell Biology,* 81(4):247-265, 2003.
Mohanty et al., "Advancing cell biology and functional genomics in maize using fluorescent protein-tagged lines," *Plant Physiology,* 149: 601-605, 2009.
Momaya et al., "Performance-enhancing substances in sports: a review of the literature" *Sports Med.,* 45(4): 517-531, 2015.
Monfort et al., "Plasticizers excreted in urine: indication of autologous blood transfusion in sports," *Transfusion (Paris),* 52(3):647-657, 2012.
Müller et al., Current Strategies for the Identification of Immunogenic Epitopes of Tumor Antigens, *Immunotherapy of Cancer,* 21-44, 2006.

Muramoto et al., "The application of fluorescein isothiocyanate and high-performance liquid chromatography for the microsequencing of proteins and peptides," *Anal. Biochem.,* 141(2):446-450, 1984.
Murata et al., "Solid-phase synthesis of protein-polymers on reversible immobilization supports", *Nat Commun.,* 9: 845, 2018.
Nagaraj et al., "Deep proteome and transcriptome mapping of a human cancer cell line," *Molecular Systems Biology,* 7:548-548, 2011.
Nakajima et al., "Mass spectrometry-based sequencing of protein C-terminal peptide using α-carboxyl group-specific derivatization and COOH capturing", *Anal. Biochem.,* 428: 167-172, 2012.
Neefjes et al., "Towards a systems understanding of MHC class I and MHC class II antigen presentation", *Nat. Rev. Immunol.,* 11:823-836, 2011.
Ng et al., "Data storage using peptide sequences", *Nature communications,* 12(1):4242, 2021.
Nguyen et al., "Butelase-mediated cyclization and ligation of peptides and proteins", *Nat Protoc.,* 11: 1977-1988, 2016.
Niall et al., "[36] Automated edman degradation: The protein sequenator," *Methods in Enzymology* 27, 942-1010, 1973.
Nikon., Nikon microscopes educational literature, www.microscopyu.coru/references/photobleaching.html, 2010.
Nivala et al., "Unfoldase-mediated protein translocation through an α-hemolysin nanopore," *Nature Biotechnology,* 31(3):247-250, 2013.
Nuijens et al., "Improved solid phase synthesis of peptide carboxyamidomethyl (Cam) esters for enzymatic segment condensation", *Tetrahedron Letters,* 57(32): 3635-3638, 2016.
Office Communication issued in GB1322371.4, dated Jul. 29, 2019.
Office Communication issued in GB1322371.4, dated Nov. 8, 2019.
Office Communication issued in GB1322371.4, dated Nov. 26, 2018.
Office Communication issued in GB1912227.4, dated Nov. 11, 2019.
Oquare et al., *Design and synthesis of peptide nucleic acid (PNA) agents for imaging gene expression,* in Department of Chemistry, Washington University, 2007.
Ortiz et al., "Design of multivalent fluorescent dendritic probes for site-specific labeling of biomolecules," *Journal of Polymer Science, Part A: Polymer Chemistry,* 56:1609-1616, 2018.
PCT International Search Report and Written Opinion issued in International Application No. PCT/US21/18535, dated Jul. 1, 2021.
PCT International Search Report and written opinion issued in International Application No. PCT/US19/46507, dated Dec. 10, 2019.
PCT International Search Report and written opinion issued in International Application No. PCT/US2019/042998 ,dated Oct. 31, 2019.
PCT International Search Report of International Application No. PCT/US2012/043769 dated Oct. 4, 2012.
PCT/US2015/050099 International Search Report and Written Opinion dated Apr. 11, 2016.
PCT/US2019/041562 International Search Report and Written Opinion dated Oct. 11, 2019.
PCT/US2019/054702 International Search Report and Written Opinion dated Feb. 6, 2020.
PCT/US2021/027155 International Search Report and Written Opinion dated Oct. 14, 2021.
PCT/US2021/033077 International Search Report and Written Opinion dated May 18, 2022.
Penrose, *Random geometric graphs.* (Oxford University Press, 2003).
Peplow et al., "Molecular data-storage system encodes information with peptides," *Chemical and Engineering News,* 2019.
Perron et al., "Derivatives of 6-aminopenicillanic acid. II. Reactions with isocyanates, isothiocyanates, and cyclic anhydrides," *Journal of Organic Chemistry,* 26(9):3365-3367, 1961.
Peschke et al., "Controlled coupling of peptides at their C-termini", *Peptides,* 30: 689-698, 2009.
Peters et al., "A novel multifunctional labeling reagent for enhanced protein characterization with mass spectrometry", *Rapid Commun Mass Spectrom.,* 15(24):2387-92, 2001.

(56) References Cited

OTHER PUBLICATIONS

Petersdorf et al., "16th IHIW: international histocompatibility working group in hematopoietic cell transplantation." *International journal of immunogenetics*, 40(1): 2-10, 2013.
Pham et al., "An Update on Immunotherapy for Solid Tumors: A Review", *Ann Surg Oncol.*, 25(11):3404-3412, 2018.
Phatnani et al., "Phosphorylation and functions of the RNA polymerase II CTD", *Genes Dev.*, 20(21):2922-36, 2006.
Pickens et al., "Practical considerations, challenges, and limitations of bioconjugation via azide-alkyne cycloaddition," *Bioconj. Chem.*, 29(3):686-701, 2018.
Pieroni et al., "Reaction of diazonium salt with tyrosine residues in polypeptides," *Die Makromolekulare Chemie*, 176(11):3201-3209, 1975.
Pirrung et al., "How to make a DNA chip", *Angew. Chem. Int. Ed.* 41:1276-1289, 2002.
Powell and Tempst, "Microflow-based automated chemistries: application to protein sequencing," *Anal. Chem.*, 73(4):776-786, 2001.
Previero et al., "Solid phase sequential analysis: Specific linking of acidic peptides by their carboxyl ends to insoluble resins," *FEBS Letters*, 33(1):135-138, 1973.
Prosenz et al., "Glycated hemoglobin concentrations of red blood cells minimally increase during storage under standard blood banking conditions," *Transfusion*, 59(2):454-457, 2019.
Prudent et al., "Proteomics of stored red blood cell membrane and storage-induced microvesicles reveals the association of flotillin-2 with band 3 complexes," *Front. Physiol.*, 9:421, 2018.
Purushottam et al., "Single-site glycine-specific labeling of proteins", *Nat Commun.*, 10, 2539, 2019.
Quick et al., SITS Derivatization of Peptides to Enhance 266 nm Ultraviolet Photodissociation (UPVD), Journal of the American Society for Mass Spectrometry, 28(7): 1462-1472, 2017.
Rauniyar et al., "Isobaric Labeling-Based Relative Quantification in Shotgun Proteomics", *J. Proteome Res.*, 13: 5293-5309, 2014.
Restrepo-Pérez et al., "Paving the way to single-molecule protein sequencing", *Nat. Nanotechnol.*, 13:786-796, 2018.
Robbins et al., "A pilot trial using lymphocytes genetically engineered with an NY-ESO-1-reactive T-cell receptor: long-term follow-up and correlates with response", *Clin Cancer Res.*, 21(5):1019-27, 2015.
Romond et al., "Trastuzumab plus adjuvant chemotherapy for operable HER2-positive breast cancer," *New England Journal of Medicine*, 353(16):1673-1684, 2005.
Roper Scientific, Datasheet for 1-pentarnax camera, www.spectracore.coru/cameras/pdf/ipgeniii.pdf, 2015.
Rosenbaum et al., "Solid phase synthesis of cyclic peptides by oxidative cyclative cleavage of an aryl hydrazide linker-synthesis of stylostatin 1," *Tetrahedron Letters*, 42:5677-5680, 2001.
Rothbauer et al., "Speed up to find the right ones: rapid discovery of functional nanobodies," *Nature structural & molecular biology*, 25(3): 199-201, 2018.
Rutten et al., "Encoding information into polymers," Nature Reviews: Chemistry, 2:365-381, 2018.
Ryazantsev et al., "Two-dye and one-or two-quencher DNA probes for real-time PCR assay: synthesis and comparison with a TaqMan™ probe," *Anal Bioanal Chem.*, 404:59-68, 2012.
Ryšlavá et al., "Effect of posttranslational modifications on enzyme function and assembly", *J Proteomics*, 92:80-109, 2013.
Saiz et al., "Reversible thiazolidine exchange: a new reaction suitable for dynamic combinatorial chemistry", *Org Lett.*, 11(15):3170-3, 2009.
Salehi-Reyhani et al., "A first step towards practical single cell proteomics: a microfluidic antibody capture chip with TIRF detection," *Lab on a Chip*, 11(7):1256-61, 2011.
Saul et al., "Development of a full-length human protein production pipeline," *Protein Science*, 23(8): 1123-1135, 2014.
Sawyers et al., "The cancer biomarker problem," *Nature*, 452(7187):548-552. 2008.

Scangarello et al., "Application of Multivalent Displays on Metalloprotease-Dependent Cleavage of Semaphorin 4D in Synapse Development", in Department of Biochemistry, Brandeis University, 2012.
Schaus et al., "A DNA nanoscope via auto-cycling proximity recording," *Nature Communications*, 8(696):1-9, 2017.
Schmidt et al., "Omniligase-1: a powerful tool for peptide head-to-tail cyclization", *Advanced Synthesis & Catalysis*, 359(12):2050-2055, 2017.
Schmidt et al., "The struggle to do no harm", *Nature*, 552:S74, 2017.
Schnatbaum et al., "The challenge of complexity: Peptide tools for the development of immunotherapies", Poster—*Innovative Peptide Solutions*, 2016.
Schumacher et al., "Neoantigens in cancer immunotherapy", *Science*, 348(6230):69-74, 2015.
Scoffone et al., "Selective modification of the tryptophan residue in peptides and proteins using sulfenyl halides," *Biochemical and Biophysical Research Communications*, 25(2):170-174, 1966.
Scoffone et al., "Sulfenyl halides as modifying reagents for polypeptides and proteins. I. Modification of tryptophan residues," *Biochemistry*, 7(3):971-979, 1968.
Segura et al., "Detection methods for autologous blood doping," *Drug Test. Anal.*, 4(11): 876-881, 2012.
Shendure et al., DNA sequencing at 40: past, present and future, *Nature*, 550:345-353, 2017.
Shi et al., "Single-cell proteomic chip for profiling intracellular signaling pathways in single tumor cells," *PNAS*, 109(2): 419-424, 2012.
Shimabukuro-Vornhagen et al., "Cytokine release syndrome." *Journal for immunotherapy of cancer*, 6(56): 1-15, 2018.
Shimko et al., "Preparing semisynthetic and fully synthetic histones h3 and h4 to modify the nucleosome core", *Methods Mol Biol.*, 981:177-92, 2013.
Sigal et al., Mapping Synaptic Input Fields of Neurons with Super-Resolution Imaging, *Cell*, 163(2):493-505, 2015.
Song et al., "Photobleaching kinetics of fluorescein in quantitative fluorescence microscopy," *Biophysical Journal*, 68(6):2588-2600, 1995.
Soni and Meller., Progress toward ultrafast DNA sequencing using solid-state nanopores, *Clin Chem*, 53: 1996-2001, 2007.
Steen et al., Phosphorylation Analysis by Mass Spectrometry: Myths, Facts, and the Consequences for Qualitative and Quantitative Measurements, *Molecular & Cellular Proteomics*, 5(1):172-181, 2006.
Stevanovic et al., "Multiple Sequence Analysis: Pool Sequencing of Systemic and Natural Peptide Libraries", *Analytical Biochemistry*, 212(1):212-220, 1993.
Stevens et al., "Enhancement of phosphoprotein analysis using a fluorescent affinity tag and mass spectrometry", Rapid Commun Mass Spectrom., 19(15):2157-62, 2005.
Sumaru et al., "Photoresponsive Aqueous Dissolution of Poly(N-Isopropylacrylamide) Functionalized with o-Nitrobenzaldehyde through Phase Transition", *Biomacromolecules*, 19(7):2913-2922, 2018.
Supplemental Search Report issued in European Application No. 15854171.4, dated Feb. 12, 2018.
Supplemental Search Report issued in European Application No. 19834092.9, dated Mar. 18, 2022.
Swaminathan et al., "A theoretical justification for single molecule peptide sequencing," *PloS computational biology*, 11(2): e1004080, 2015.
Swaminathan et al., "Highly parallel single-molecule identification of proteins in zeptomole-scale mixtures", *Nat. Biotechnol.*, Accepted 2018.
Swaminathan et al., "Peptide Fragment Ion Analyser (PFIA): a simple and versatile tool for the interpretation of tandem mass spectrometric data and de novo sequencing of peptides", *Rapid Commun Mass Spectrom.*, 21(18):3033-8, 2007.
Swoboda et al., "Enzymatic oxygen scavenging for photostability without pH drop in single-molecule experiments," *ACS Nano*, 6(7), 2012.
Szymczak et al., "Peptide arrays: development and application," *Anal Chem.*, 90(1): 266-282, 2008.

(56) References Cited

OTHER PUBLICATIONS

Tang et al., "Development and applications of single-cell transcriptome analysis," *Nat Methods.*, 8(4 Suppl):S6-11. doi: 10.1038/nmeth.1557, 2011.
Taylor et al., "Aminopeptidases: structure and function." *FASEB*, 7(2):290-298, 1993.
Tessier et al., "Doubly orthogonal labeling of peptides and proteins," *Chem*, 5(8): 2243-2263, 2019.
Thakur et al., "Deep and highly sensitive proteome coverage by LC-MS/MS without prefractionation," *Molecular & Cellular Proteomics*, 10(8), 2011.
The Scientist Solution Forum, www.scientistsolutions.coru/tl 1153-keratin+contamination.html, 2009.
The University of Cambridge, Michaelis-Menten equation, wwwjmg.ch.cam.ac.uk/tools/magnus/michmenten.html, 2009.
Thermo Scientific, "Thermo Scientific Pierce Cross-Linking Reagents Technical Handbook," 1-48, 2005.
Thoma et al., "The ABRF Edman Sequencing Research Group 2008 Study: investigation into homopolymeric amino acid N-terminal sequence tags and their effects on automated Edman degradation," *J. Biomol. Tech.*, 20(4):216-225, 2009.
Tillberg et al., "Protein-retention expansion microscopy of cells and tissues labeled using standard fluorescent proteins and antibodies," *Nat Biotechnol.*, 34(9):987-92, 2016.
Tokeshi et al., "Single-and countable-molecule detection of non-fluorescent molecules in liquid phase," *J. Luminesce.*, 83 :261-264, 1999.
Toseland et al., "Fluorescent labeling and modification of proteins" *Journal of chemical biology*, 6(3): 85-95, 2013.
Totaro et al., "Systematic Investigation of EDC/sNHS-Mediated Bioconjugation Reactions for Carboxylated Peptide Substrates", *Bioconjug. Chem.*, 27: 994-1004, 2016.
Tsui et al., "Single red blood cell analysis reveals elevated hemoglobin in poikilocytes", *J. of Biomedical Optics*, 25(1):015004, 2020.
Tulla-Puche et al., "The (classic concept of) solid support," in the power of functional resins in organic synthesis (Tulla-Puche, J., et al., Eds.), 3-14, Wiley, Weinheim, 2008.
Tung et al., "Preparation of a cathepsin D sensitive near-infrared fluorescence probe for imaging," *Bioconjugate Chemistry*, 10(5): 892-896, 1999.
Tyler et al., "Evaluation of Oxford Nanopore's MinION sequencing device for microbial whole genome sequencing applications," *Sci. Rep.*, 8(1):10931, 2018.
U.S. Appl. No. 14/128,247 Notice of Allowance dated Dec. 6, 2016.
U.S. Appl. No. 14/128,247 Office Action dated Mar. 9, 2016.
U.S. Appl. No. 14/128,247 Office Action dated Oct. 28, 2015.
U.S. Appl. No. 15/461,034 Notice of Allowance dated Apr. 26, 2021.
U.S. Appl. No. 15/461,034 Office Action dated Jun. 29, 2018.
U.S. Appl. No. 15/461,034 Office Action dated May 8, 2020.
U.S. Appl. No. 15/461,034 Office Action dated Nov. 20, 2018.
U.S. Appl. No. 15/510,962 Notice of Allowance dated Sep. 11, 2019.
U.S. Appl. No. 15/510,962 Office Action dated Dec. 6, 2018.
U.S. Appl. No. 15/510,962 Office Action dated May 3, 2019.
U.S. Appl. No. 16/572,194 Final Office Action dated Mar. 19, 2021.
U.S. Appl. No. 16/572,194 Notice of Allowance dated Jul. 15, 2021.
U.S. Appl. No. 16/572,194 Notice of Allowance dated Jun. 30, 2021.
U.S. Appl. No. 16/572,194 Office Action dated Aug. 17, 2020.
U.S. Appl. No. 16/709,903 Final Office Action dated Jul. 8, 2021.
U.S. Appl. No. 16/709,903 Non Final Office Action dated Jan. 27, 2022.
U.S. Appl. No. 16/709,903 Office Action dated Dec. 30, 2020.
U.S. Appl. No. 16/709,903 Office Action dated Feb. 5, 2020.
U.S. Appl. No. 16/709,903 Office Action dated Jul. 16, 2020.
U.S. Appl. No. 17/491,797 Corrected Notice of Allowance dated Apr. 20, 2022.
U.S. Appl. No. 17/491,797 Non Final Office Action dated Jan. 27, 2022.
U.S. Appl. No. 17/491,797 Notice of Allowance dated Apr. 8, 2022.
Ulbrich et al., "Subunit counting in membrane-bound proteins," *Nature Methods*, 4(4):319-321, 2007.
Valeur et al., Molecular Fluorescence: Principles and Applications. Wiley-VCH:2002.
Villain et al., Chemical Ligation of Multiple Peptide Fragments Using a New Protection Strategy, *Chemistry & Biology*, 8(7):673-679, 2001.
Vitiello et al., "Neoantigen prediction and the need for validation", *Nat Biotechnol.*, 35(9):815-817, 2017.
Volkmann et al., "Protein C-terminal labeling and biotinylation using synthetic peptide and split-intein," *PLoS ONE*, 4(12): e8381, 2009.
Wainaina et al., "Fluorescence detection of amino acids in the postcleavage conversions for manual sequencing of a peptide," *Analytical Biochemistry*, 374(2), 423-425, 2008.
Waliczek et al., "Peptides Labeled with Pyridinium Salts for Sensitive Detection and Sequencing by Electrospray Tandem Mass Spectrometry", *Sci Rep.*, 6:37720, 2016.
Wan et al., "Panorama of ancient metazoan macromolecular complexes," *Nature*, 525:339-344, 2015.
Wang et al., "The covalent trimethoprim chemical tag facilitates single molecule imaging with organic fluorophores," *Biophysical Journal*, 106(1):272-278, 2014.
Weeks et al., "Subtiligase-catalyzed peptide ligation", *Chem. Rev.*, 120(6): 3127-3160, 2019.
Wiese et al., "Protein labeling by iTRAQ: a new tool for quantitative mass spectrometry in proteome research", *Proteomics*, 7(3):340-50, 2007.
Williamson et al., "Efficient N-terminal labeling of proteins by use of sortase", *Angew Chem Int Ed Engl.*, 51(37):9377-80, 2012.
Wittmann et al., "Combinatorial Solid-Phase Synthesis of Multivalent Cyclic Neoglycopeptides," *Angewandte Chemie International Edition*, 39(23): 4348-4352, 2000.
Wu et al., "Versatile Peptide C-Terminal Functionalization via a Computationally Engineered Peptide Amidase", *ACS Catal.* 6: 5405-5414, 2016.
Xu et al., "Chemoenzymatic labeling of protein C-termini for positive selection of C-terminal peptides," *ACS Chem. Biol.*, 6(10):1015-1020, 2011.
Yadav et al., "Predicting immunogenic tumour mutations by combining mass spectrometry and exome sequencing", *Nature*, 515:572-576, 2014.
Yang et al., "Single-cell, multiplexed protein detection of rare tumor cells based on a beads-on-barcode antibody microarray," *Analytical chemistry*, 88 (22):11077-11083, 2016.
Yee et al., Endogenous T-Cell Therapy: Clinical Experience, *Cancer J.*, 21(6):492-500, 2015.
Yee et al., Personalized Therapy: Tumor Antigen Discovery for Adoptive Cellular Therapy, *Cancer J.*, 23(2):144-148, 2017.
Yewdell et al., "Making sense of mass destruction: quantitating MHC class I antigen presentation", *Nat Rev Immunol.*, 3(12):952-61, 2003.
Yuan et al., "A rational approach to tuning the p K a values of rhodamines for living cell fluorescence imaging," *Organic & Biomolecular Chemistry*, 9(6):1723-1726, 2011.
Zervas et al., "New methods in peptide synthesis. I. Tritylsulfenyl and o-nitrophenylsulfenyl groups as N-protecting groups," *Journal of the American Chemical Society*, 85(22):3660-3666, 1963.
Zhang et al., "Thiol specific and tracelessly removable bioconjugation via Michael addition to 5-methylene pyrrolones," *J. Am. Chem. Soc.*, 139(17):6146-6151, 2017.
Zhao et al., "Single-molecule spectroscopy of amino acids and peptides by recognition tunnelling," *Nature Nanotechnology*, 9(6): 466-473, 2014.
Zheng et al., "The contribution of reactive oxygen species to the photobleaching of organic fluorophores," *Photochemistry and Photobiology*, 90(2):448-454, 2014.
Zheng et al., "Ultra-stable organic fluorophores for single-molecule research," *Chemical Society Reviews*, 43(4):1044-1056, 2014.

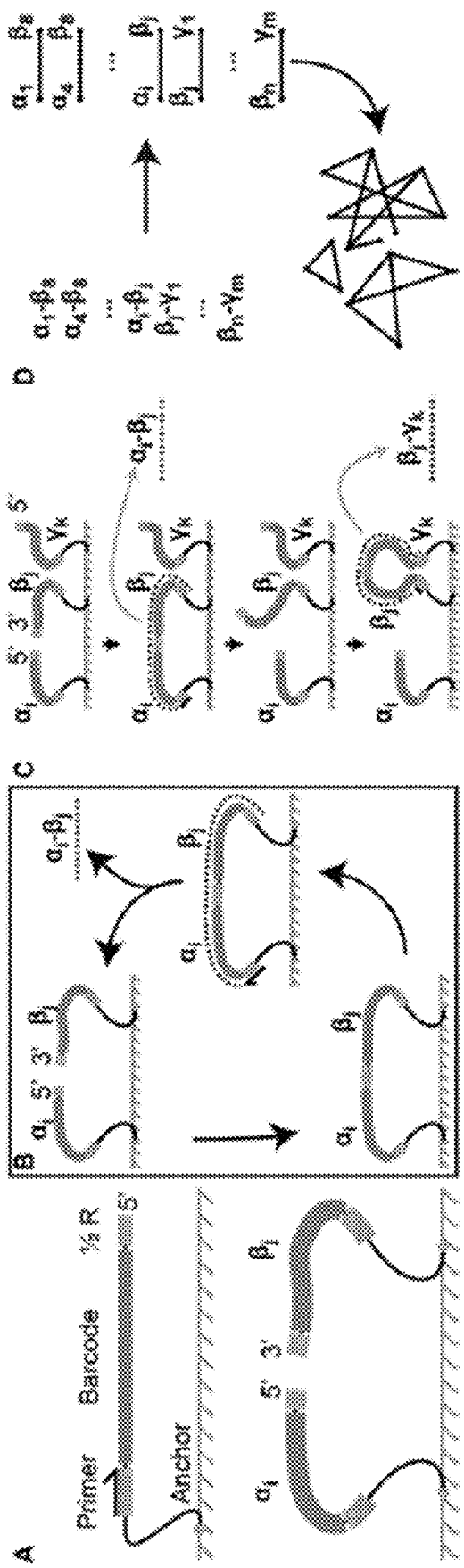
FIGS. 1A-D

Original positions
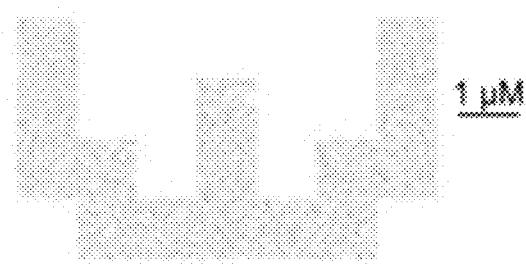
Kamada-Kawai layout recovery of positions
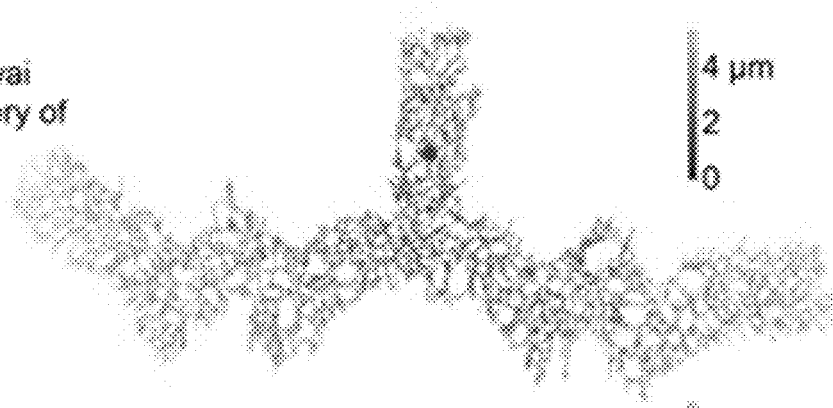
Kamada-Kawai layout recovery of positions with correction
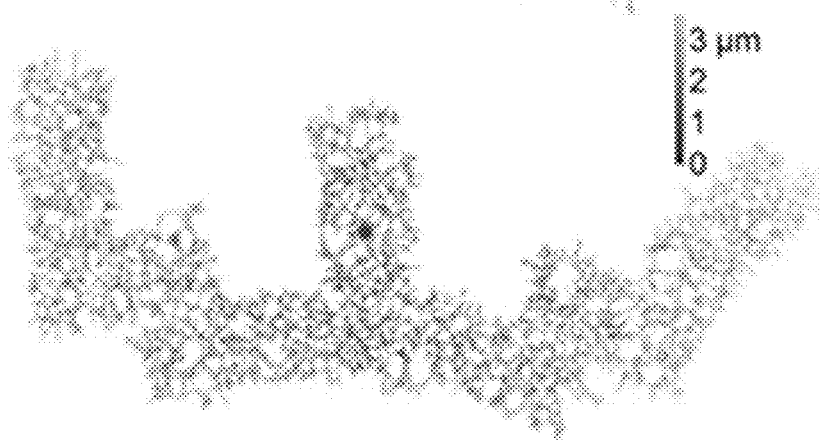
FIG. 3

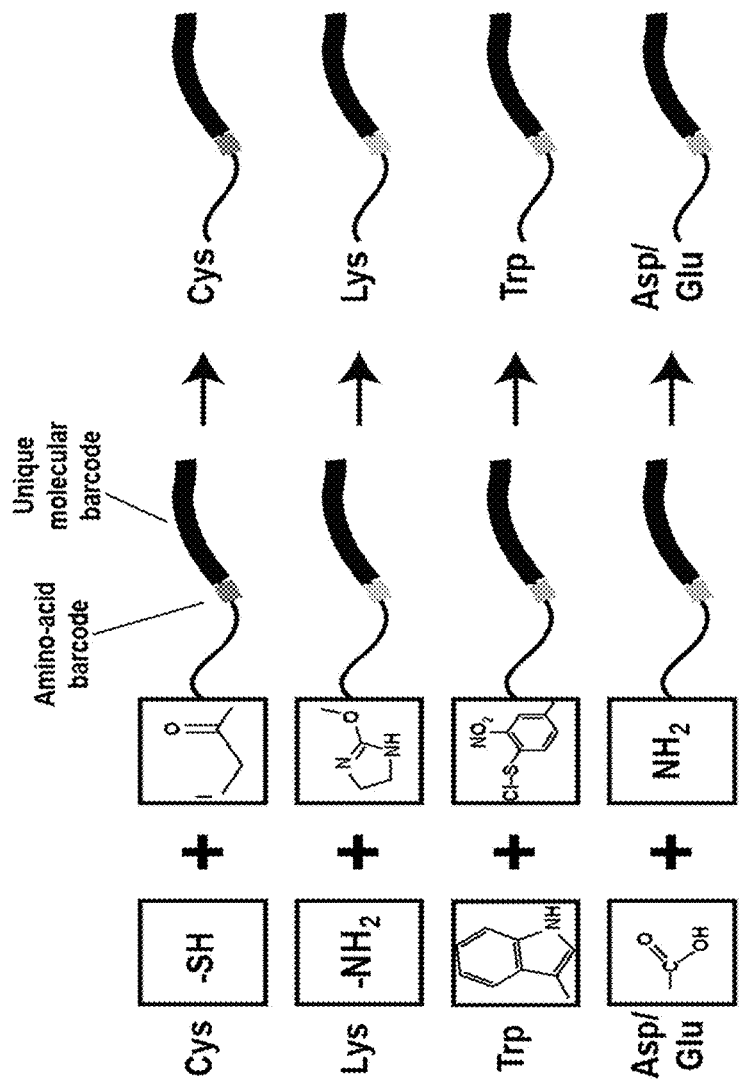
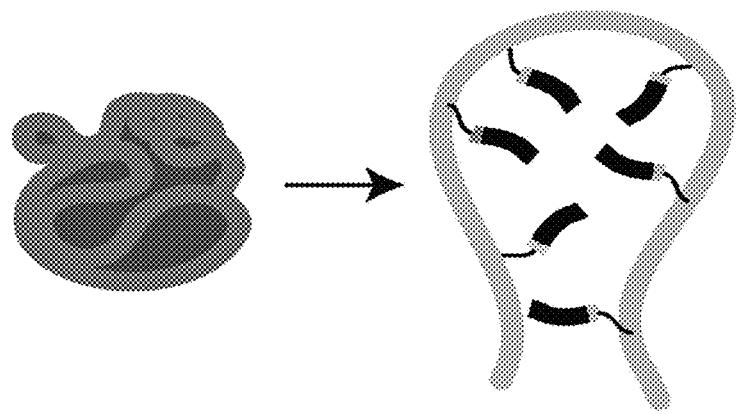
FIGS. 4A-B

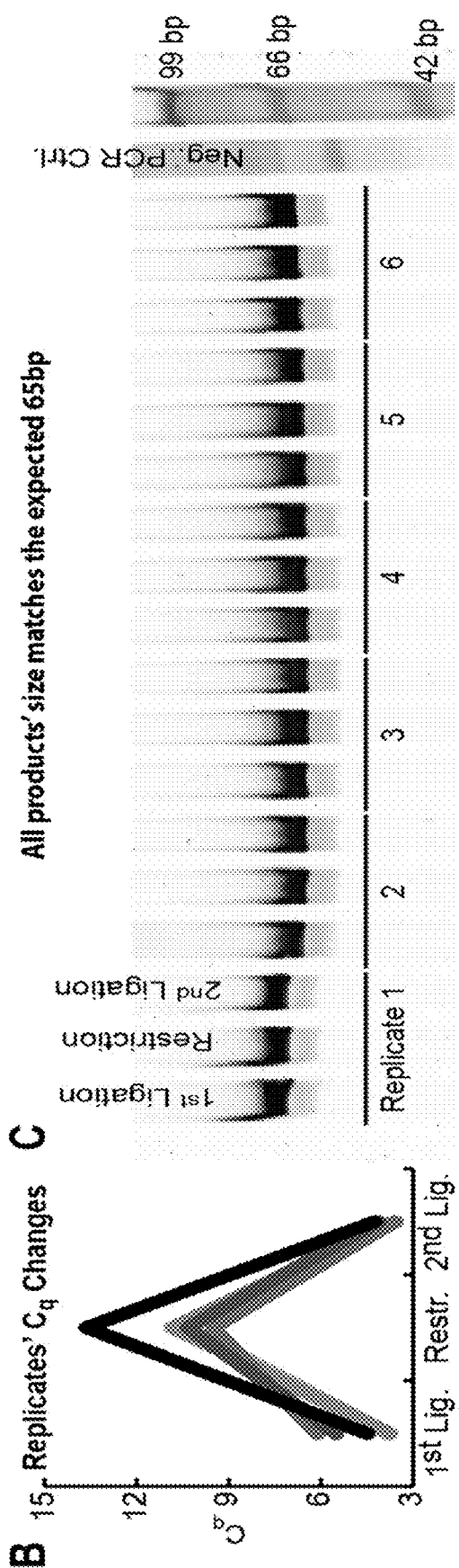
FIGS. 7B-C

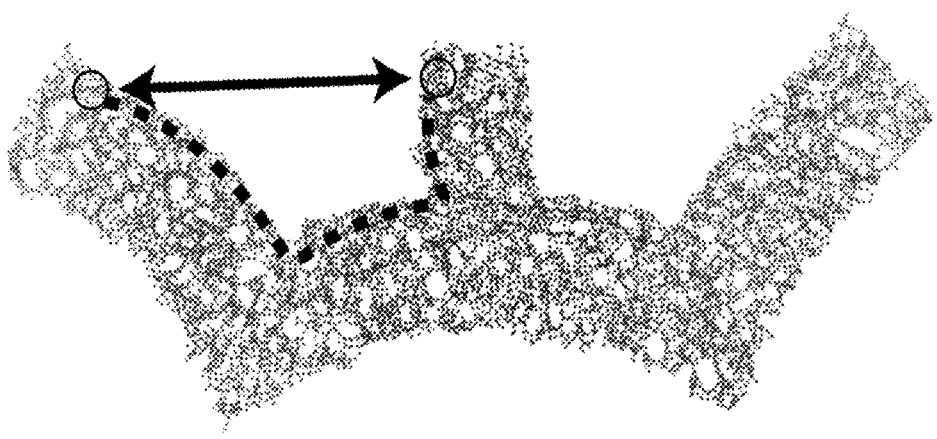
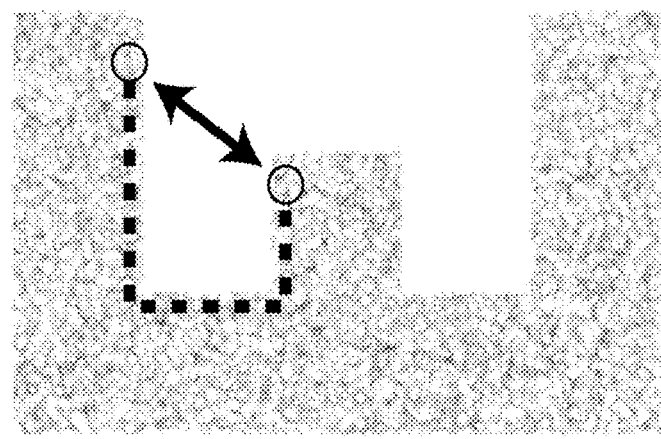
FIG. 9

| Original positions | Kamada-Kawai | Kamada-Kawai with correction |
|---|---|---|
| 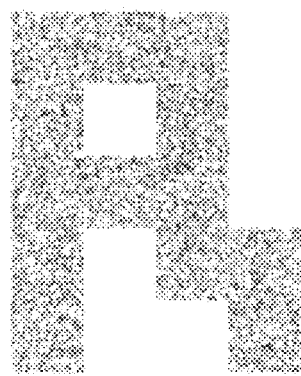 | 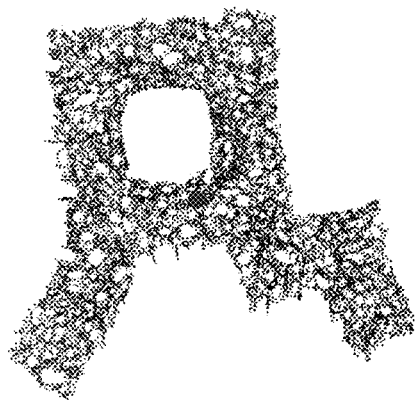 | 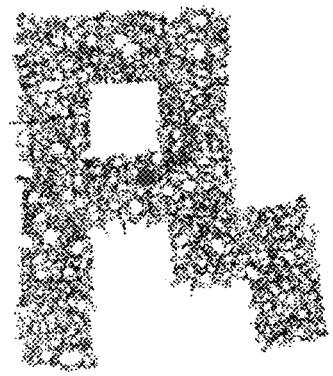 |
| 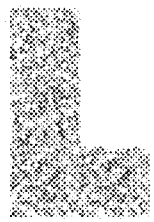 1 μM | 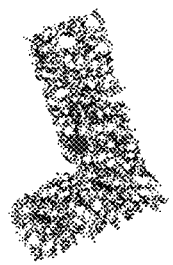 |  |
| 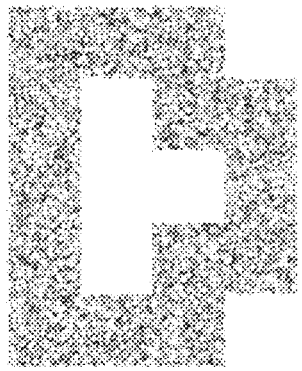 | 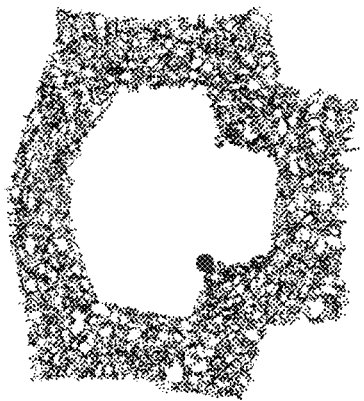 | 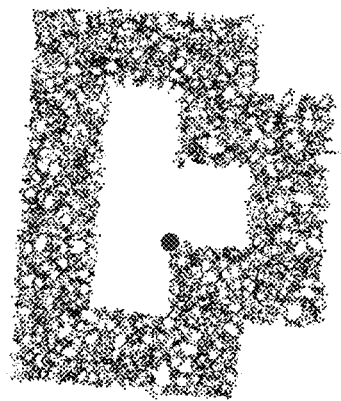 |
FIG. 10A (cont.)

Original positions     Kamada-Kawai     Kamada-Kawai with correction
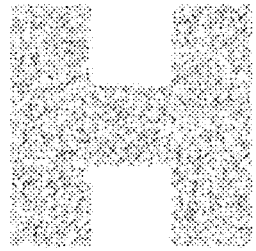
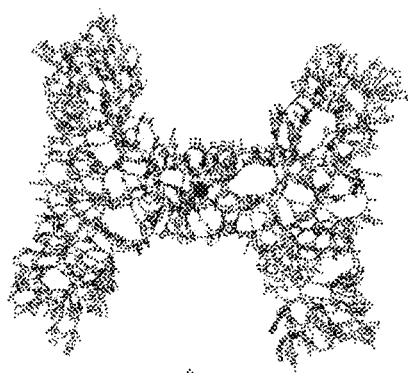
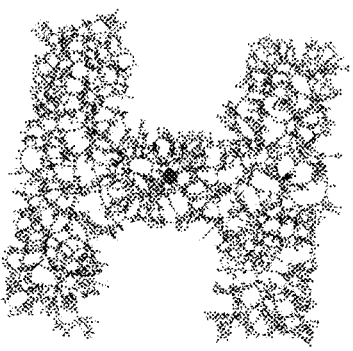
1 μM
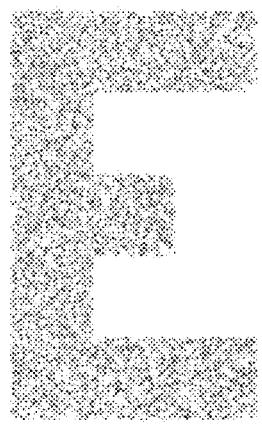
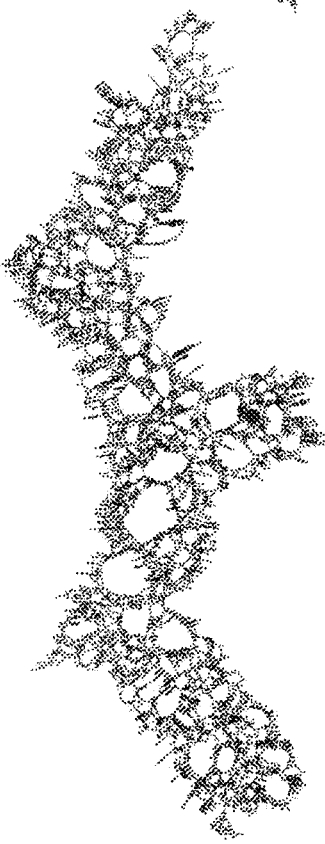
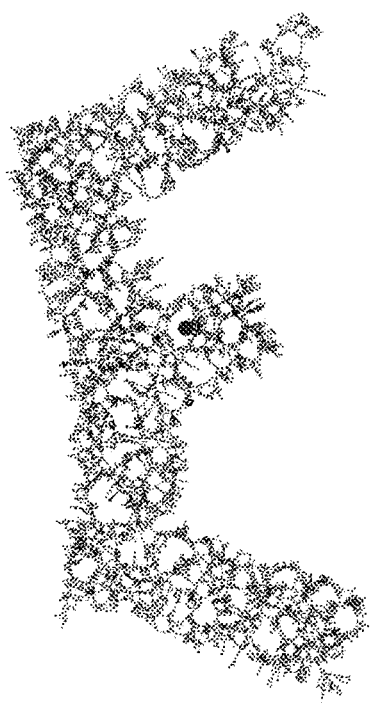
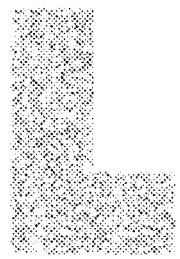
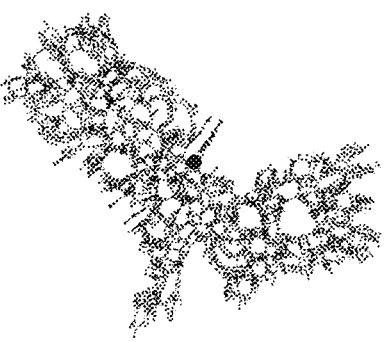
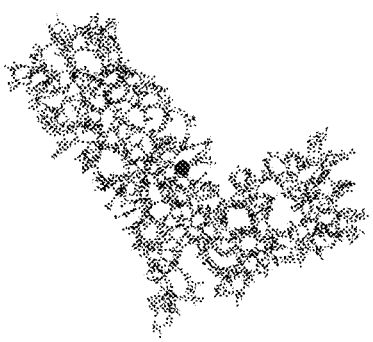
FIG. 10B

| Original positions | Kamada-Kawai | Kamada-Kawai with correction |
|---|---|---|
| 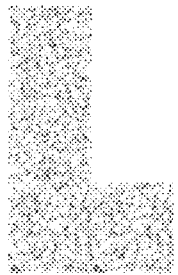 |  | 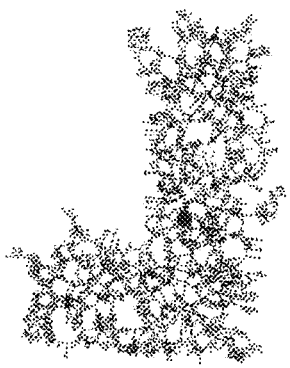 |
| 1 μM | | |
| 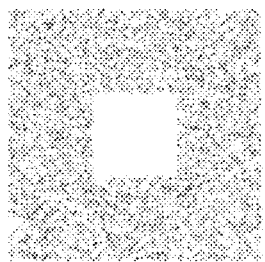 | 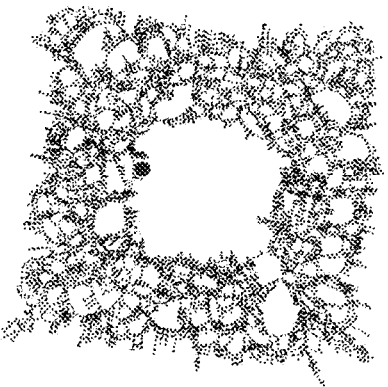 | 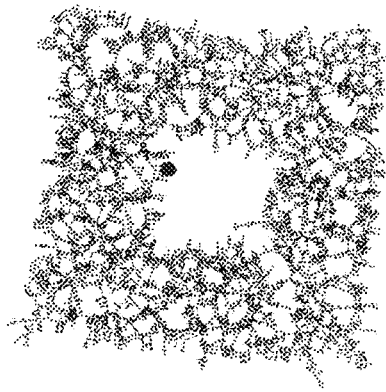 |
| 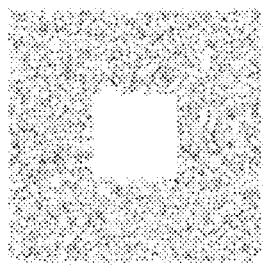 | 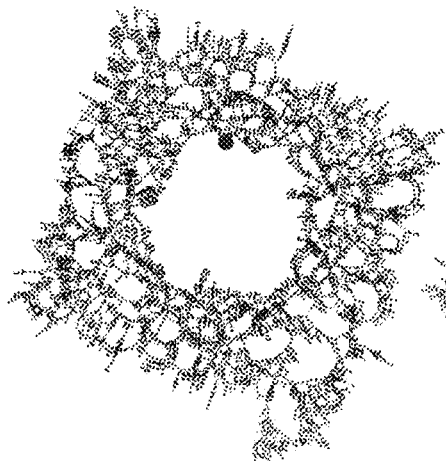 | 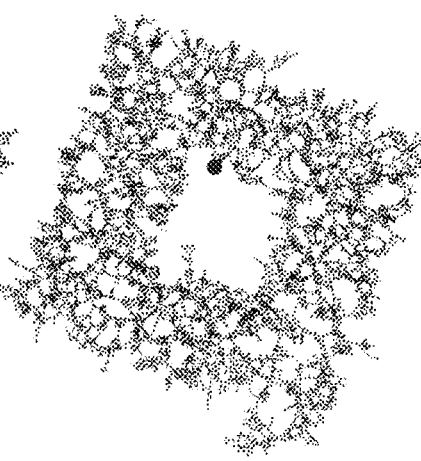 |
FIG. 10B (cont.)

| Original positions | Kamada-Kawai | Kamada-Kawai with correction |
|---|---|---|
| 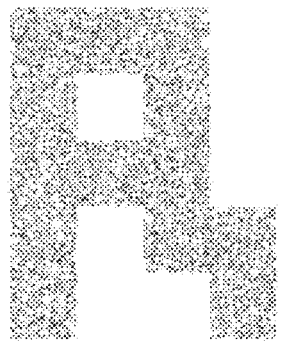 | 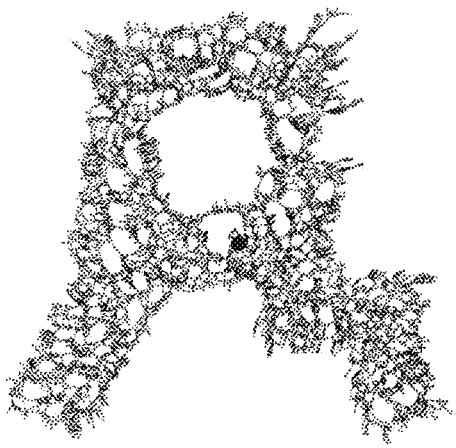 | 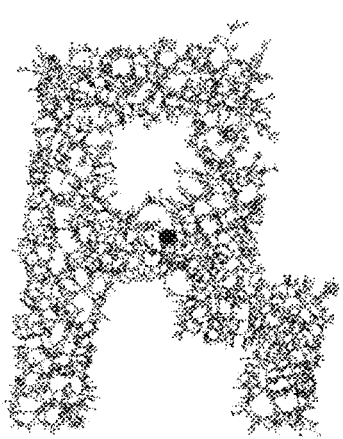 |("1 μM" scale bar)
|  | 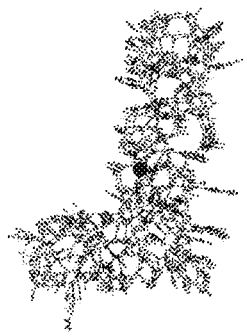 |  |
| 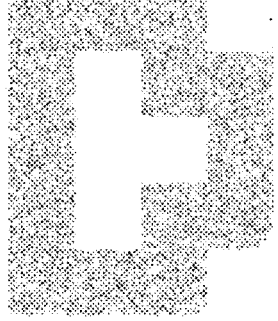 | 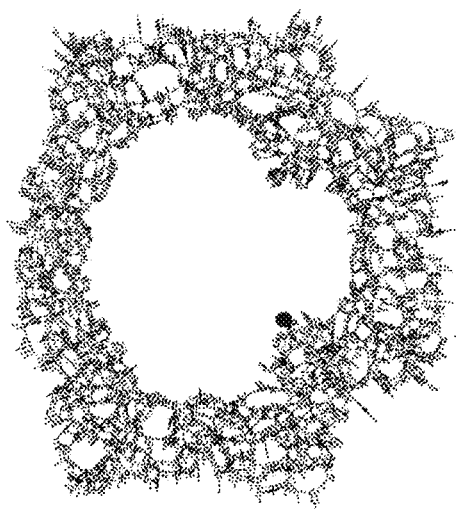 | 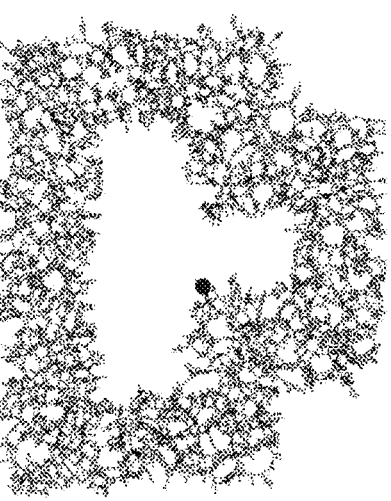 |
FIG. 10B (cont.)

5' hexynyl oligo:

5'-/5Hexynyl/CAG ACG TGT GCT CTT CCG ATC T TC AGC TGA T CG AAT GAG TAT GCC T -3'

Barcodes, with bridging and blocking oligos, and primers:

Round 1 linker        3'-/3InvdT/ GC TTA CTC ATA CGG A ACG GAG CTA GTA CCC-5'
Round 1 barcode       5'-/5Phos/ACG GAG CTA GTA CCC [UMI x 5] [BC x 10] GTT CAT ACG TCG CGC-3'
Round 1 blocker-3InvdT 5'-CG AAT GAG TAT GCC T TGC CTC GAT CAT GGG /3InvdT/-3'

Round 2 linker        3'-/3InvdT/ GTT CAT ACG TCG CGC AAG TAT CTC GGA CTA-5'
Round 2 barcode       5'-/5Phos/AAG TAT CTC GGA CTA [UMI x 5] [BC x 10] TCA GCA TGT AGT ACG-3'
Round 2 blocker       5'-CAA GTA TGC AGC GCG TTC ATA GAG CCT GAT /3InvdT/-3'

Round 3 linker        3'-/3InvdT/ TCA GCA TGT AGT ACG AGA TCA GTG ACA GTG-5'
Round 3 barcode       5'-/5Phos/AGA TCA GTG ACA GTG [BC x 10] G TAT ACC AGT TGA GAC GCA ACT ATG GTG ACG AA -3'
Round 3 blocker       5'-AGT CGT ACA TCA TGC TCT AGT CAC TGT CAC /3InvdT/-3'

Forward primer        5'-CAG ACG TGT GCT CTT CCG ATC T-3'
Reverse primer        5'-TT CGT CAC CAT AGT TGC GTC TCA-3'

Final expected ligation product:

Hexynyl oligo + Round 1-barcode + Round 2-barcode + Round 3-barcode

5'- GTC TGC ACA CGA GAA GGC TAG A AG TCG ACT A GC TTA CTC ATA CGG A ACG GAG CTA GTA CCC [UMI x 5] [BC x 10] GTT CAT ACG
TCG CGC AAG TAT CTC GGA CTA [UMI x 5] [BC x 10] TCA GCA TGT AGT ACG AGA TCA GTG ACA GTG [BC x 10] G TAT ACC AGT TGA GAC
GCA ACT ATG GTG ACG AA -3'

FIG. 12B

Round 1
/5Phos/TGC CTC GAT CAT GGG NNNNN AAC AAC AAC C CAA GTA TGC AGC GCG
/5Phos/TGC CTC GAT CAT GGG NNNNN AAC TCT CGC C CAA GTA TGC AGC GCG
/5Phos/TGC CTC GAT CAT GGG NNNNN ACA GTT ATG C CAA GTA TGC AGC GCG
/5Phos/TGC CTC GAT CAT GGG NNNNN AGC TAC CAT G CAA GTA TGC AGC GCG
/5Phos/TGC CTC GAT CAT GGG NNNNN ATA AGA GCA C CAA GTA TGC AGC GCG
/5Phos/TGC CTC GAT CAT GGG NNNNN CCA CTC GAA C CAA GTA TGC AGC GCG
/5Phos/TGC CTC GAT CAT GGG NNNNN CGA GAA GGA A CAA GTA TGC AGC GCG
/5Phos/TGC CTC GAT CAT GGG NNNNN CTC TAT ACA C CAA GTA TGC AGC GCG
/5Phos/TGC CTC GAT CAT GGG NNNNN GTA GAA TCC T CAA GTA TGC AGC GCG
/5Phos/TGC CTC GAT CAT GGG NNNNN TCC TTA ATC C CAA GTA TGC AGC GCG
Round 2
/5Phos/TTC ATA GAG CCT GAT NNNNN AAC AAG GTG G AGT CGT ACA TCA TGC
/5Phos/TTC ATA GAG CCT GAT NNNNN AAG ACT GAG A AGT CGT ACA TCA TGC
/5Phos/TTC ATA GAG CCT GAT NNNNN ACC GCA AGA C AGT CGT ACA TCA TGC
/5Phos/TTC ATA GAG CCT GAT NNNNN AGG AAT TGC C AGT CGT ACA TCA TGC
/5Phos/TTC ATA GAG CCT GAT NNNNN ATC TTG GAG T AGT CGT ACA TCA TGC
/5Phos/TTC ATA GAG CCT GAT NNNNN CCG GTA GTT C AGT CGT ACA TCA TGC
/5Phos/TTC ATA GAG CCT GAT NNNNN CGG ACA CCT A AGT CGT ACA TCA TGC
/5Phos/TTC ATA GAG CCT GAT NNNNN GAG GTT CAG C AGT CGT ACA TCA TGC
/5Phos/TTC ATA GAG CCT GAT NNNNN GTC CAC AGC T AGT CGT ACA TCA TGC
/5Phos/TTC ATA GAG CCT GAT NNNNN TGG TGC ATA A AGT CGT ACA TCA TGC
Round 3
/5Phos/TCT AGT CAC TGT CAC AAC CGA TTC C ACT CTG CGT TGA TAC CAC TGC TT
/5Phos/TCT AGT CAC TGT CAC AAT GGT AAC G ACT CTG CGT TGA TAC CAC TGC TT
/5Phos/TCT AGT CAC TGT CAC ACG CCT CTT A ACT CTG CGT TGA TAC CAC TGC TT
/5Phos/TCT AGT CAC TGT CAC AGT GTG GTC C ACT CTG CGT TGA TAC CAC TGC TT
/5Phos/TCT AGT CAC TGT CAC CAA TAC GTC C ACT CTG CGT TGA TAC CAC TGC TT
/5Phos/TCT AGT CAC TGT CAC CCT CAT TGT C ACT CTG CGT TGA TAC CAC TGC TT
/5Phos/TCT AGT CAC TGT CAC CTA GCG CGT T ACT CTG CGT TGA TAC CAC TGC TT
/5Phos/TCT AGT CAC TGT CAC GCG TCG TGA A ACT CTG CGT TGA TAC CAC TGC TT
/5Phos/TCT AGT CAC TGT CAC GTT ACT CGG T ACT CTG CGT TGA TAC CAC TGC TT
/5Phos/TCT AGT CAC TGT CAC TTC GAT GCG G ACT CTG CGT TGA TAC CAC TGC TT

FIG. 14A

KCDYWEC

```
Reference
5'-CAG ACG TGT GCT CTT CCG ATC T TC AGC TGA T CG AAT GAG TAT GCC T TGC CTC GAT CAT GGG [UMI x 5] [BC x 10] CAA GTA TGC
AGC GCG TTC ATA GAG CCT GAT [UMI x 5] [BC x 10] AGT CGT ACA TCA TGC TCT AGT CAC TGT CAC [BC x 10] ACT CTG CGT TGA TAC CAC
TGC TT-3'

Actual sequence using Forward primer MATCHES
NNNNNNNNNNNNNNNNNNNCT TGC CTC GNT CAT GGG TGN NN NAN AAN NNC CAA GTA TGC AGC GCG TTC ATA GAG CCT GAT NGG NG ANG ANA NGN
N AGT CGT ACA TCA TGC TCT AGT CAC TGT CAC CNN NNN NNN N ACT CTG CGT TGA TAC CAC T NNTTNNNAN Reference reverse compliment
5'-AA GCA GTG GTA TCA ACG CAG AGT [BC x 10] GTG ACA GTG ACT AGA GCA TGA TGT ACG ACT [BC x 10] [UMI x 5] ATC AGG CTC TAT
GAA CGC GCT GCA TAC TTG [BC x 10] [UMI x 5] CCC ATG ATC GAG GCA A GGC ATA CTC ATT CG A TCA GCT GA A GAT CGG AAG AGC ACA
CGT CTG-3'

Actual sequence using Reverse primer MATCHES
NNNNNNNNNNNNNNGNNT AGA GCN TGA TGT ACG ACT GNN GTN NCN N NNC NNN ATC AGG CTC TAT GAA CGC GCT GCA TAC TTG GNN NNN CTG N
CCN NN CCC ATG ATC GAG GCA A GGC ATA CTC ATT CG A TCA GCT GA A GAT CGG AAG AGC ACA CGT CTG N
```

MOLECULAR NEIGHBORHOOD DETECTION BY OLIGONUCLEOTIDES

This application is a continuation of International Application No. PCT/US2019/041562, filed Jul. 12, 2019, which claims the benefit of U.S. Provisional Patent Application No. 62/697,179, filed Jul. 12, 2018, the entire contents of each of which is incorporated herein by reference in their entirety.

This invention was made with government support under Grant no. OD009572 and R35 GM122480 awarded by the National Institutes of Health and Grant no. N66001-14-2-4051 awarded by the Space and Naval Warfare Systems Center, Pacific. The government has certain rights in the invention.

INCORPORATION OF SEQUENCE LISTING

The sequence listing that is contained in the file named "UTSBP1195US.txt", which is 2 KB (as measured in Microsoft Windows) and was created on Jan. 8, 2021, is filed herewith by electronic submission and is incorporated by reference herein.

BACKGROUND

1. Field

The present disclosure relates generally to the fields of chemistry and molecular biology. More particularly, it concerns methods for identifying which molecules share the same neighborhood in space, and the resulting approaches that allow for mapping these molecules positions in space or, in other variations, detecting and identifying molecules using oligonucleotides.

2. Description of Related Art

Aside from carrying genetic information in organisms, DNA has proven utility across a broad field of applications. As the mastery of chemistries and enzymes to manipulate DNA has deepened, so has the breadth of its utility. One of the most powerful developments contributing to this trend has been the rapid growth in high-throughput DNA sequencing (Shendure et al., 2017), now providing a remarkable stream of new information about the world.

DNA barcoding—the incorporation of specific, pre-designed DNA sequences into molecules as an approach to identify them or copies of them across experiments—has been a key innovation for accelerating the throughput of sequencing (Buschmann and Bystrykh, 2013) and as such sits at an interesting intersection of biology and information theory. The most basic application of DNA barcoding is to label and thus track individual molecules as they are manipulated. This concept has been expanded to obtain information beyond tracking particle identities, for example to identifying their interaction partners (Soderberg et al., 2017) and spatial positions (Schaus et al., 2017). However, there is an unmet need for improved methods of detecting single molecules, such as proteins or peptides, by using the spatial positions of the molecules.

SUMMARY

In certain embodiments, the present disclosure provides methods of interrogating molecular neighborhoods. A sample of dilute proteins can be interrogated for positional information, such as by two-round techniques including iterative proximity ligation (IPL) or split-and-pool labeling, using oligonucleotide probes. The IPL method can be used to define a neighborhood by wherever an oligonucleotide probe can reach while the split-and-pool method can be used to define the neighborhood by a set of oligonucleotides linked to each other through a physical intermediate.

In one embodiment, there is provided a method for performing iterative proximity ligation (IPL) comprising attaching oligonucleotide tags (e.g., deoxyribonucleic acid (DNA) tags) to a plurality of molecules in a sample, wherein the oligonucleotide tags comprise (1) a functional group for attachment to a molecule, (2) a primer site, (3) a unique barcode, and (4) a 5' cleavage half-site or a 3' cleavage half-site; ligating oligonucleotide tags with a 5' cleavage half-site to oligonucleotide tags with a 3' cleavage half-site which are held in proximity, thereby generating one or more barcode pairs; extending the primer in one of the oligonucleotide tags of the one or more barcode pairs to generate duplicates of the barcode pairs; and adding a catalyst for cleavage to separate the oligonucleotide tags.

In some aspects, the oligonucleotide tags are single-stranded or double-stranded. In certain aspects, the functional group is selected from the group consisting of succinimidyl ester, iodoacetamide, maleimide, amines, 4-phenyl-3H-1,2,4-triazole-3,5(4H)-dione (PTAD), 2,4-dinitrobenzenesulfenyl chloride, and a thiol.

In some aspects, ligating is reversible. In particular aspects, the tags are not conjugated to a fluorescent label. In certain aspects, ligating comprises adding a protein ligase and a bridging oligonucleotide. In some aspects, the protein ligase is a blunt-end ligase. In certain aspects, the protein ligase is T4 DNA ligase, T4 RNA ligase, Taq DNA ligase, T3 DNA ligase, or T7 DNA ligase. In some aspects, ligating comprises chemical ligation. In particular aspects, chemical ligation comprises using click chemistry, carbodiimides, or phosphorothioate-iodide coupling.

In certain aspects, the bridging oligonucleotide comprises a first region of complementarity to the tag with the 5' cleavage half-site and a second region of complementarity to the tag with the 3' cleavage half-site. In some aspects, the catalyst for cleavage is a sequence-specific endonuclease. In certain aspects, the sequence-specific endonuclease is a restriction enzyme, zinc finger nuclease, sequence-specific ribozyme, or CRISPR-associated endonuclease. In some aspects, the catalyst for cleavage is an oligonucleotide modified with a chemical cleavage reagent. In certain aspects, the chemical cleavage agent is iron:EDTA. In some aspects, the oligonucleotide tags with the 5' cleavage half-site and oligonucleotide tags with the 3' cleavage half-site are added to the sample at a 1:1 ratio before attaching the oligonucleotide tags.

In some aspects, a round of IPL generates multiple barcode pairs. In particular aspects, each round of IPL generates at least $2\times10^{10}$ (e.g., at least $2\times10^{11}$, $2\times10^{12}$, $2\times10^{13}$, or $2\times10^{14}$) duplicate barcode pairs.

In additional aspects, the method further comprises performing at least one additional round of IPL on said sample to obtain multiple duplicate barcode pairs. In particular aspects, 2, 3, 4, 5, or more rounds of IPL are performed. In particular aspects, the one or more rounds of IPL are performed in a single reaction tube.

In some aspects, the molecule is a protein, protein complex, peptide, antibody, carbohydrate, nucleic acid, cell or a receptor. In certain aspects, IPL is performed on a molecular surface or in solution. In some aspects, the molecular surface is organic or inorganic. In specific aspects, the molecular surface comprises crystals, plastic, or metal. In particular aspects, the cell is a mammalian cell, cancer cell, or cell infected with an infectious agent. In certain aspects, the infectious agent is HIV.

In additional aspects, the method further comprises amplifying the duplicate barcode pairs. In some aspects, amplifying comprises performing polymerase chain reaction (PCR). In some aspects, the method further comprises performing sequencing on the duplicate barcode pairs. In certain aspects, the method further comprises identifying and quantifying one or more molecules in the sample. In certain aspects, identifying and quantifying comprise generating a graph from the sequence of the duplicated barcode pairs. In some aspects, generating a graph comprises interpreting each barcode as a node and each barcode pair as an edge. In some aspects, the graph positions the molecules in the sample at a at nanometer or micrometer scale. In particular aspects, the method further comprises simulating Erdos-Renyi random graph connectivity, random geometric graph connectivity, or spring-layout algorithms to recover spatial information for one or more molecules in the sample. In certain aspects, the method further comprises applying Graphviz Neato implementation of a Kamada-Kawai algorithm to the spring-layout algorithm. In some aspects, the Kamada-Kawai algorithm is a modified variant that performs local-only spring energy minimization. In certain aspects, the Kamada-Kawai algorithm is applied followed by a second round using the modified Kamada-Kawai algorithm.

In another embodiment, there is provided a composition comprising a oligonucleotide tag comprising (1) a functional group for attachment to the molecule, (2) a primer site, (3) a unique barcode, and (4) a 5' restriction half-site ligated to a oligonucleotide tag comprising (1) a functional group for attachment to the molecule, (2) a primer site, (3) a unique barcode, and (4) a 3' restriction half-site. In some aspects, each of the oligonucleotides tags are attached to a molecule.

In yet another embodiment, there is provided a method of determining the spatial position of an individual molecule(s) comprising obtaining a sample comprising a plurality of individual molecules; applying multiple rounds of IPL according to claim 1 on said sample to generate a plurality of duplicate barcode pairs; performing next-generation sequencing on the plurality of duplicate barcode pairs; and applying pairwise proximity to determine the spatial position of the individual molecule(s).

In some aspects, the sample is a biological sample. In certain aspects, the biological sample is saliva, urine, blood, or whole tissue. In certain aspects, the method does not comprise using microscopy. In certain aspects, the individual molecule is not bound to a solid support.

In some aspects, the molecule is a protein, protein complex, peptide, antibody, carbohydrate, nucleic acid, cell, signaling domain, or a receptor. In certain aspects, the antibody is bound to another antibody or a ligand. In particular aspects, the molecule is a protein or peptide. In specific aspects, the protein or peptide is a biomarker for cancer or an infectious disease. In some aspects, the protein or peptide is in solution. In some aspects, amino acids in the protein or peptide are labeled with amino-acid specific oligonucleotide tags each comprising a unique barcode. In particular aspects, the amino acids are lysine, cysteine, glutamic acid, aspartic acid, tyrosine, tryptophan, histidine, or any combination thereof. In some aspects, the amino acids comprise post-translationally modified side chains. In specific aspects, the post-translationally modified side chains comprise phosphorylation, glycosylation, methylation, citrullination, or any combination thereof.

In additional aspects, the method further comprises determining the identity and quantity of the protein or peptide. In some aspects, determining the identity of the protein or peptide comprises obtaining an amino acid pattern from the next-generation sequencing and comparing the amino acid pattern to the proteome of an organism to identify the protein or peptide.

In particular aspects, the second step is performed in a single reaction tube. In some aspects, the sample comprises from 2 to $10^{12}$ proteins, such as at least 3, 4, 5, 10, 15, 20, 50, 100, 500, $10^3$, $10^4$, $10^5$, $10^6$, $10^7$, $10^8$, $10^9$, $10^{10}$, $10^{11}$, $10^{12}$ or more proteins. In some aspects, the sample is diluted before DNA sequencing.

In additional aspects, the method further comprises digesting the protein with an enzyme. In certain aspects, the enzyme site-specifically digests the protein. In particular aspects, the enzyme is trypsin. In some aspects, the digestion does not remove the N-terminal amino acid.

In some aspects, the method further comprises applying a second set of IPL rounds to the digested protein. In certain aspects, the method further comprises reconciling the duplicate barcode pairs from each set of IPL rounds to identify the protein.

In some aspects, the molecules are nanobeads. In certain aspects, the method further comprises determining the shape and size of the nanobeads.

A further embodiment provides a method of determining the identity of a protein or peptide comprising obtaining a sample comprising a plurality of proteins peptides, or a combination thereof; applying multiple rounds of IPL according to claim 1 on said sample to generate a plurality of duplicate barcode pairs; performing next-generation nucleic acid sequencing on the plurality of duplicate barcode pairs; and obtaining an amino acid pattern for a single protein or peptide from the next-generation nucleic acid sequencing and comparing the amino acid pattern to the proteome of an organism to identify the protein or peptide.

In some aspects, the sample is a biological sample. In certain aspects, the biological sample is saliva, urine, blood, or whole tissue. In certain aspects, the protein or peptide is a biomarker for cancer or an infectious disease.

In certain aspects, the method does not comprise using microscopy. In some aspects, the individual molecule is not bound to a solid support. In certain aspects, the protein or peptide is in solution. In some aspects, amino acids in the protein or peptide are labeled with amino-acid specific oligonucleotide tags each comprising a unique barcode. In particular aspects, the amino acids are lysine, cysteine, glutamic acid, aspartic acid, tyrosine, tryptophan, histidine, or a combination thereof. In specific aspects, the amino acids comprise post-translationally modified side chains. In some aspects, the post-translationally modified side chains comprise phosphorylation, glycosylation, methylation, citrullination, or a combination thereof.

In some aspects, the second step is performed in a single reaction tube. In some aspects, the sample comprises from about 2 to about $10^{12}$ proteins, such as at least 3, 4, 5, 10, 15, 20, 50, 100, 500, $10^3$, $10^4$, $10^5$, $10^6$, $10^7$, $10^8$, $10^9$, $10^{10}$, $10^{11}$, or $10^{12}$ proteins. The sample is diluted before sequencing.

In additional aspects, the method further comprises digesting the protein with an enzyme. In some aspects, the enzyme site-specifically digests the protein. In certain aspects, the enzyme is trypsin. In some aspects, the digestion does not remove the N-terminal amino acid.

In some aspects, the method further comprises applying a second set of IPL rounds to the digested protein. In certain aspects, the method further comprises reconciling the duplicate barcode pairs from each set of IPL rounds to identify the protein.

In another embodiment, there is provided a method for uniquely labeling a protein comprising obtaining a sample comprising a plurality of proteins; attaching oligonucleotide tags comprising unique amino acid-specific barcodes to the plurality of proteins; splitting the sample into three or more compartments; labeling the plurality of proteins with a compartment-specific oligonucleotide tag; pooling the sample from the three or more compartments and re-splitting the sample into three or more compartments; and attaching a second compartment-specific oligonucleotide tag to the plurality of proteins, thereby obtaining a uniquely labeled protein.

In additional aspects, the method further comprises one or more rounds of pooling the sample, splitting the sample, and attaching additional compartment-specific oligonucleotide tags to obtain uniquely labeled proteins. In some aspects, the amino acid-specific barcode is specific for lysine, cysteine, glutamic acid, aspartic acid, tyrosine, tryptophan, or histidine. In certain aspects, the amino acids in the plurality of proteins comprise post-translationally modified side chains. In some aspects, the post-translationally modified side chains comprise phosphorylation, glycosylation, methylation, citrullination, or a combination thereof. In certain aspects, the amino acid-specific barcodes comprise a functional group to attach the barcode to the amino acid. In some aspects, the functional group is selected from the group consisting of succinimidyl ester, iodoacetamide, maleimide, amines, 4-phenyl-3H-1,2,4-triazole-3,5(4H)-dione (PTAD), 2,4-dinitrobenzenesulfenyl chloride, and a thiol.

In some aspects, the method further comprises digesting the protein with an enzyme. In certain aspects, the enzyme site-specifically digests the protein. In particular aspects, the enzyme is trypsin. In some aspects, the digestion does not remove the N-terminal amino acid.

In some aspects, the method further comprises applying a second set of IPL rounds to the digested protein.

In yet another embodiment, there is provided a method of determining the identity of a protein comprising obtaining a sample comprises a plurality of uniquely labeled proteins according to the present embodiments and aspects thereof; performing next-generation sequencing on the plurality of duplicate barcode pairs; and obtaining an amino acid pattern for a single protein or peptide from the next-generation sequencing and comparing the amino acid pattern to the proteome of an organism to identify the protein or peptide.

In certain aspects, the sample is a biological sample. In particular aspects, the biological sample is saliva, urine, blood, or whole tissue.

In particular aspects, the method does not comprise using microscopy. In some aspects, the individual molecule is not bound to a solid support. In certain aspects, the protein or peptide is a biomarker for cancer or an infectious disease. In specific aspects, the protein or peptide is free in solution. In some aspects, amino acids in the protein or peptide are labeled with amino-acid specific oligonucleotide tags each comprising a unique barcode. In some aspects, the sample comprises from about 2 to about $10^{12}$ proteins, such as at least 3, 4, 5, 10, 15, 20, 50, 100, 500, $10^3$, $10^4$, $10^5$, $10^6$, $10^7$, $10^8$, $10^9$, $10^{10}$, $10^{11}$, or $10^{12}$ proteins. In certain aspects, the sample is diluted before sequencing.

In additional aspects, the method further comprises digesting the protein with an enzyme. In some aspects, the enzyme site-specifically digests the protein. In some aspects, the enzyme is trypsin. In particular aspects, the digestion does not remove the N-terminal amino acid.

A further embodiment provides a method of detecting a molecular neighborhood comprising obtaining a dilute solution of proteins; generating positional information for amino acids using a two-round technique; analyzing the positional information to obtain the molecular neighborhood. In certain aspects, the method further comprises identifying a protein or protein complex which comprises amino acids in close proximity to each other. In some aspects, the method further comprises identifying at least a second protein or protein complex. In certain aspects, the two-round technique is IPL or split-and-pool labeling. In particular aspects, the two-round technique is a method according to the present embodiments and aspects thereof. In some aspects, the two-round technique comprises proteolysis between the first and second round.

As used herein, "essentially free," in terms of a specified component, is used herein to mean that none of the specified component has been purposefully formulated into a composition or is present as a contaminant or in trace amounts. The total amount of the specified component resulting from any unintended contamination of a composition is therefore well below 0.05%, preferably below 0.01%. In another embodiment, a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present disclosure will become apparent from the following detailed description. The detailed description and the specific examples, while indicating preferred embodiments of the disclosure, are given by way of illustration, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

FIGS. 1A-1D: Iterative Proximity Ligation Scheme Overview. A, top: Each iterative proximity ligation (IPL) oligonucleotide is a single-stranded deoxyribonucleic acid (DNA) synthesized to contain four components: a functional group for attachment, a primer site, a unique barcode sequence, and a restriction half-site. A, bottom: The oligonucleotide population is an approx. 1:1 mixture of two opposite polarities (A, bottom) such that they can be ligated using e.g. T4 ligase in the presence of a short bridging oligo. Primer and restriction site sequences are shared across each polarity; barcodes are unique across the entire population. (B) One round of IPL comprises ligating two oligonucleotides of opposite polarity, extending one of the primers to duplicate the barcode pair into the solution, and restriction to revert both oligonucleotides to their un-ligated state. (C) Presence of multiple neighboring oligonucleotides allows a different barcode pair to be recorded each round. IPL acts on a bulk population of oligonucleotides in parallel, with each round recording many barcode pairs at once. (D) After multiple IPL rounds, all recorded barcode pairs are sequenced by next-generation DNA sequencing. Interpretation of sequenced pairs as a graph—with each individual barcode treated as a node and each pair treated as an edge—leads to a rich application space.

FIG. 3: Six IPL rounds with a 0.3 ligation efficiency still recovers the original pattern overall. Note that nodes not connected to the largest graph component are not shown, as their position cannot be ascertained relative to the bulk of their connected peers.

FIGS. 4A-4B: IPL single molecule proteomics labeling scheme. (A) Cysteines, lysines, tryptophans, and carboxylates can be selectively labeled with barcoded oligonucleotides via handles specific to each amino-acid's side chain. The oligonucleotides encode the identity of their target amino-acid species and a random sequence unique to each individual amino acid amongst a large mixture of proteins. (Note: primers and half-restriction sites omitted from diagram for clarity.) (B) This chemistry is applied in bulk solution to a protein mixture, denaturing each protein and barcoding its amino acids.

FIGS. 7A-7C: Quantitation of ligated probes following ligation & restriction. A: Beads with attached probes were sampled after the first ligation, restriction, and second ligation for each of six replicates. The number of ligated probes were quantified in each after each reaction using qPCR. B: Each replicate's $C_q$ increased significantly after restriction, implying a significant decrease in remaining ligated pairs. C: All qPCR reactions were run on a PAGE gel with a size marker to confirm the 65 bp product size expected from the oligonucleotide sequences (Table 1).

FIG. 9: The Kamada-Kawai algorithm regards graph distance between two nodes as the desirable Euclidean distance between them. Concave geometries lead to nodes being much closer in Euclidean space (solid line with arrows) than in graph space (dashed line). This discrepancy forces nodes apart during graph layout. This problem was corrected for by taking the recovered layout and re-feeding it into a modified variant of the KK algorithm that performs local-only spring energy minimization instead of a global minimization. This significantly decreased large-scale distortions.

FIGS. 10A-10B: DNA as might be deposited on a surface with various photolithigraphed shapes. (FIG. 10B) Photolithigraphed shapes of analogue recovered under imperfect conditions.

FIGS. 12A-D: (A) Outline of control (non-split-and-pool) labeling & ligation experiments. (Step 1) Label double-AzK peptide with hexynyl oligo via CuAAC. Isolate doubly-labeled peptide by PAGE. (Step 2) Perform three rounds of barcode ligation onto labeled peptide and isolate the product. (Step 3) PCR amplify ligated barcodes and confirm sequence. (B) Control (non-split-and-pool) oligonucleotide designs. (SEQ ID NOS: 6-18) (C) Doubly labeled peptide isolated by PAGE. (D) Confirming presence of peptide by streptavidin gel shift.

FIGS. 14A-14E: (A) Barcodes for split-and-pool method. "N"s represent UMIs. (SEQ ID NOS: 19-48) (B) Split-and-pool ligated product isolated by PAGE. (C-D) Labeling cysteines using a thiol/maleimide reaction. (SEQ ID NOS: 50-51) (E) Ligation and PCR on thiol/maleimide labeled products.

FIGS. 16A-16D: (A) Distribution of the alignment scores. (B) Alignment scores for combination. (C) Representative alignments with scores≥260 (i.e. perfect alignment score for the product). (D) Representative alignments with scores between 240 and 250 (i.e. suboptimal alignments).

DETAILED DESCRIPTION

Figures 2A, 2B, 2C, 2D:
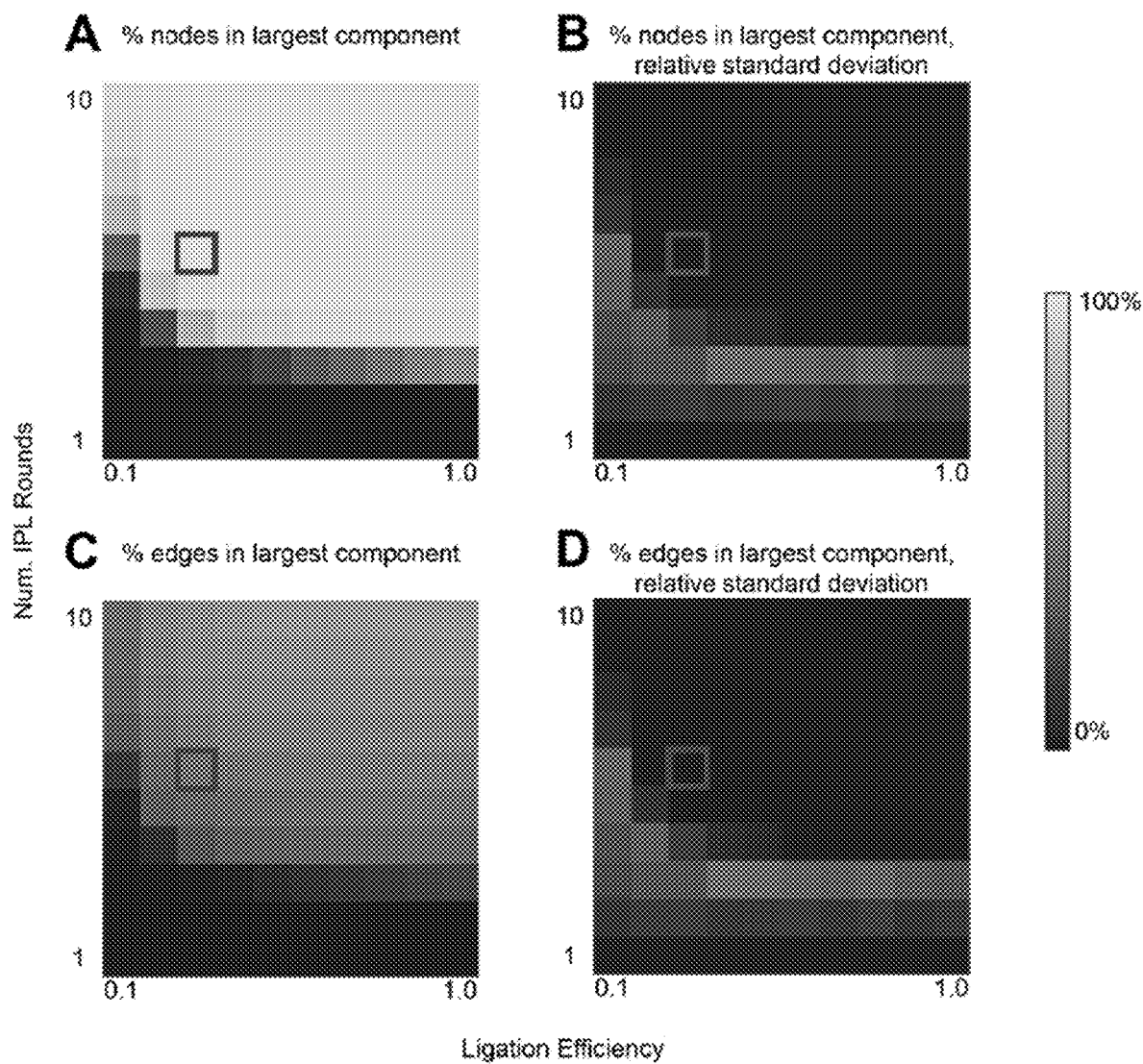
FIGS. 2A-2D: The number of possible nodes and possible edges recovered increases with the number of IPL rounds and ligation efficiency during each round. For each combination of IPL rounds and ligation efficiency parameters, 100 independent replicates were simulated of patterning a random "W" shape via a Poisson process, followed by iterative simulation of ligations between deposited oligonucleotides. The number of nodes and edges were then tallied participating in the largest IPL graph component as a percent of all possible participating nodes and edges under an ideal scenario (i.e. where all nodes would ligate with certainty if they were within reach of two complimentary oligonucleotides). (A) Percent of nodes participating in the largest component, averaged across 100 simulations. (B) Relative standard deviation across the 100 simulations in A. (C) Percent of possible edges participating in the largest component, averaged across the 100 simulations. (D) Relative standard deviation across the 100 simulations in C. Square indicates parameters used for simulation, with an average of 98% of nodes and 44% of possible edges participating in the largest component.

In certain embodiments, the present disclosure provides a novel approach for using nucleic acid sequencing to report on the relative spatial distributions of nucleic acid molecules (e.g., deoxyribonucleic acid (DNA) molecules), as measured by combining molecule-specific nucleic acid barcodes with a proximity ligation assay designed to be performed multiple, consecutive times. Such nucleic acid barcodes may be DNA or ribonucleic acid (RNA) barcodes. Such nucleic acid barcodes may be oligonucleotides having lengths of at least about 2, 3, 4, 5, 6, 7, 8, 9, 10, 20, 30, 40, 50, or more nucleic acid bases. Importantly, the present methods do not require the use of microscopy to detect or identify a molecule. By not relying on visual information, the present methods can sidestep limitations of traditional microscopy to obtain information about individual molecules in parallel, such as millions of molecules in parallel. In addition, the present methods do not depend on particle tracking, occlusion, or the complexity of the mixture.

The present studies demonstrated using computer simulations how the spatial positions of many DNA molecules can be simultaneously recovered using DNA sequence information. The methods provided herein may be used for determining object shapes (e.g., at a micrometer (or micron) scale) and single-molecule proteomics. In particular, the present studies experimentally demonstrate proof-of-principle iterative ligation on a simple model system.

The present methods employ DNA (or other nucleic acid, such as RNA) proximity ligation from a single readout per oligonucleotide pair to multiple reversible, iterative ligations re-using the same oligonucleotide molecules. Thus, certain embodiments of the present disclosure provide methods of using iterative proximity ligation (IPL) to capture multiple ligation events for each oligonucleotide and its various neighbors. Thus, the present methods can provide more detailed knowledge about the relative positions of the molecules as compared to single, irreversible ligation events. By integrating a unique DNA barcode into each participating oligonucleotide, a read-out of these ligation events may be obtained and thus provides the positional information contained therein in a high throughput manner using next-generation DNA sequencing.

Graph theory may be applied to the IPL sequencing results. This can be applied to multiple applications as described herein. In one method, the present studies show that geometric patterns of objects labeled by DNA can be obtained and single-molecule proteomics can be performed. In particular, it was demonstrated that letter patterns photolithographed onto slide-surfaces can be recovered using IPL sequencing data, illustrating how the present technique maps complex spatial configurations into DNA sequences and then—using this sequence information—recovers them. In another application, it was shown that IPL can identify and quantitate a large proportion of the *E. coli* proteome at single-molecule resolution even under suboptimal chemical and enzymatic reactivities.

Accordingly, methods are provided herein for assigning identity to individual molecules or physical positions using barcoded DNA molecules. Recording their pairwise proximities by iterative proximity ligation can reveal properties of the labeled objects. Specifically, iterative proximity ligation establishes a direct relationship between spatial position and sequence information. In one example of IPL for proximity detection, IPL comprising repetitive DNA ligation and digestion may be applied on a population of molecules. The population of IPL oligonucleotides can be ligated, restricted, and ligated again, with qPCR quantitating the efficiency of each step.

In one application of IPL, graph theory may be used to recover oligonucleotide positions, such as by using spring layout algorithms. The present methods have low error rates in positional recovery. For example, neighborhoods (e.g., about 1 µm diameter) can be recovered with an average oligonucleotide positional error less than the length of a ligated oligonucleotide pair. On scales substantially larger than individual oligonucleotides, three-dimensional shapes can be recovered using DNA sequencing.

Another application of IPL provided herein comprises single-molecule proteomics. This may be used to identify a peptide(s) or a protein(s) from a cell. A peptide may be a polypeptide. In this case, spatial proximity is informative because proximity of oligonucleotide-labeled amino-acids implies they share a polypeptide chain, allowing IPL to capture protein compositional information. The present studies showed that such compositional information is sufficient to uniquely identify a large proportion of the *E. coli* proteome even under imperfect labeling chemistries. Further methods provided herein concern detecting protein complexes by labeling individual proteins via antibodies or other tagging mechanisms. Thus, protein complex composition can be recovered at single-molecule resolution.

I. Molecular Neighborhood Detection

In sufficiently dilute solutions of proteins, proteins are far enough apart that each one's amino-acids are unlikely to be near the amino-acids belonging to other protein molecules. Therefore, a molecular neighborhood detection technique can infer which amino acids belong to the same protein by virtue of their proximity to each other—as they comprise the same molecule, i.e. the same neighborhood—while at the same time being far away from amino acids of other molecules. By detecting the amino acids in each neighborhood (each molecule), the number of each amino acid (e.g. Lys, Cys, etc.) belonging to that molecule can be counted. As shown in FIG. 5, this compositional information is sufficient to uniquely identify a large proportion of proteins in, for example, human and E. coli proteomes. Thus, in certain embodiments, there are provided methods for molecular neighborhood detection. The method can comprise obtaining a dilute solution of molecules, such as peptides, proteins, or protein complexes, obtaining positional information for amino acids within close proximity to each other and identifying the molecule which comprises said amino acids. Thus there are provided herein methods for detecting the molecular neighborhoods of amino acids which can be used to identify proteins or other molecules at single-molecule resolution. The present methods can be extended to other molecules where compositional information is present. For example, the same methods can be applied to protein complexes, labeling and counting individual proteins, and thus obtaining the stoichiometry of that complex.

One approach provided herein for detecting molecular neighborhoods, specifically to obtain compositional information, is IPL which can define a neighborhood by wherever an oligo probe can read. In another method provided herein, referred to as split-and-pool, can be used to define a neighborhood as a set of oligos linked to each other through a physical intermediate. The two-round compositional information, whether obtained by IPL or split-and-pool, can be used for neighborhood detection.

The compositional information obtained from the IPL or split-and-pool methods can then be analyzed using bioinformatics to identify one or more molecules, such as peptides, proteins, or protein complexes, in a sample, such as for proteomics analysis.

"Subject" and "patient" refer to either a human or non-human, such as primates, mammals, and vertebrates. In particular embodiments, the subject is a human.

"Sample" generally refers to a material obtained or isolated from a fresh or preserved biological sample or synthetically-created source that contains molecules of interest. Samples can include at least one cell, fetal cell, cell culture, tissue specimen, blood, serum, plasma, saliva, urine, tear, vaginal secretion, sweat, lymph fluid, cerebrospinal fluid, mucosa secretion, peritoneal fluid, ascites fluid, fecal matter, body exudates, umbilical cord blood, chorionic villi, amniotic fluid, embryonic tissue, multicellular embryo, lysate, extract, solution, or reaction mixture suspected of containing immune nucleic acids of interest. Samples can also include non-human sources, such as non-human primates, rodents and other mammals.

Samples can include, for example, a bodily fluid from a subject, including amniotic fluid surrounding a fetus, aqueous humor, bile, blood and blood plasma, cerumen (earwax), Cowper's fluid or pre- ejaculatory fluid, chyle, chyme, female ejaculate, interstitial fluid, lymph, menses, breast milk, mucus (including snot and phlegm), pleural fluid, pus, saliva, sebum (skin oil), semen, serum, sweat, tears, urine, vaginal lubrication, vomit, feces, internal body fluids including cerebrospinal fluid surrounding the brain and the spinal cord, synovial fluid surrounding bone joints, intracellular fluid (the fluid inside cells), and vitreous humour (the fluids in the eyeball). In particular aspects, the sample is a blood sample, such as a peripheral whole blood sample, or a fraction thereof. The sample may be whole, unfractionated blood. The blood sample can be at least about 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0 milliliters (mL), or more. The sample can be obtained by a health care provider, for example, a physician, physician assistant, nurse, veterinarian, dermatologist, rheumatologist, dentist, paramedic, or surgeon. The sample can be obtained by a research technician. More than one sample from a subject can be obtained.

A. Compositional Information

The compositional information of the present methods can be obtained by using IPL's repetitive DNA ligation and digestion. The method can comprise repeated ligation and restriction followed by DNA sequencing of the oligonucleotides. DNA oligonucleotides may be attached to single molecules and two oligonucleotides in sufficient proximity may then be ligated to each other. The pair of oligonucleotides may then be duplicated in solution and cleaved to un-ligate or separate the two oligonucleotides. For the next round, other neighboring oligonucleotides can pair and be duplicated and un-ligated. Multiple round of this IPL method can be performed to obtain spatial information on the individual molecules.

In some aspects, the compositional information may be obtained by the split-and-pool method in which the molecules may be labeled with tags in a split-and-pool method. For example, the molecules may be proteins or peptides labeled with both an amino acid identifier and a unique identifier in a sample. In this method, the sample is split into compartments, such as a number of wells, and ligated to an additional well-specific identifier. The compartments may be a well, microwell, or microfluidic droplet. Then, the sample is pooled and re-split before the addition of an additional, well-specific barcode to all of the conjugated oligonucleotides. The samples can then be pooled, and re-allotted to different wells, and a second, well-specific barcode is appended. Additional rounds of pooling, splitting, and ligation may be carried out in order to further diversify the combinatorial, ligated barcodes to the point where there is a unique combinatorial, ligated barcode for each protein or peptide. The key result is that each protein has its own unique barcode, and a copy of this barcode has been appended to each of the protein's labeled residues. Reading out the well codes (underlined) distinguishes the two proteins, and thus also indicates which residues go together on these proteins. The individual residues on each protein can be distinguished by their "unique barcode" sequences, and hence the number of each kind of amino acid (i.e., cysteine or lysine) that protein contains can be counted.

The terms "barcode," "unique tag" or "unique identifier" are used interchangeably herein to refer to a unique nucleotide sequence that is used to identify a single molecule or population of molecules. Barcodes can be linked to a target molecule of interest and used to trace back the amplicon. The barcode may be an oligonucleotide of 5-40 nucleotides, particularly 8-12 nucleotides, such as 8, 9, 10, 11, 12, 13, 14, or 15 nucleotides in length. In particular aspects, the barcode is comprised of random (e.g., degenerate) nucleotides.

The barcode or unique tag may be assigned to an individual molecule and then manipulated to determine if the tags are within proximity to each other. The DNA oligonucleotide may comprise a functional group, a primer site, a unique barcode, and a cleavage half-site, such as a restriction enzyme half-site. The cleavage half-site may be at the 5' or 3' end of the oligonucleotide. The cleavage site may be for an endonuclease, such as a blunt-end enzyme including but not limited to AanI, Acc16I, AccBSI, AccII, AcvI, AfaI, AfeI, AjiI, AleI, AluBI, AluI, Aor51HI, Asp700I, BalI, BbrPI, BmcAI, BmgBI, BmiI, BoxI, BsaAI, BsaBI, Bse8I, BseJI, Bsh1236I, BshFI, BsnI, Bsp68I, BspANI, BspFNI, BspLI, BsrBI, BssNAI, Bst1107I, BstBAI, BstC8I, BstFNI, BstPAI, BstSNI, BstUI, BstZ17I-HF, BsuRI, BtrI, BtμMI Cac8I, CviJI, CviKI-1, DinI, DpnI, DraI, Ec1136II, Eco105I, Eco147I, Eco32I, Eco47III, Eco53kI, Eco72I, EcoICRI, EcoRV, EcoRV-HF, EgeI, EheI, FaiI, FspAI, FspI, GlaI, HaeIII, HincII, HindII, HpaI, Hpy166II, Hpy8I, HpyCH4V, KspAI, MalI, MbiI, MlsI, MluNI, MlyI, Mox20I, MroXI, MscI, Ms1I, Msp20I, MspA1I, MssI, MvnI, NaeI, NlaIV, NruI, NruI-HF, NsbI, OliI, PceI, PdiI, PdmI, PmaCI, PmeI, Pm1I, Ppu21I, PshAI, PsiI, PspCI, PspN4I, PvuII, PvuII-HF, RruI, RsaI, RseI, ScaI, ScaI-HF, SchI, SfoI, SmaI, SmiI SmiMI, SnaBI, SrfI, SseBI, SspI, SspI-HF, StuI, SwaI, XmnI, ZraI, and ZrmI The functional group may be succinimidyl ester, iodoacetamide, maleimide, amines, 4-phenyl-3H-1,2,4-triazole-3,5(4H)-dione (PTAD), 2,4-dinitrobenzenesulfenyl chloride, a thiol, or any combination thereof. The oligonucleotides with cleavage sites of opposite polarity (i.e., 5' and 3) may be ligated by a protein ligase, such as T4 DNA ligase, T4 RNA ligase, Taq DNA ligase, T3 DNA ligase, or T7 DNA ligase.

The present methods may be used to determine the spatial positions and identities of individual molecules, such as single molecules within a population of molecules. The molecules may comprise a protein, protein complex, peptide, antibody, carbohydrate, nucleic acid, cell, signaling domain, lipid, carbohydrate, or a receptor. The individual molecules may be identified on a large-scale, such as from a sample with a population of molecules.

Proteins or peptides may be labeled at amino acid residues, such as cysteine, aspartic acid, or glutamic acid. Other residues may be labeled including, but not limited to, lysine, cysteine, glutamic acid, aspartic acid, tyrosine, tryptophan, histidine, or any combination thereof. The amino acids may be modified with phosphorylation, glycosylation, methylation, citrullination, or any combination thereof.

A. Sequencing

The term "primer" or "oligonucleotide primer" as used herein, refers to an oligonucleotide that hybridizes to the template strand of a nucleic acid and initiates synthesis of a nucleic acid strand complementary to the template strand when placed under conditions in which synthesis of a primer extension product is induced, i.e., in the presence of nucleotides and a polymerization-inducing agent such as a DNA or RNA polymerase and at suitable temperature, pH, metal concentration, and salt concentration. The primer is generally single-stranded for maximum efficiency in amplification, but may alternatively be double-stranded. If double-stranded, the primer can first be treated to separate its strands before being used to prepare extension products. This denaturation is typically affected by heat, but may alternatively be carried out using alkali, followed by neutralization. Thus, a "primer" is complementary to a template, and complexes by hydrogen bonding or hybridization with the template to give a primer/template complex for initiation of synthesis by a polymerase, which is extended by the addition of covalently bonded bases linked at its 3' end complementary to the template in the process of DNA or RNA synthesis.

"Polymerase chain reaction," or "PCR," generally refers to a reaction for the in vitro amplification of specific DNA sequences by the simultaneous primer extension of complementary strands of DNA. In other words, PCR is a reaction for making multiple copies or replicates of a target nucleic acid flanked by primer binding sites, such reaction comprising one or more repetitions of the following processes: (i) denaturing the target nucleic acid, (ii) annealing primers to the primer binding sites, and (iii) extending the primers by a nucleic acid polymerase in the presence of nucleoside triphosphates. Usually, the reaction is cycled through different temperatures optimized for each process in a thermal cycler instrument. Particular temperatures, durations at each process, and rates of change between processes depend on many factors, e.g., exemplified by the references: McPherson et al., editors, PCR: A Practical Approach and PCR2: A Practical Approach (IRL Press, Oxford, 1991 and 1995, respectively).

Any technique for sequencing nucleic acids can be used in the methods of the present disclosure. DNA sequencing techniques include dideoxy sequencing reactions (Sanger method) using labeled terminators or primers and gel separation in slab or capillary, sequencing-by-synthesis using reversibly terminated labeled nucleotides, pyrosequencing, 454 sequencing, allele specific hybridization to a library of labeled oligonucleotide probes, sequencing-by-synthesis using allele specific hybridization to a library of labeled clones that is followed by ligation, real time monitoring of the incorporation of labeled nucleotides during polymerization, and SOLiD sequencing. The input RNA may be 10%, 15%, 30%, or higher.

In certain embodiments, the sequencing technique used in the methods of the provided disclosure generates at least 100 reads per run, at least 200 reads per run, at least 300 reads per run, at least 400 reads per run, at least 500 reads per run, at least 600 reads per run, at least 700 reads per run, at least 800 reads per run, at least 900 reads per run, at least 1000 reads per run, at least 5,000 reads per run, at least 10,000 reads per run, at least 50,000 reads per run, at least 100,000 reads per run, at least 500,000 reads per run, at least 1,000,000 reads per run, at least 2,000,000 reads per run, at least 3,000,000 reads per run, at least 4,000,000 reads per run at least 5000,000 reads per run, at least 6,000,000 reads per run at least 7,000,000 reads per run at least 8,000,000 reads per run, at least 9,000,000 reads per run, at least 10,000,000 reads per run, or more.

In certain embodiments, the sequencing technique used in the methods of the provided disclosure can generate at least about 30 bp, about 40 bp, about 50 bp, about 60 bp, about 70 bp, about 80 bp, about 90 bp, about 100 bp, about 110, about 120 by per read, about 150 bp, about 200 bp, about 250 bp, about 300 bp, about 350 bp, about 400 bp, about 450 bp, about 500 bp, about 550 bp, about 600 bp, about 700 bp, about 800 bp, about 900 bp, about 1,000 bp, or more per read. For example, the sequencing technique used in the methods of the provided disclosure can generate at least about 30 bp, 40 bp, 50 bp, 60 bp, 70 bp, 80 bp, 90 bp, 100 bp, 110 bp, 120 bp, 150 bp, 200 bp, 250 bp, 300 bp, 350 bp, 400 bp, 450 bp, 500 bp, 550 bp, 600 bp, 650 bp, 700 bp, 750 bp, 800 bp, 850 bp, 900 bp, 950 bp, 1,000 bp, or more by per read.

1. HiSeq™ and MiSeq™ Sequencing

In particular aspects, the sequencing technologies used in the methods of the present disclosure include the HiSEQ™ system (e.g., HiSEQ2000™ and HiSEQIOOO™) and the MiSEQ™ system from Illumina, Inc. The HiSEQ™ system is based on massively parallel sequencing of millions of fragments using attachment of randomly fragmented genomic DNA to a planar, optically transparent surface and solid phase amplification to create a high-density sequencing flow cell with millions of clusters, each containing about 1,000 copies of template per sq. cm. These templates are sequenced using four-color DNA sequencing-by-synthesis technology. The MiSEQ™ system uses TruSeq, Illumina's reversible terminator-based sequencing-by-synthesis.

2. True Single Molecule Sequencing

A sequencing technique that can be used in the methods of the resent disclosure includes, for example, Helicos True Single Molecule Sequencing (tSMS) (Harris T. D. et al. (2008) Science 320: 106-109). In the tSMS technique, a DNA sample is cleaved into strands of approximately 100 to 200 nucleotides, and a polyA sequence is added to the 3' end of each DNA strand. Each strand is labeled by the addition of a fluorescently labeled adenosine nucleotide. The DNA strands are then hybridized to a flow cell, which contains millions of oligo-T capture sites that are immobilized to the flow cell surface. The templates can be at a density of about 100 million templates/cm². The flow cell is then loaded into an instrument, e.g., HeliScope™ sequencer, and a laser illuminates the surface of the flow cell, revealing the position of each template. A CCD camera can map the position of the templates on the flow cell surface. The template fluorescent label is then cleaved and washed away. The sequencing reaction begins by introducing a DNA polymerase and a fluorescently labeled nucleotide. The oligo-T nucleic acid serves as a primer. The polymerase incorporates the labeled nucleotides to the primer in a template directed manner. The polymerase and unincorporated nucleotides are removed. The templates that have directed incorporation of the fluorescently labeled nucleotide are detected by imaging the flow cell surface. After imaging, cleavage removes the fluorescent label, and the process is repeated with other fluorescently labeled nucleotides until a particular read length is achieved. Sequence information is collected with each nucleotide addition.

3. 454 Sequencing

Another example of a DNA sequencing technique that can be used in the methods of the present disclosure is 454 sequencing (Roche) (Margulies et al., 2005). 454 sequencing involves two processes. In the first process, DNA is sheared into fragments of approximately 300-800 base pairs, and the fragments are blunt ended. Oligonucleotide adaptors are then ligated to the ends of the fragments. The adaptors serve as primers for amplification and sequencing of the fragments. The fragments can be attached to DNA capture beads, e.g., streptavidin-coated beads using, e.g., Adaptor B, which contains 5'-biotin tag. The fragments attached to the beads are PCR amplified within droplets of an oil- water emulsion. The result is multiple copies of clonally amplified DNA fragments on each bead. In the second process, the beads are captured in wells (pico-liter sized). Pyrosequencing is performed on each DNA fragment in parallel. Addition of one or more nucleotides generates a light signal that is recorded by a CCD camera in a sequencing instrument. The signal strength is proportional to the number of nucleotides incorporated.

Pyrosequencing makes use of pyrophosphate (PPi) which is released upon nucleotide addition. PPi is converted to ATP by ATP sulfurylase in the presence of adenosine 5' phosphosulfate. Luciferase uses ATP to convert luciferin to oxyluciferin, and this reaction generates light that is detected and analyzed.

4. Genome Sequencer FLX™

Another example of a DNA sequencing technique that can be used in the present methods is the Genome Sequencer FLX systems (Roche/454). The Genome Sequences FLX systems (e.g., GS FLX/FLX+, GS Junior) offer more than 1 million high-quality reads per run and read lengths of 400 bases. These systems are ideally suited for de novo sequencing of whole genomes and transcriptomes of any size, metagenomic characterization of complex samples, or resequencing studies.

5. SOLiD™ Sequencing

Another example of a DNA sequencing technique that can be used in the methods of the present disclosure is SOLiD technology (Life Technologies, Inc.). In SOLiD sequencing, genomic DNA is sheared into fragments, and adaptors are attached to the 5' and 3' ends of the fragments to generate a fragment library. Alternatively, internal adaptors can be introduced by ligating adaptors to the 5' and 3' ends of the fragments, circularizing the fragments, digesting the circularized fragment to generate an internal adaptor, and attaching adaptors to the 5' and 3' ends of the resulting fragments to generate a mate-paired library. Next, clonal bead populations are prepared in microreactors containing beads, primers, template, and PCR components. Following PCR, the templates are denatured and beads are enriched to separate the beads with extended templates. Templates on the selected beads are subjected to a 3' modification that permits bonding to a glass slide.

The sequence can be determined by sequential hybridization and ligation of partially random oligonucleotides with a central determined base (or pair of bases) that is identified by a specific fluorophore. After a color is recorded, the ligated oligonucleotide is cleaved and removed and the process is then repeated.

6. Ion Torrent™ Sequencing

Another example of a DNA sequencing technique that can be used in the methods of the present disclosure is the IonTorrent system (Life Technologies, Inc.). Ion Torrent uses a high-density array of micro-machined wells to perform this biochemical process in a massively parallel way. Each well holds a different DNA template. Beneath the wells is an ion-sensitive layer and beneath that a proprietary Ion sensor. If a nucleotide, for example a C, is added to a DNA template and is then incorporated into a strand of DNA, a hydrogen ion will be released. The charge from that ion will change the pH of the solution, which can be detected by the proprietary ion sensor. The sequencer will call the base, going directly from chemical information to digital information. The Ion Personal Genome Machine (PGM™) sequencer then sequentially floods the chip with one nucleotide after another. If the next nucleotide that floods the chip is not a match, no voltage change will be recorded and no base will be called. If there are two identical bases on the DNA strand, the voltage will be double, and the chip will record two identical bases called. Because this is direct detection—no scanning, no cameras, no light—each nucleotide incorporation is recorded in seconds.

7. SOLEXA™ Sequencing

Another example of a sequencing technology that can be used in the methods of the present disclosure is SOLEXA sequencing (Illumina). SOLEXA sequencing is based on the amplification of DNA on a solid surface using fold-back PCR and anchored primers. Genomic DNA is fragmented, and adapters are added to the 5' and 3' ends of the fragments. DNA fragments that are attached to the surface of flow cell channels are extended and bridge amplified. The fragments become double stranded, and the double stranded molecules are denatured. Multiple cycles of the solid-phase amplification followed by denaturation can create several million clusters of approximately 1,000 copies of single-stranded DNA molecules of the same template in each channel of the flow cell. Primers, DNA polymerase and four fluorophore-labeled, reversibly terminating nucleotides are used to perform sequential sequencing. After nucleotide incorporation, a laser is used to excite the fluorophores, and an image is captured and the identity of the first base is recorded. The 3' terminators and fluorophores from each incorporated base are removed and the incorporation, detection and identification are repeated.

8. SMRT™ Sequencing

Another example of a sequencing technology that can be used in the methods of the present disclosure includes the single molecule, real-time (SMRT™) technology of Pacific Biosciences. In SMRT™, each of the four DNA bases is attached to one of four different fluorescent dyes. These dyes are phospholinked. A single DNA polymerase is immobilized with a single molecule of template single stranded DNA at the bottom of a zero-mode waveguide (ZMW). A ZMW is a confinement structure which enables observation of incorporation of a single nucleotide by DNA polymerase against the background of fluorescent nucleotides that rapidly diffuse in and out of the ZMW (in microseconds). It takes several milliseconds to incorporate a nucleotide into a growing strand. During this time, the fluorescent label is excited and produces a fluorescent signal, and the fluorescent tag is cleaved off. Detection of the corresponding fluorescence of the dye indicates which base was incorporated. The process is repeated.

9. Nanopore Sequencing

Another example of a sequencing technique that can be used is nanopore sequencing (Soni and Meller, 2007). A nanopore is a small hole, of the order of 1 nanometer in diameter. Immersion of a nanopore in a conducting fluid and application of a potential across it results in a slight electrical current due to conduction of ions through the nanopore. The amount of current which flows is sensitive to the size of the nanopore. As a DNA molecule passes through a nanopore, each nucleotide on the DNA molecule obstructs the nanopore to a different degree. Thus, the change in the current passing through the nanopore as the DNA molecule passes through the nanopore represents a reading of the DNA sequence.

B. Analysis of Sequencing

Analysis of the sequencing results may be performed using graph theory, such as for analyzing the IPL output. The readout may be interpreted as a graph wherein the barcoded oligonucleotides are nodes and observed ligations are edges (FIG. 1). The IPL graph may be modeled based on modification of Kama-Kawai algorithm as implemented by Graphviz and networkx, available as open source.

The IPL graphs can be modeled by Erdös-Rényi (ER) random graphs. Briefly, an ER random graph can be constructed by connecting pairs of nodes randomly: each pair may be connected by an edge with probability p independently of all other possible node pairs. If the IPL regime had all oligonucleotides spatially proximal to each other and any oligonucleotide pair has an equal probability of ligating as any other pair during each round, then after multiple rounds each oligonucleotide pair has had an equal and mostly independent chance to ligate. While during one single IPL round ligations between oligonucleotide pairs are mutually exclusive—i.e. each oligonucleotide can ligate to one other oligonucleotide at a time—and hence are not at all independent, over many rounds the cumulative probability of any pair ligating during any round approaches independence.

Random geometric graphs may be used to model the IPL graphs. Briefly, suppose a graph comprises points distributed across a surface with edges connecting points if they are within some distance r from each other. It may be assumed that oligonucleotides were distributed according to a homogenous Poisson point process (Penrose, 2003) within some defined geometrical shape. Such shapes can, for example, be patterned across slide surfaces using photolithography (Pirrung, 2002) or various other methods[14]. Unlike the case of ER graphs above, connectivity in RG scenarios is naturally contingent on the specific geometry of the shapes involved and therefore it is more difficult to make general guarantees.

C. Methods of Use

The present methods may be used to detect a single molecule for various applications including research and clinical applications including diagnostics and therapeutics. The diagnostics may be applied to various diseases including cancer and infectious diseases, such as HIV.

The methods may be used as a single-molecule proteomics platform by uniquely tagging each individual amino acid in a protein mixture. The proteomics may be used for agriculture, drug development, diagnostics, and research.

Further applications include the identification of biomarkers relevant to diseases including cancer and infectious diseases. The samples may be from noninvasive procedures such as collection of saliva, blood, or urine as compared to invasive samples, such as biopsies. The proteomics methods may comprise labeling amino acids residues and using the labels to obtain a pattern or stoichiometry of amino acids in successive peptides. This pattern may be searched against the proteome to identify the proteins. The present methods can be used to producing patterns sufficiently reflective of the peptide sequences to allow unique identification of a majority of proteins from a species (e.g. the yeast and human proteomes). Thus, in some embodiments, the present methods may be used for protein or peptide (e.g., hormones) diagnostics, such as from a non-invasive sample including blood, urine or saliva.

Other applications include determining the distribution of receptors on various cell types in order to understand cellular functions and disease states. The methods may be used to detect dimerizing receptors or signaling domains of cellular receptors. The methods may also be applied to other cell types or molecules, such as carbohydrates.

In further applications, the shape of molecules may be determined. For example, nanobeads may be coated with IPL oligonucleotides to recover bead shape and size with high resolution.

II. EXAMPLES

The following examples are included to demonstrate some embodiments of the disclosure. It can be appreciated that the techniques disclosed in the examples which follow represent techniques discovered by the inventor to function well in the practice of the disclosure. However, those of skill in the art can, in light of the present disclosure, appreciate that many changes can be made in the specific embodiments which are disclosed and still obtain a like or similar result without departing from the spirit and scope of the disclosure.

Example 1—Iterative Proximity Ligation

Iterative proximity ligation as a strategy to recover spatial information by DNA sequencing: Iterative proximity ligation (IPL) is based upon the observation that the processes of enzymatic ligation and digestion of DNA are (ideally) memoryless and hence can be applied repeatedly to the same strand multiple times. This observation was used to extend the concept of proximity ligation assays—which are typically limited to one ligation event per oligonucleotide pairs—to allow for multiple ligations per oligonucleotide. Thus, instead of being able to obtain one piece of information, namely that two particular oligonucleotides are in sufficient proximity to each other to ligate, many readouts of proximity information can be obtained about an oligonucleotide and its neighbors (FIG. 1). These readouts can be interpreted as a graph, where barcoded oligonucleotides are nodes and observed ligations are edges.

In particular, in order for oligonucleotides to have been ligated together, they are in close spatial proximity within a distance bounded by the lengths of the ligated molecules. Thus, the IPL graph intrinsically captures distance relationships among the molecules represented within the graph. Given enough measurements of pair-wise distances, it was shown that it is possible to triangulate and determine the position each molecule is held to generate the observed sequence pairs.

Computational simulations were performed to determine the feasibility for DNA sequencing to determine the spatial relationships among many molecules simultaneously. It was confirmed that there is a complete path from immobilized DNA molecules to sequence pairs and back to the implied positions of the DNA molecules, with positional errors on the order of the oligonucleotide chain lengths. Graph-theoretic properties common to several variants of IPL graphs are discussed, and which can be applied, but it not limited to, to two potential applications: nano- to micro-meter scale microscopy via DNA sequencing and single molecule proteomics.

IPL recovers complete graphs even for very large oligonucleotide pools: random graph theory and simulations:

Connectivity across a population of oligonucleotides is the primary readout obtained from IPL: the most important property sought in IPL graphs is for them to be connected because disconnected components are not very mutually informative. It was anticipated that a primary source of error common to all IPL schemes is failure of adjacent oligonucleotides to ligate, which risks fragmenting what in truth are connected oligonucleotide populations into many disconnected graphs. Fortunately, results from random graph theory and simulations showed that disconnected graphs rapidly become extremely unlikely after a handful of IPL rounds.

Two specific random graph models were used. The first model concerned IPL regimes where all oligonucleotides are in mutual proximity to each other and all pairs have an equal chance of ligating during each IPL round, and the second model concerned IPL regimes where the spatial distribution of oligonucleotides restricted each one to ligate its neighbors. These models are readily generalizable: each model's assumptions cover a wide range of potential IPL applications other than those explicitly proposed in the present studies.

The first variant of IPL graphs was well-modeled by Erdös-Rényi (ER) random graphs (Erdos and Renyi, 1964). Briefly, an ER random graph was constructed by connecting pairs of nodes randomly: each pair was connected by an edge with probability p independently of all other possible node pairs. If the IPL regime had all oligonucleotides spatially proximal to each other and any oligonucleotide pair has an equal probability of ligating as any other pair during each round, then after multiple rounds each oligonucleotide pair has had an equal and mostly independent chance to ligate. While during one single IPL round ligations between oligonucleotide pairs are mutually exclusive—i.e. each oligonucleotide can ligate to one other oligonucleotide at a time—and hence are not at all independent, over many rounds the cumulative probability of any pair ligating during any round approaches independence. The IPL scheme additionally deviates from ER assumptions in that its nodes have polarity: 5' nodes can ligate to 3' nodes and vice versa. However, if oligonucleotides of each polarity are considered as separate populations whose members are randomly "ligated" to each other after two IPL rounds—the extra round for probes of opposite polarity to act as intermediates—then the methods revert to near-ER assumptions with, at worst, a 2× penalty of rounds required.

IPL rounds were simulated on large graphs with 1000 mutually accessible nodes, with each node randomly chosen to have a 5' or a 3' polarity and ligation possible between 5' and 3' nodes. The simulations showed that even for such large graphs and with per-oligonucleotide-pair ligation probabilities of 10-2 per-round, complete graphs can be recovered with very high probability within five rounds (FIG. 2, top).

Graph theory provided further reassurances that even for large numbers of nodes, connected graphs were nevertheless very likely to be recovered. A result due to Erdös and Rényi$_9$ is that the connectivity of the ER graph has a threshold or "phase transition" property: if n is the number of nodes in the graph and p=c log nn where c is a constant, then as n→∞ the graph will almost certainly be disconnected if c<1 and will almost certainly be connected if c>1. Erdös and Rény provide an additional characterization of ER connectivity thresholding: if p=log n+cn where c is a constant, then as n→∞ the probability of the graph being connected is e−e−c.

A second variant of IPL graphs was well-modeled by random geometric graphs (Penrose, 2003) (RG). The present studies were restricted to oligonucleotides distributed across two-dimensional surfaces, although analogous results exist for higher dimensions. Briefly, suppose a graph comprises points distributed across a surface with edges connecting points if they are within some distance r from each other. In the present scenario, it was assumed that oligonucleotides were distributed according to a homogenous Poisson point process within some defined geometrical shape. Such shapes can, for example, be patterned across slide surfaces using photolithography or various other methods$_{14}$. Unlike the case of ER graphs above, connectivity in RG scenarios is naturally contingent on the specific geometry of the shapes involved and therefore it is more difficult to make general guarantees. There are additional complications such as edge effects, where nodes near the edge of a geometric distribution will differ in their connection opportunities as compared to their peers well inside the shape, and this effect may be exacerbated in the IPL scenario because polarity mismatch may prevent outlying oligonucleotides from connecting.

However, these concerns are readily obviated if the oligonucleotide density is sufficiently increased (Balister, 2008). Simply put, since each local neighborhood of oligonucleotides is deposited independently of all other neighborhoods, and since at sufficient oligonucleotide density it becomes almost certain that all neighborhoods will become connected (barring some possible outliers), then almost all oligonucleotides within the area of interest belong to the same IPL graph. Although estimates for the required density under various assumptions exist, there is no model that incorporates the oligonucleotide polarity constraint. Therefore, simulations were used to demonstrate that above a certain oligonucleotide density a connected IPL graph containing all nodes can be recovered (FIG. 2, bottom).

Example 2—Applications of Iterative Proximity Ligation

Recovery of positional information by DNA sequencing and spring graph layouts: IPL can be used to obtain spatial information about shapes much larger than the molecules used. The present studies demonstrated by simulation that two-dimensional patterns can be recovered by applying spring layout algorithms to IPL graphs.

First, deposition of DNA oligonucleotides on a flat glass slide was simulated as a Poisson point process (Kingman, 1993). Each oligonucleotide was randomly assigned a 5' or 3' polarity with equal probability. It was assumed that oligonucleotides were covalently attached within a shape (FIG. 3A). It was assumed that after multiple rounds of IPL that any probes sufficiently close to each other would ligate at least once with certainty. The list of barcode pairs thus obtained was used to recover the layout: no additional knowledge whatsoever about oligonucleotide positions was used.

The Graphviz Neato implementation of the Kamada-Kawai (KK) algorithm (Kamada and Kawai, 1989) was used to recover the layout (FIG. 3B). The algorithm initializes node positions randomly and thus may cause topologically twisted layouts (FIG. 9), so a layered layout strategy was pursued. The graph center—defined as the set of nodes with graph eccentricity equal to graph radius (Harary, 2001)—was identified and a randomly selected central node was used as a seed to layout the neighborhood of radius 1 around it. The positions of nodes in this layout were used to initialize the layout the neighborhood of radius 2. This cycle was repeated until all nodes were laid out. The recovered shape was scaled such that the median distance between oligonucleotides in the recovered layout was equal to the median distance in the original shape. Note that due to the nature of the Poisson point process this median value is, except in pathological cases, dependent on the Poisson parameter λ and hence highly conserved between different shapes. To measure large scale shape distortion in the layout versus the actual oligonucleotide positions, the original shape and the recovered layout were aligned. First, the node in the closest to the centroid of the actual shape was chosen as a coordinate origin. The same node (red spot in FIG. 3B) in the layout was aligned to the coordinate origin, and the optimal rotation (within 0.1° resolution) that minimizes the sum of Euclidean distances between nodes' original and recovered positions was found. For each node, the Euclidean distance was measured between its original and recovered positions (FIG. 3B, heatmap).

Figure 10A:
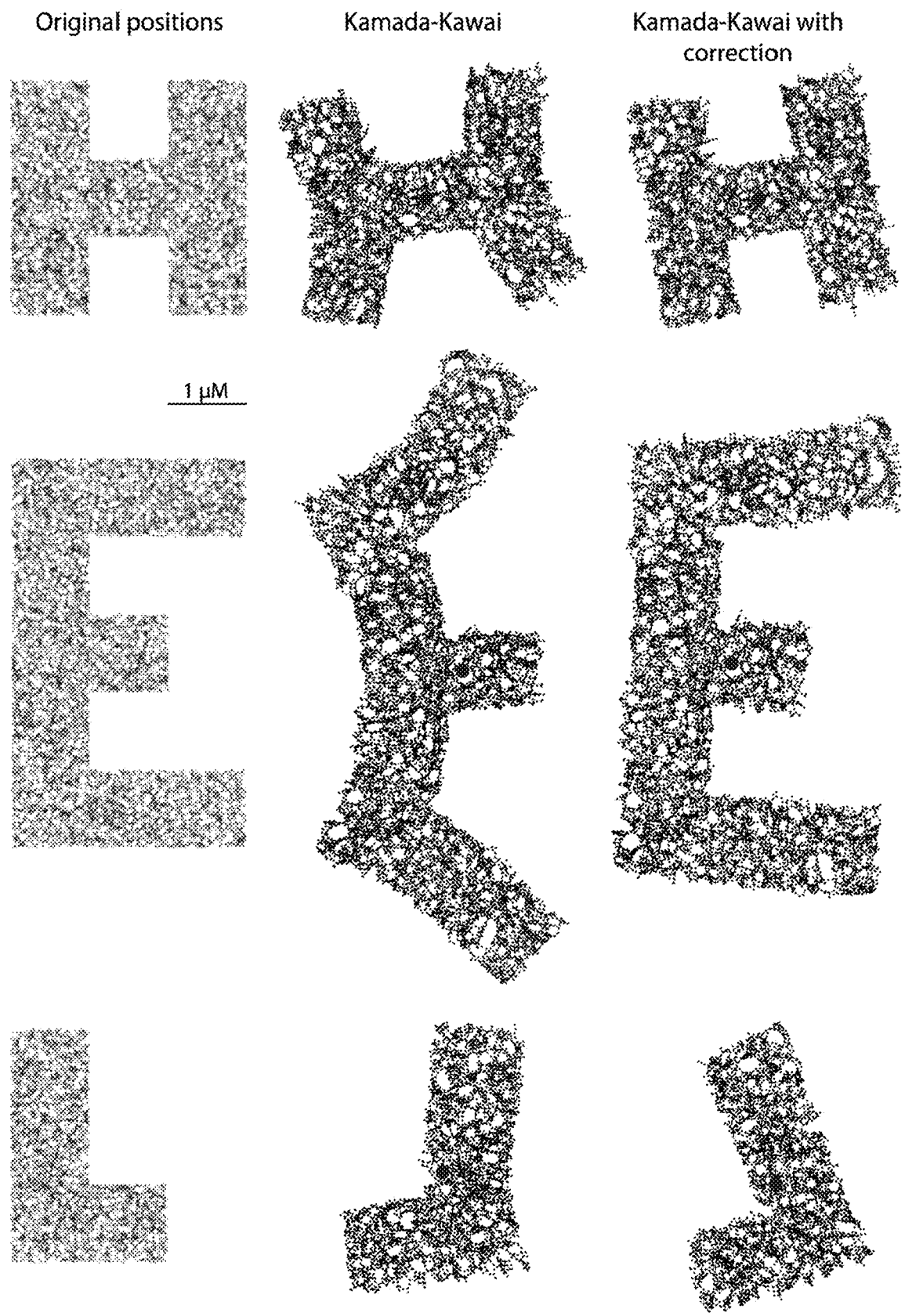
Figure 10A:
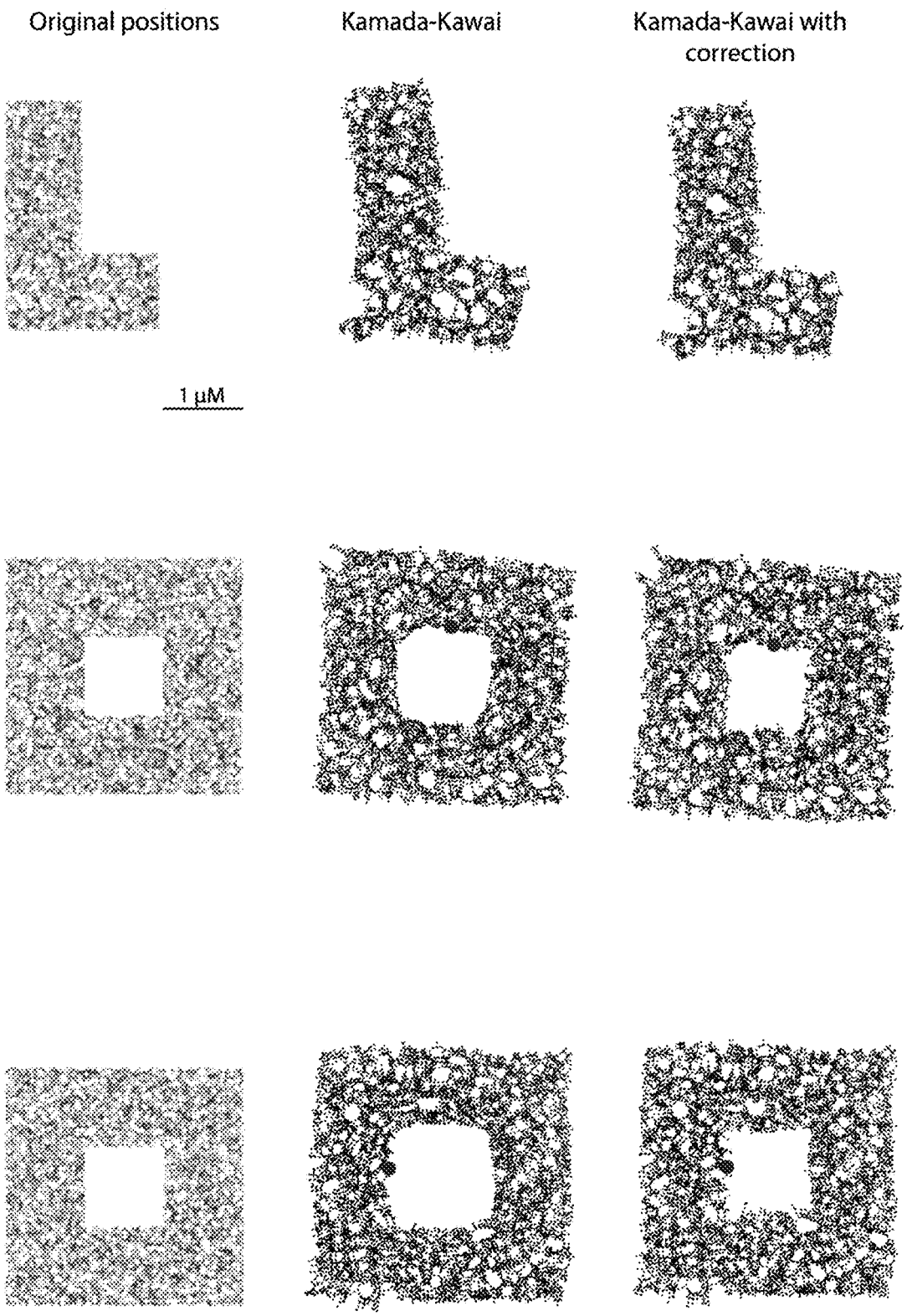

The primary cause of distortion was the discrepancy between the fundamental assumptions of the KK algorithm and concave geometries (FIG. 10). To correct for this, the recovered layout was taken and re-fed into a modified variant of the KK algorithm that performs local-only spring energy minimization instead of a global minimization. This significantly decreased large-scale distortions.

Using this approach, all the letters for message "HELLO WORLD" (FIG. 11) were recovered. Note that the orientation of some letters is inverted and that this is equally consistent with the information provided: this ambiguity cannot be resolved without additional information such as fiduciary markers or connections spanning the letters.

KK layout of two-dimensional patterns recovered not only large-scale structure (FIG. 3C) but also finer structural details (FIG. 3A'-C'). To quantify layout fidelity at smaller scales, 50 nodes (oligonucleotides) were randomly sampled from each letter in "HELLO WORLD" and their neighborhoods of graph radius 10 were examined, corresponding to a physical distance of approx 597+/−82 nm (mean+/−std.dev.) from the sampled node. For each oligonucleotide in this neighborhood, the distance between its original and recovered position was compared with the sampled node acting as the common coordinate origin for the local comparison. The difference in position for all nodes was 48+/−33 nm with a median of 42 nm. It was expected that nodes further on the graph from sampled node would have a larger error: looking at nodes 10 hops from the sampled node, the difference in position was 52+/36 nm with a median of 46 nm. The recovered oligonucleotide positions within a half-micrometer radius circle deviate from their true positions by 5% of its diameter. Note that each oligonucleotide is approx. 34 nm in length, meaning that the average error in recovered position is smaller than the maximum reach of an oligonucleotide pair. As can be observed around the "holes" in FIG. 3A'-C', a primary cause of local distortion is the same concave geometry problem above that affects larger-scale structures.

Single-molecule proteomics: By labeling proteins with oligonucleotides, IPL can be applied as a method for single-molecule proteomics. It was demonstrated by simulation that the vast majority of a single cell's proteome can be reliably detected and quantified using this technique.

Figures 5A, 5B, 5C:
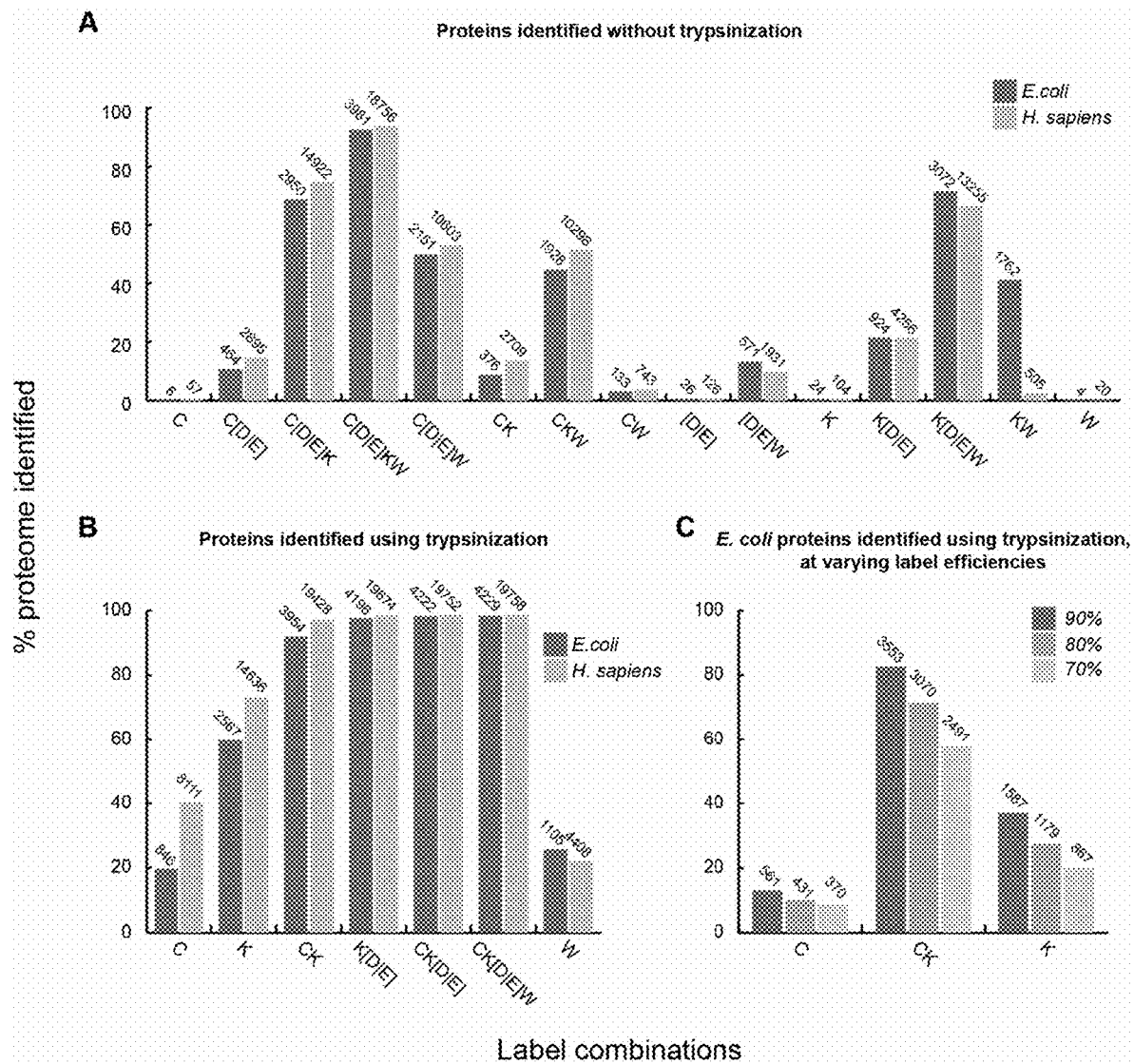
FIGS. 5A-5C: Partial amino acid composition is sufficient to uniquely identify proteins. A: Performing IPL on a dilute population of labeled proteins yields a tally of labeled amino acids for each protein. This partial compositional information is sufficient to identify a substantial portion of the E. coli and H. sapiens proteomes using three-label combinations. "[DIE]" indicates Asp/Glu labels. Number proteins identified is above each bar. The E. coli and H. sapiens proteomes used for the simulation contain 4297 and 19988 proteins respectively. B: After applying an initial sequence of IPL rounds on whole proteins, they can be digested by trypsin and another sequence of IPL rounds can be repeated on the tryptic peptides. Oligonucleotide pairs from the first and second sets of IPL rounds can be reconciled because all barcodes are unique across the entire protein population. The additional compositional information about tryptic subsequences in the second stage significantly boosts identification. C: Substantial proportions of the proteome can be identified even at reduced label efficiencies. Labeling efficiencies for Cys and Asp/Glu have experimentally been shown to be quantitative.

A protein labeling scheme (Hernandez, 2017) was used for the single-molecule peptide sequencing technology (Swaninathan, 2015). This scheme was adapted to selectively tag amino acids with a variant of IPL oligonucleotides such that each oligonucleotide encodes the identity of its target amino acid species and a molecular barcode unique to the individual amino acid even amongst a large pool of proteins (FIG. 4). Once proteins are labeled, they are diluted and IPL is applied to the entire solution in bulk. If the proteins are sufficiently dilute, then oligonucleotides on the same protein will ligate and yield intramolecular oligonucleotide pairs while oligonucleotides on separate proteins will be extremely unlikely to ligate and hence will not yield intermolecular pairs. Since the proteins are denatured upon labeling, all oligonucleotide pairs on a single protein are equally likely to ligate and therefore, per the graph-theoretical considerations above, the protein's IPL graph is well-modeled as an Erdös-Rényi random graph with extremely likely connectivity after several rounds. Each protein will thus yield its own connected IPL graph, with nodes representing its labeled amino acids. Tallying amino acids from the graph recovers the protein's partial compositional information, which is sufficient to identify a substantial proportion of a proteome (FIG. 5A).

Protein identification is significantly boosted if, after this initial sequence of IPL rounds, the proteins are site-specifically digested via e.g. trypsin and a second sequence of IPL rounds is applied to the digested peptides. Since each amino-acid's barcode is unique in the entire population, they can be used to reconcile barcode pairs obtained from both rounds. The additional information from the second stage yields compositional information about each fragment, and the specificity of the proteolytic enzyme contributes partial sequence information. This additional information allows even two-label schemes to resolve the vast majority of proteins in a proteome (FIG. 5B).

Labeling efficiencies for cysteines and carboxylates are quantitative (Schnatbaum et al., 2016). Nevertheless, to characterize the method's robustness against labeling failure, simulated protein identification was simulated under progressively lower labeling efficiencies. This approach is analogous to strategies for computationally evaluating the feasibility the single-molecule protein sequencing technology. Briefly, $10^4$ copies of each protein in the *E. coli* proteome were simulated to undergo labeling at their Cys and/or Asp/Glu residues at a given stochastic probability, with each amino-acid labeling event modeled as an independent Bernoulli random variable. It was assumed that all proteins yielded complete IPL graphs incorporating all labeled amino acids, and that a two-stage strategy yielded amino acid compositions of all tryptic peptides in each protein. Thus, the combination of amino acid compositions for the tryptic peptides was obtained as the compositional signature of each protein. A protein was considered identifiable if it yielded a compositional signature at least 10 times (out of $10^4$), with all other proteins contributing at most 10% of that signature's total occurrences. The results showed that even under a 90% efficient labeling regime, the two-stage IPL strategy can still identify a substantial portion of the proteome (FIG. 5C).

Figure 6:
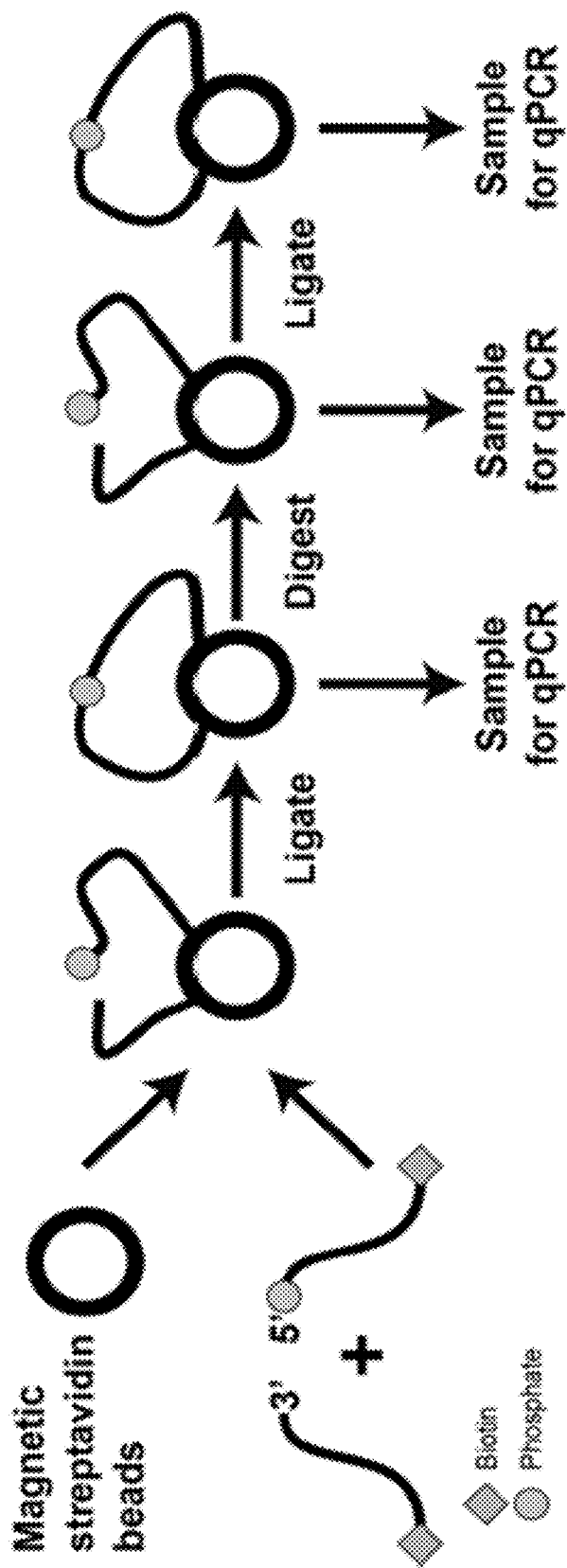
FIG. 6: Testing reversible ligation on solid support. Left and right probes (Table 1) were mixed in approx. a 1:1 ratio and then incubated with magnetic streptavidin beads. After the first ligation, beads were mixed well and randomly sampled by pipette for qPCR. The remaining beads were washed and incubated with a restriction enzyme, and sampled again. A second ligation was carried out and sampled. All ligations and restrictions required addition of a connector complementary to the restriction/ligation site (Table 1).

Initial Instantiation of iterative proximity ligation (IPL): In order to demonstrate the feasibility of iterative proximity ligation (IPL), streptavidin was used to immobilize biotinylated oligonucleotides adjacent to one another. The oligonucleotides were designed such that their ligation can be reversed by the addition of a restriction endonuclease, leading to potential rounds of ligation, cleavage, and re-ligation (Table 1). One such round was performed, using qPCR to quantify the proportion of ligated products after each reaction (FIG. 6). Six replicates of these experiments were performed.

Figure 7A:
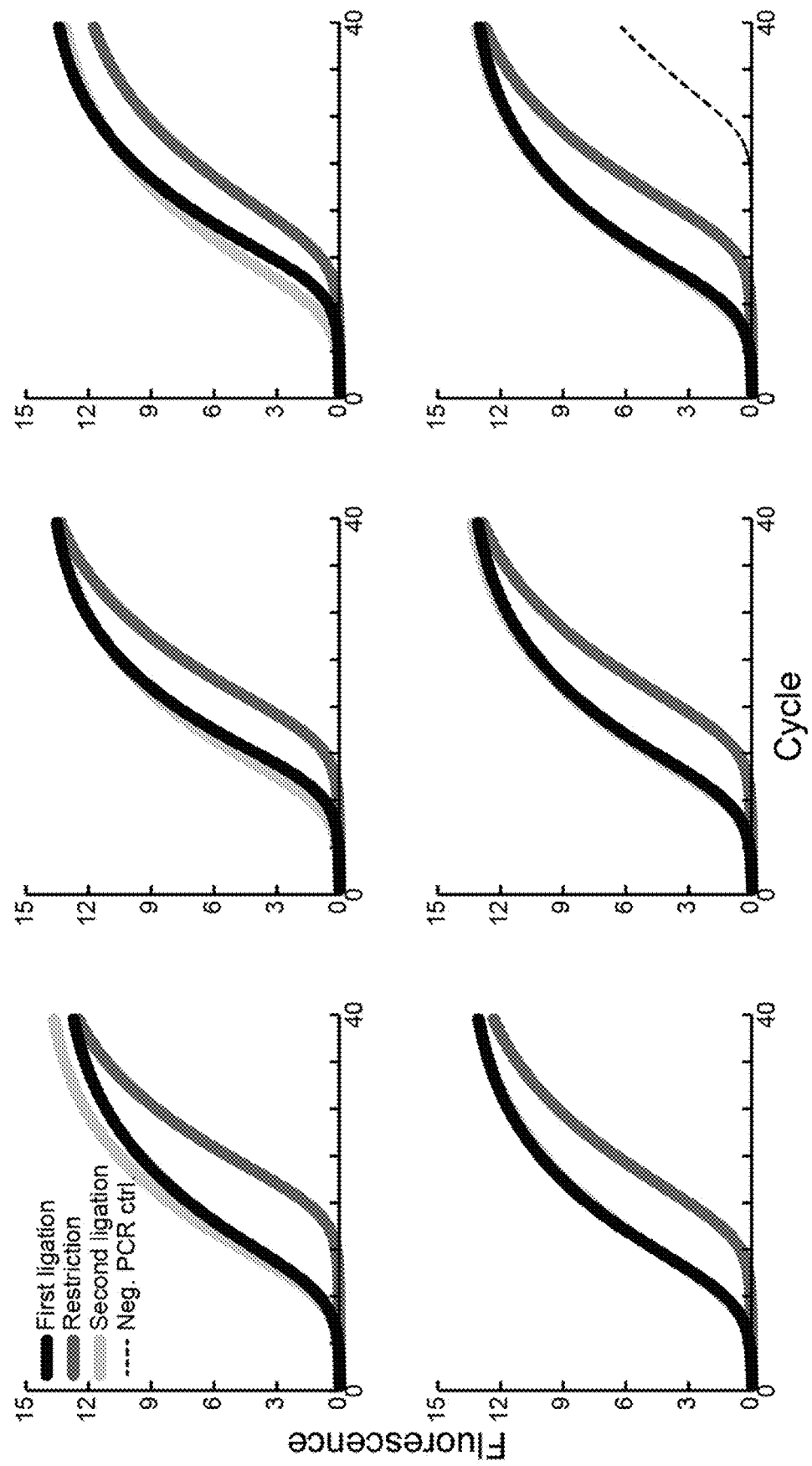
Figure 8:
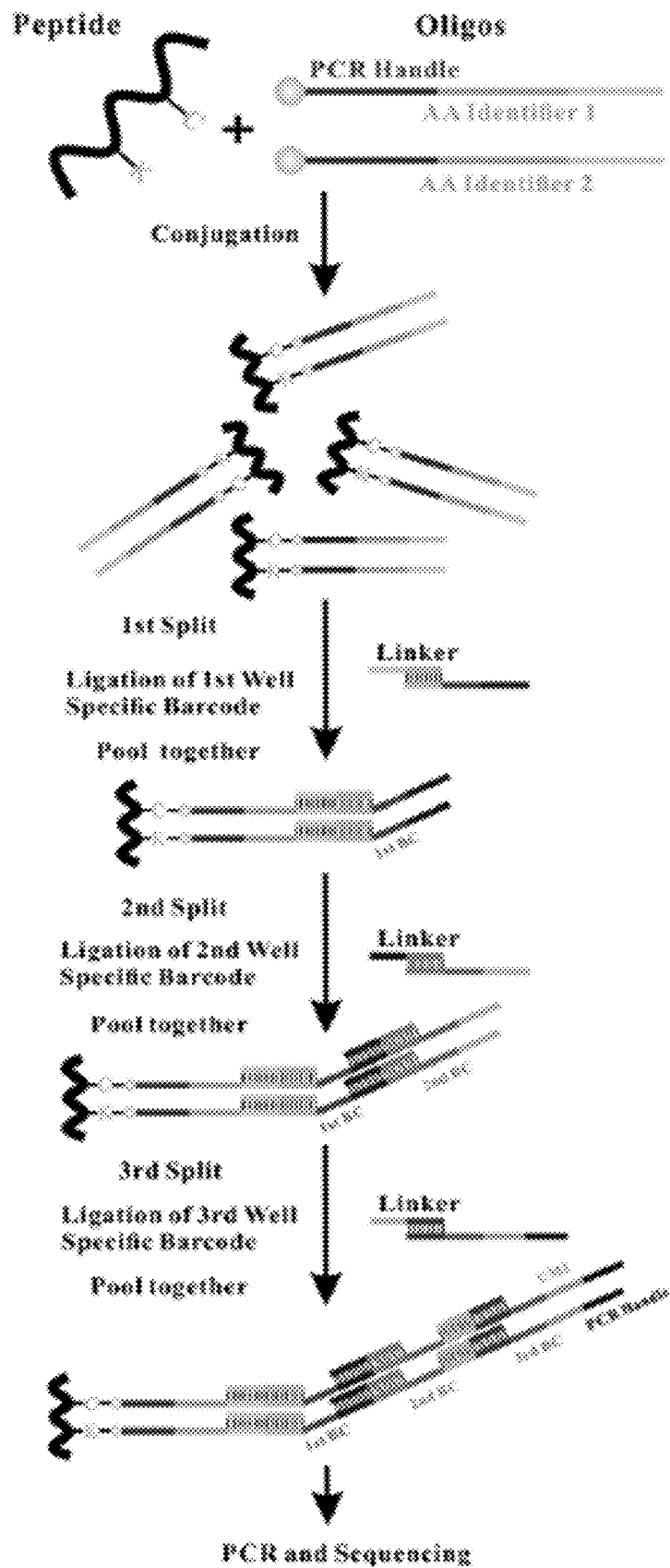
FIG. 8: Schematic depicting split-sequencing single molecule proteomics method for barcoding and identifying amino acids within a protein.

Initially, biotinylated left probe and right probe (2.5 μL of 10 μM stocks, each) were mixed and incubated with 2 μL streptavidin beads in 1× B&W buffer, with the probe and bead concentrations adjusted to ensure there were approximately equimolar numbers of probes and streptavidin binding sites. Upon the addition of T4 ligase and 1 mM ATP and further incubation for 5 min at 37° C., a 10 µL sample was taken for qPCR, which yielded an average $C_q$ (time to signal) of 4.6±1.0 (mean±std. dev. across six replicates) (FIG. 7B). The beads were then washed and incubated with EcoRV-HF enzyme for 2 hours at 37° C. to cleave templates that yielded amplicons, and another 10 µL sample (equivalent in concentration to the first) was taken for qPCR analysis. The average increase in $C_q$ for the digested samples was 6.3±2.0, indicating that a significant portion of the ligated probes had indeed been digested. To regenerate the template, the beads were again washed to remove the restriction endonuclease and then incubated with a more concentrated T4 ligase for 15 min at 37° C. The 10 µL sample showed a decrease in $C_q$ of 7.1±1.2, indicating that cleaved probes were being religated (FIG. 7A, B). Overall, the $C_q$ values went from 4.6±1.0 to 10.9±1.4 upon cleavage to 3.8±0.31 upon religation. All qPCR products were confirmed to correspond to the correct size as expected from the designs (Table 1) by 10% PAGE (FIG. 7C).

Cysteine identifier—unique barcode—well code 1—well code 2—well code 3
Lysine identifier—unique barcode—well code 1—well code 2—well code 3

In contrast, a different single protein with two lysines and one cysteine might have the following sequences appended to it:

Cysteine identifier—unique barcode—well code 1—well code 4—well code 5
Lysine identifier—unique barcode—well code 1—well code 4—well code 5
Lysine identifier—unique barcode—well code 1—well code 4—well code 5

As can be seen, reading out the well codes distinguishes the two proteins, and thus also indicates which residues go together on these proteins. The individual residues on each protein are distinguished by their "unique barcode" sequences (italicized), and hence the number of each kind of amino acid (i.e., cysteine or lysine) that protein contains can be counted. This yields, in effect, the same compositional information as provided by IPL.

TABLE 1

Oligonucleotide sequences.

| Oligonucleotides | Sequences | SEQ ID NO: |
|---|---|---|
| left probe | /5Biosg/TT TTT TTT TTT TTT TTT TTT TTT TTT TTT TTT TTT TTT TTT TTT TTT TTT TTT TTT TTT/iSp18/CGC TTC AGG TAG TAG TAC GTC TAT GTA TGA T | 1 |
| right probe | /5Phos/ATC CTG TAG CAT TAA TAC TCT CGC AGC ACA ACG GTA C /iSp18/ TTT TTT TTT TTT TTT TTT TTT TTTTTT TTT TTT TTT TTT TTT TTT TTT TTT TT /3Bio/ | 2 |
| connector | CTA CAG GAT A TCA TAC AT/3InvdT/ | 3 |
| forward primer | CGC TTC AGG TAG TAG TAC GTC T | 4 |
| reverse primer | C CGT TGT GCT GCG AGA GTA TTA | 5 |

Example 3—Split-Seq Single Molecule Proteomics

In addition to using IPL to identify amino acid-specific amplicons within the same protein, a separate method was proposed for barcoding and identifying amino acids within a protein.

As with IPL, oligonucleotides with both an amino acid identifier and a unique identifier will be conjugated to individual amino acids within individual proteins. The sample is then split into a number of wells (i.e., in a 96-well plate) and ligated to an additional, well-specific barcode to the all of the conjugated oligonucleotides. The samples are then pooled, and re-allotted to different wells, and a second, well-specific barcode is appended; this diversifies the number of different barcode combinations on individual samples to ca. 96×96≈10,000 (for example). Additional rounds of pooling, splitting, and ligation are carried out in order to further diversify the combinatorial, ligated barcodes to the point where there is a unique combinatorial, ligated barcode for each protein or peptide. The key result is that each protein has its own unique barcode, and a copy of this barcode has been appended to each of the protein's labeled residues.

For example, a single protein or peptide that contained two cysteine residues and a lysine residue might have the following sequences appended to it, after three rounds of split-and-pool ligation:

Cysteine identifier—unique barcode—well code 1—well code 2—well code 3

Note that the IPL simulations demonstrating that the vast majority of a proteome can be resolved even under suboptimal labeling efficiencies (below those observed in practice) are directly applicable to this technique.

Using this method, upwards of $10^{12}$ proteins can be barcoded in a mixture. This would require up to six rounds of split-and-pool barcode addition for a 96 well plate. There would be potentially fewer rounds for identification depending on the number of well codes used: for example, 5 rounds in a 384 well plate can yield about $10^{11}$ unique protein tags. Such numbers are within the grasp of current NextGen DNA sequencing methods, effectively converting single molecule protein composition identification to NextGen DNA sequencing. As more amino acid tags are used, the increasingly precise composition of individual proteins allow their identification (e.g., via look-up tables for organisms).

Example 4—Materials and Methods

Simulating Erdös-Rényi (ER) random graph connectivity: IPL ligation was simulated for graphs with 1000 nodes at varying ligation probabilities. Each node was randomly chosen to have a 5' or 3' polarity, with ligation possible between opposite polarities. During each round, all possible oligonucleotide pairs were iterated through in random order and each was potentially ligated at the given probability. Each oligonucleotide can ligate to one partner per round: if an oligonucleotide pair successfully ligated at any point during the iteration, its members can not participate in any subsequent pairings during that round. 100 simulation replicates were performed for each ligation probability and the size of the largest component was measured after each round.

Simulating random geometric graph (RG) connectivity: 34 nm long (~100 base) IPL oligonucleotides were deposited by simulation onto a square pattern on a flat surface (68 nm×15)$_2$=1.04 μm$_2$ in size as a Poisson point process with intensity parameter λ=5 oligonucleotides/(68 nm×68 nm). Each oligonucleotide was randomly assigned 3' or 5' polarity. During each round, all oligonucleotide pairs within 2×34 nm=68 nm of each other and of complimentary polarities were iterated through in random order and each was potentially ligated at the given probability. Each oligonucleotide can at most participate in one ligation per round. 100 simulation replicates were performed for each ligation probability and the size of the largest component was measured each round. Since a new graph was generated for each ligation probability and their total node number varies, the size of the largest component was expressed as the percentage of the graph's total nodes belonging to it.

Simulating recovery of spatial information (letter patterns) from DNA sequences using spring-layout algorithms: 34 nm long (~100 base) IPL oligonucleotides were deposited by simulation onto letter shape patterns on a flat surface as a Poisson point process with intensity parameter λ=5 oligonucleotides/(68 nm×68 nm). Each oligonucleotide was randomly assigned 3' or 5' polarity. It was assumed all oligonucleotides within 2×34 nm=68 nm of each other and of complimentary polarities were ligated at some point during at least one IPL round.

Representing each IPL oligonucleotide as a node and each ligated pair as an edge, a graph was constructed using the possible oligo-oligo ligations obtained above. Any nodes not belonging to the largest connected component were discarded; the largest connected component was retained for further analysis. In practice, this meant<1% of nodes were discarded.

Graphviz's implementation of the Kamada-Kawai (KK) algorithm was iteratively applied to recover the original letter shape. The graph center—defined as the set of nodes with graph eccentricity equal to graph radius—was identified and used a randomly selected central node as a seed to layout the neighborhood of radius 1 around it. The positions of nodes in this layout were then used to initialize the layout the neighborhood of radius 2. This cycle was repeated until all nodes were laid out. The recovered shape was scaled such that the median distance between oligonucleotides in the recovered layout was equal to the median distance in the original shape.

To obtain a corrected KK layout, networkx's Python implementation[27] of the KK algorithm was implemented to ignore node-node spring interactions outside of graph radius 5. The layout obtained from this round of the iterative Graphviz KK layout was fed into this modified function to obtain the corrected layout.

For both corrected and uncorrected variants, the node coordinates were scaled such that the median node-node Euclidean distance in the layout was equal to the median oligonucleotide-oligonucleotide distance between Poisson deposited oligonucleotides.

To characterize distortion of the recovered layout, the node in the original layout closest to the centroid of all oligonucleotide positions was selected as an anchor node. The anchor node in original and recovered layouts were aligned, and rotated the recovered layout (at 0.1° resolution) around it to minimize the sum of Euclidean distances between original and recovered node positions. To account for the recovered shape possibly being a mirror inversion of the original, this was repeated for both orientations, and selected the orientation that minimized this sum. Once the best-fitting alignment orientation and angle were chosen, each node the Euclidean distance was then calculated between its original and recovered position.

Simulating single-molecule proteome coverage: UniProtKB/Swiss-Prot complete *E. coli* and *H. sapiens* proteomes (manually reviewed) were downloaded on 16 May 2016 and used for all simulations, comprising 4297 and 19988 annotated proteins, respectively. Alternatively-spliced isoforms were ignored.

Identification of proteins without trypsinization at perfect labeling efficiency: For each labeling scheme, the number of labeled amino acids in each protein were tallied and represented this result as an ordered tuple. For example, a protein with 3 lysines and 5 cystines would be represented as (3, 5). A protein was unique if no other protein's composition was represented by the same tuple.

Identification of proteins using trypsinization at perfect labeling efficiency: Each protein's sequence was cut after each lysine and arginine. Each protein fragment's amino acid composition was represented as a tuple, and each protein's composition was represented as the multiset of fragment tuples. A protein was unique if no other protein's composition was represented by the same multiset of tuples.

Identification of proteins using trypsinization at suboptimal labeling efficiencies: $10^4$ molecular replicates were simulated for each protein in a Monte Carlo fashion. Each protein's sequence was cut after each lysine and arginine. For each replicate, each amino-acid was labeled with the given stochastic labeling probability. Each individual replicate's composition was represented by a multiset as above, however counting successfully labeled amino acids. For each protein, observed multisets were collated from all $10^4$ replicates. A protein was unique if it had at least one multiset that occurred at least 10 times, and that the number of instances of that multiset observed in all other proteins accounted for at most 10% of all its occurrences across the proteome.

Iterative Proximity Ligation on Magnetic Streptavidin Beads

Materials and bead preparation: 2× binding and washing (B&W) buffer was prepared per Invitrogen as 10 mM Tris-HCl (pH 7.5), 1 mM EDTA, 2 M NaCl. Biotinylated left and right probes (10 μM; Table 1) were mixed in 1× B&W buffer in a total volume of 30 μL to concentrations of 0.78 μM each. The mixture was incubated with 2 μL of stock Invitrogen Dynabeads M-270 Streptavidin (Invitrogen catalog #65305) at room temperature for 20 minutes to allow immobilization. After binding, beads were washed with 200 μL of 1× B&W buffer and resuspended in 200 μL nuclease-free H$_2$O.

Iterative proximity ligation: Some 22 μL of resuspended beads was combined with 22 μL of 100 nM connector (Table 1). Ligation was carried out by adding 5 μL 10× ligation buffer (NEB B0202S) and 1 μL of T4 ligase (NEB M0202S) diluted in 1× ligation buffer to 40 U/μL, and incubating for 5 minutes at 37° C.

After ligation, beads were washed using 200 μL of 1× B&W buffer and resuspended in 50 μL of nuclease-free H$_2$O. 10 μL of resuspended beads were aliquoted for qPCR and stored at 4° C.

The remaining 40 μL of resuspended beads was subjected to digestion. 1 μL of 10 μM connector, 5 μL 10× CutSmart Buffer (NEB B2704S), and 4 µL EcoRV-HF was added to the beads and incubated at 37° C. for 2 hours.

Reactions were washed using 200 µL of 1× B&W buffer and resuspended in 40 µL of nuclease-free $H_2O$. 10 µL of resuspended beads were aliquoted for qPCR and stored at 4° C.

Ligation was repeated on the remaining 30 µL of beads as above, except using 14 µL of 100 nM connector, 1 µL of 400 U/µL ligase, and incubating at 37° C. for 15 minutes.

After ligation, beads were washed using 200 µL of 1× B&W buffer and resuspended in 30 µL of nuclease-free $H_2O$. 10 µL of resuspended beads were aliquoted for qPCR and stored at 4° C.

qPCR from magnetic beads: qPCR of all aliquots was performed simultaneously. 3 µL from each 10 µL aliquot was combined with 3.6 µL of nuclease-free $H_2O$, 1.2 µL of forward and reverse primers (each, 10 µM; Table 1), 1 µL Evagreen dye (Biotium #31000), and 10 µL 2× FastStart DNA Probes Essential Master Mix (Roche #06 402 682 001).

qPCR started with an initial enzyme activation of 95° C. for 600 sec; followed by 40 cycles of 95° C. for 10 sec melting, 62° C. for 1 sec annealing, and 72° C. for 1 sec extension; the three processes to obtain Evagreen melting curves were at 95° C. for 10 sec, 60° C. for 60 sec, and 97° C. for 1 sec.

Gel electrophoresis of qPCR reactions: A 10% polyacrylamide gel was made by combining 12.5 mL 20% acrylamide (in 7 M urea), 12.5 mL TBE dilution buffer (in 7 M urea), 100 µL 10% APS, and 25 µL TEMED. 20 µL of each qPCR reaction was mixed thoroughly with 20 µL 2× loading dye (95% formamide, 10 mM EDTA, 0.025% BB) and denatured at 95° C. for 5 minutes. After denaturation, the temperature was ramped down to 25° C. at the rate of 0.1° C./s. The denatured product was loaded into the gel and run at the voltage of 400 V for 2 h. After running, the gel was stained in 10 µL of 10000× SybrGold (Invitrogen, S11494) diluted with 100 mL $H_2O$. The oligonucleotide fragments from Bhadra and Ellington (Bhadra and Ellington, 2014) were used as the DNA ladder.

Example 5—Split-and-Pool Method

Figure 11A:
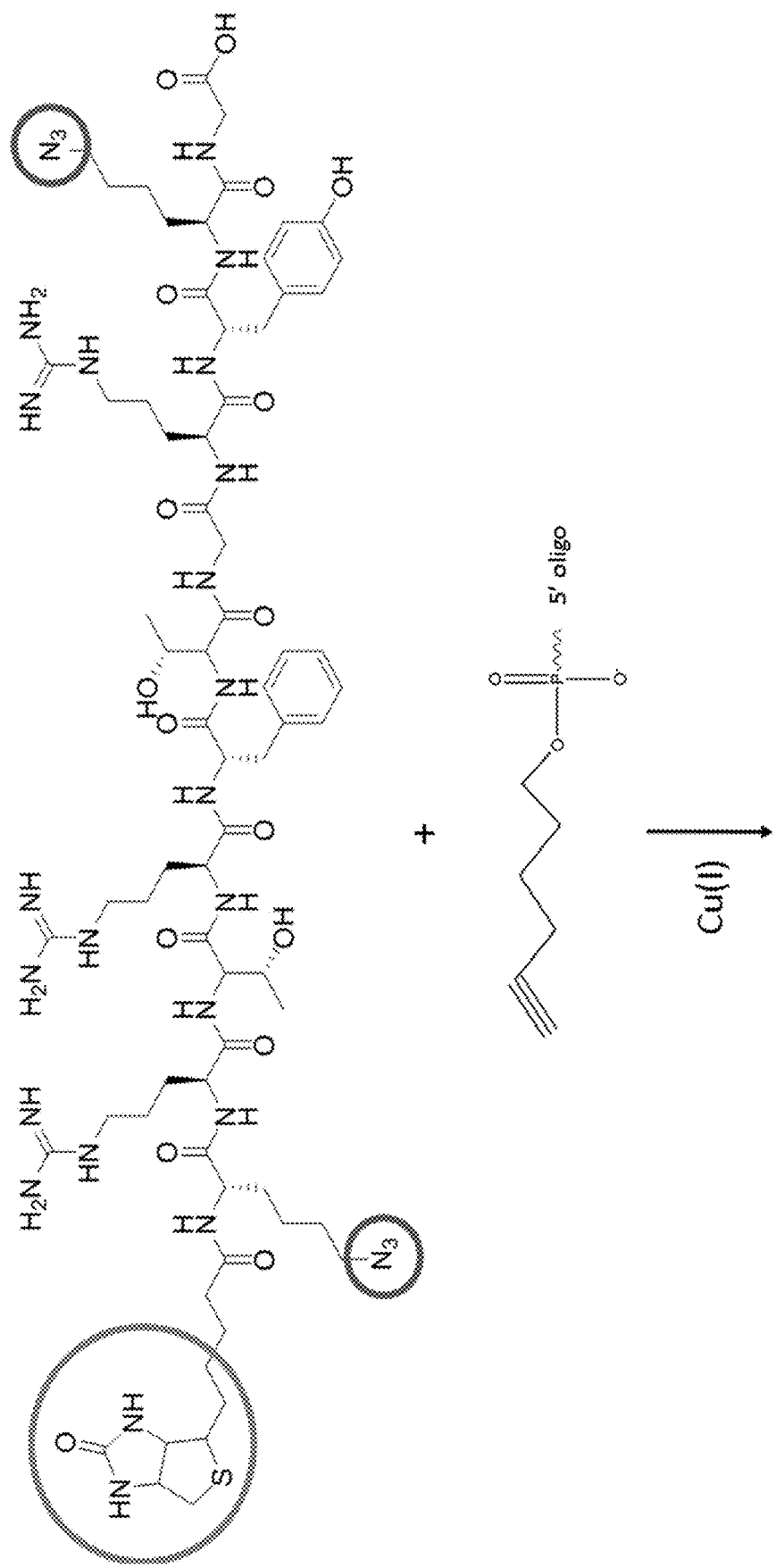
FIGS. 11A-11B: (A) Double label azidolysine peptide design. (SEQ ID NO: 49) (B) Double label azidolysine peptide with conjugated oligos.
Figure 11B:
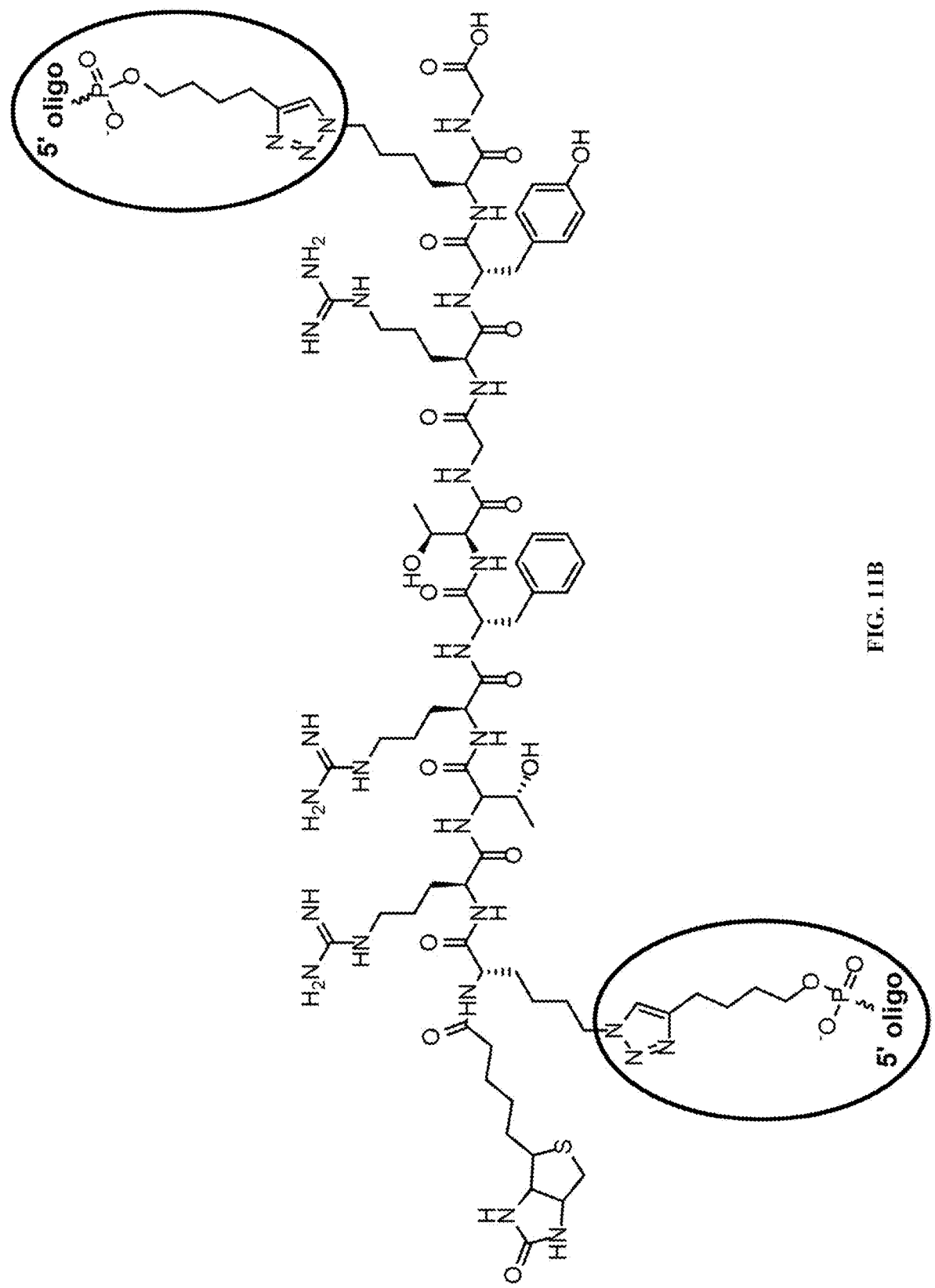
Figure 12A:
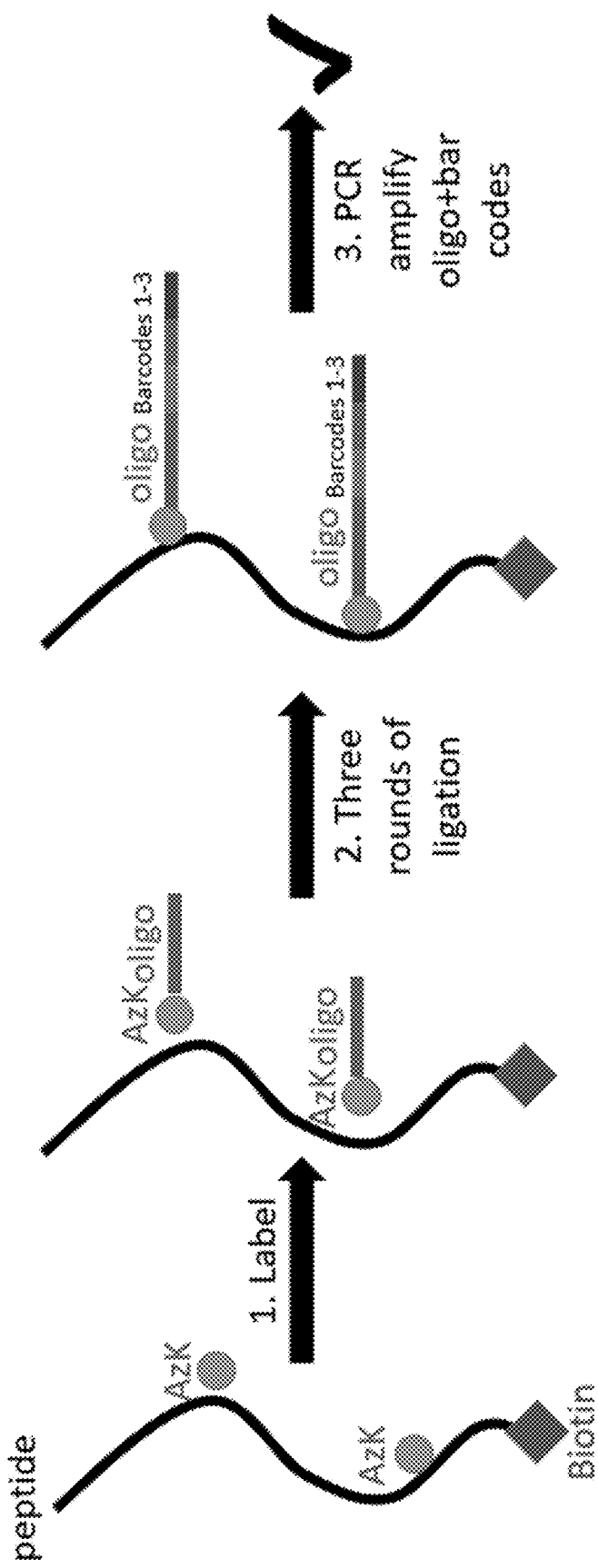
Figure 12C:
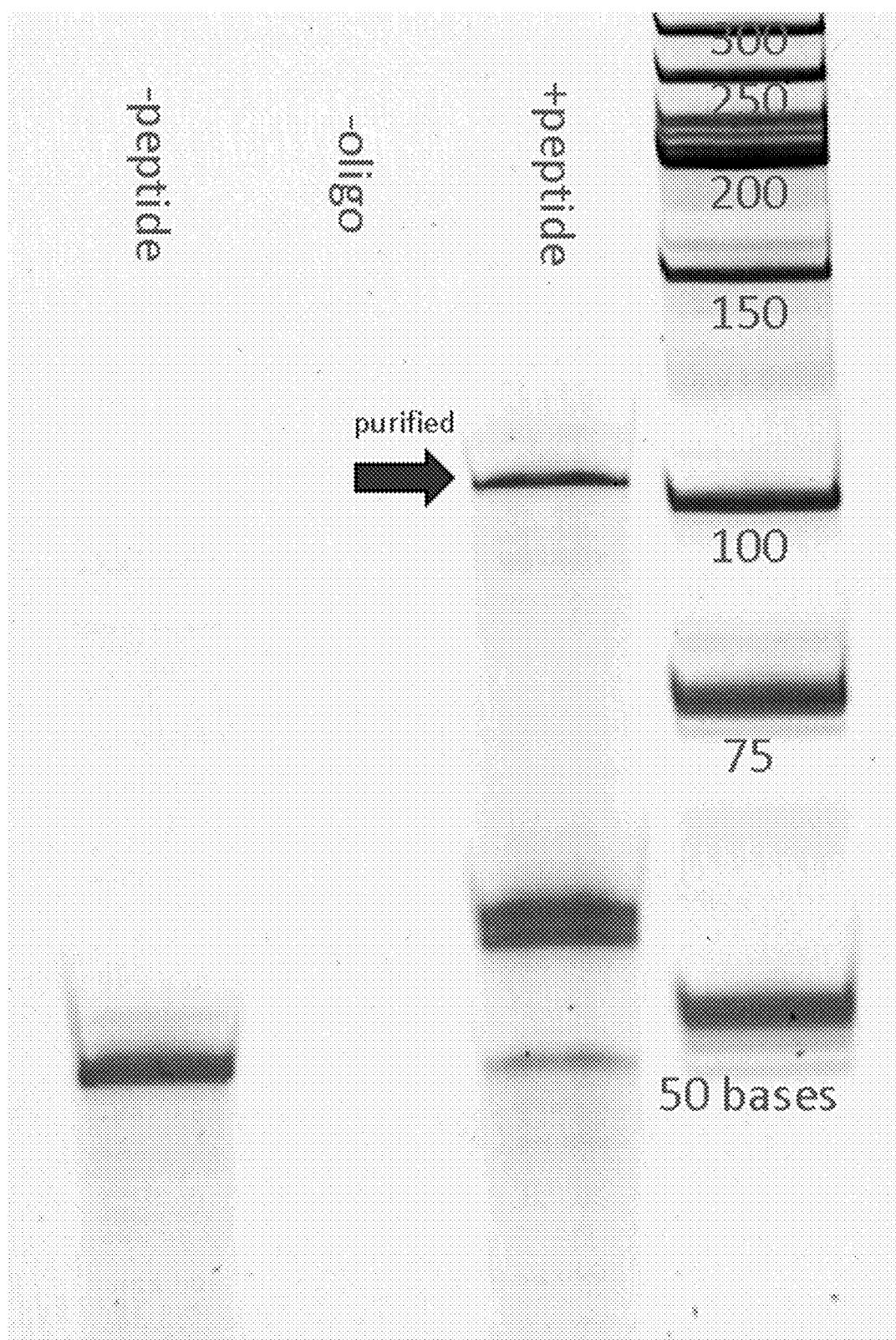
Figure 12D:
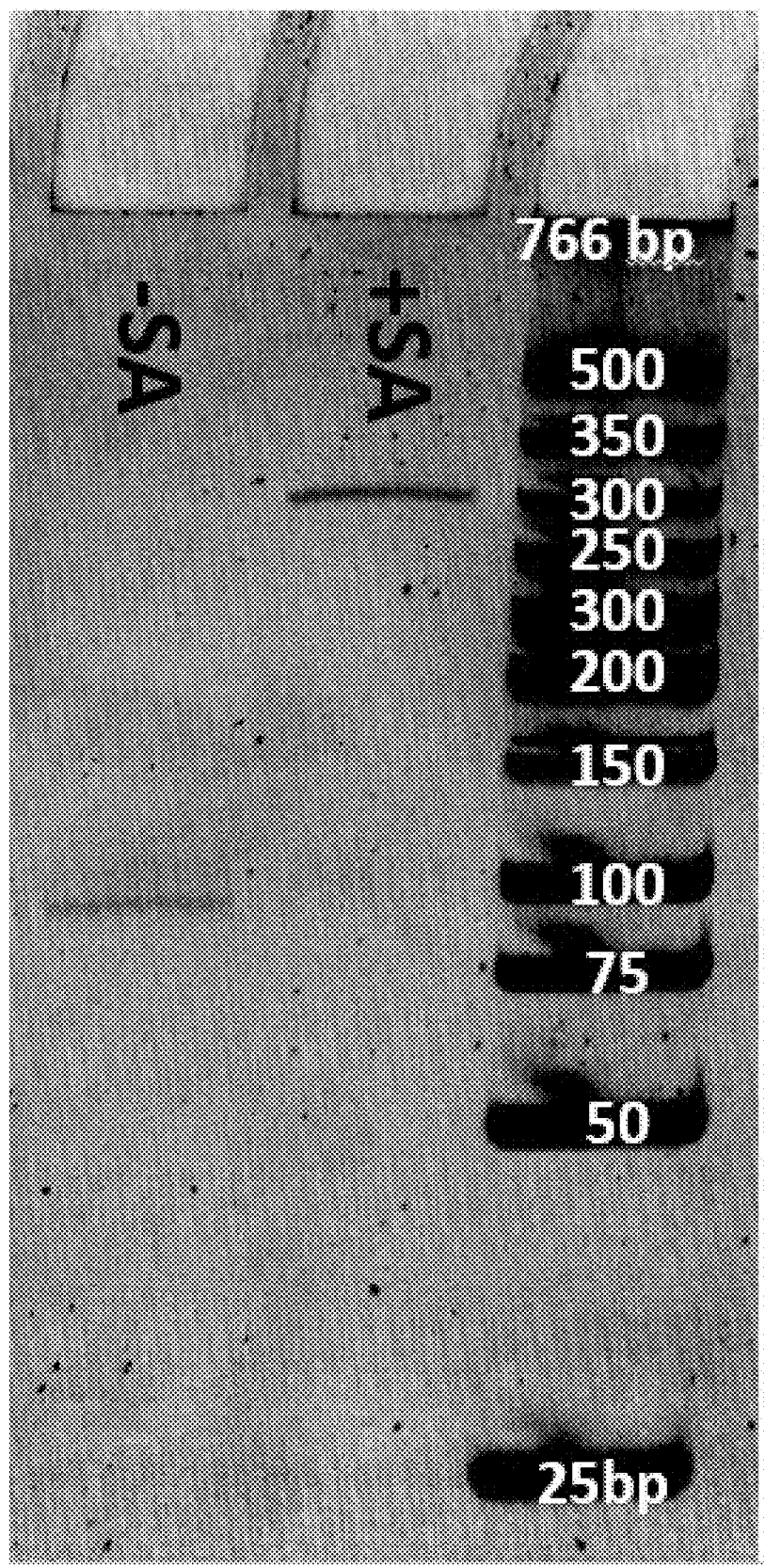
Figure 13A:
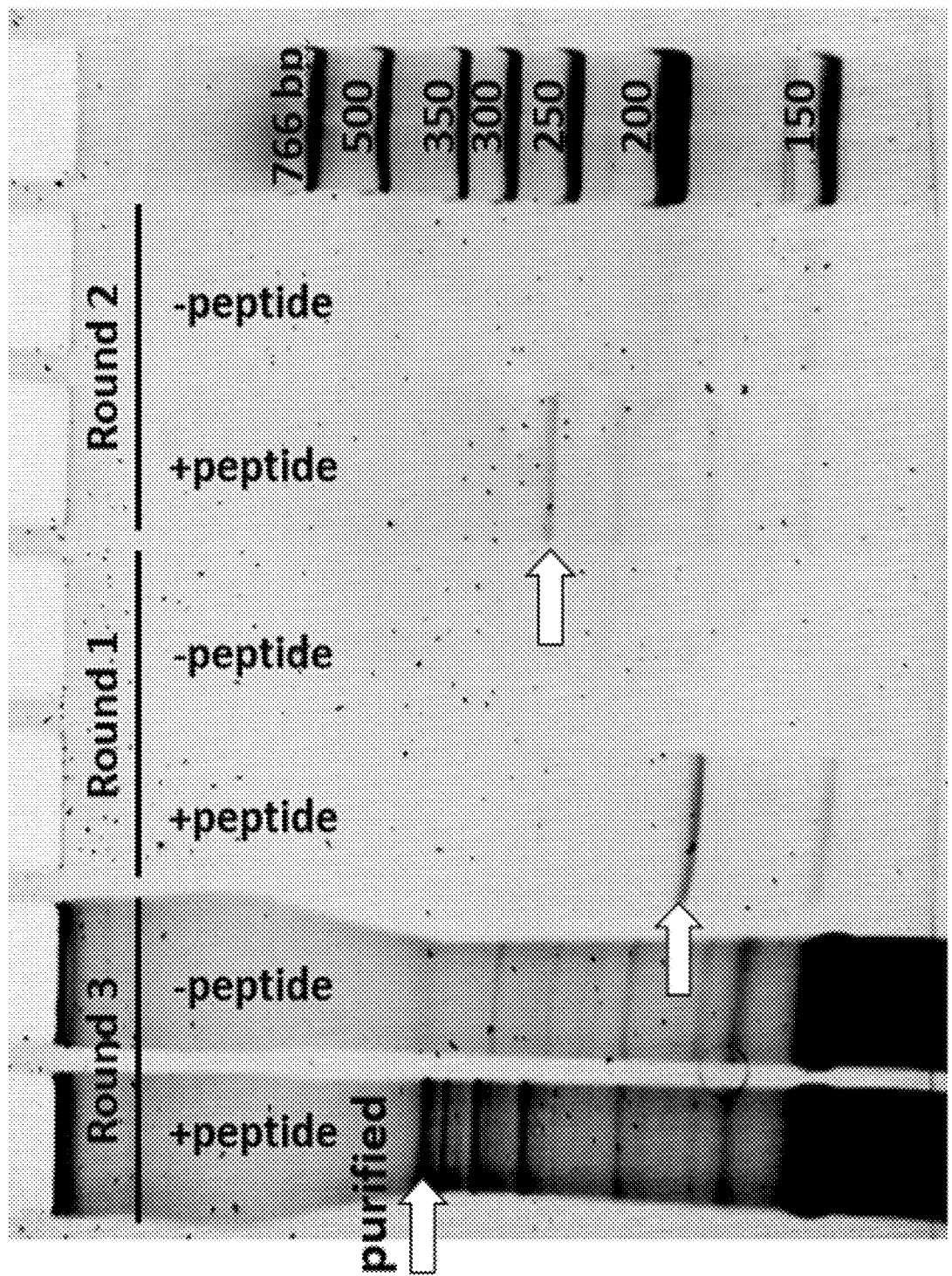
FIGS. 13A-B: (A) Each round of ligation by PAGE gel analysis. (B) PCR of double labeled peptide.
Figure 13B:
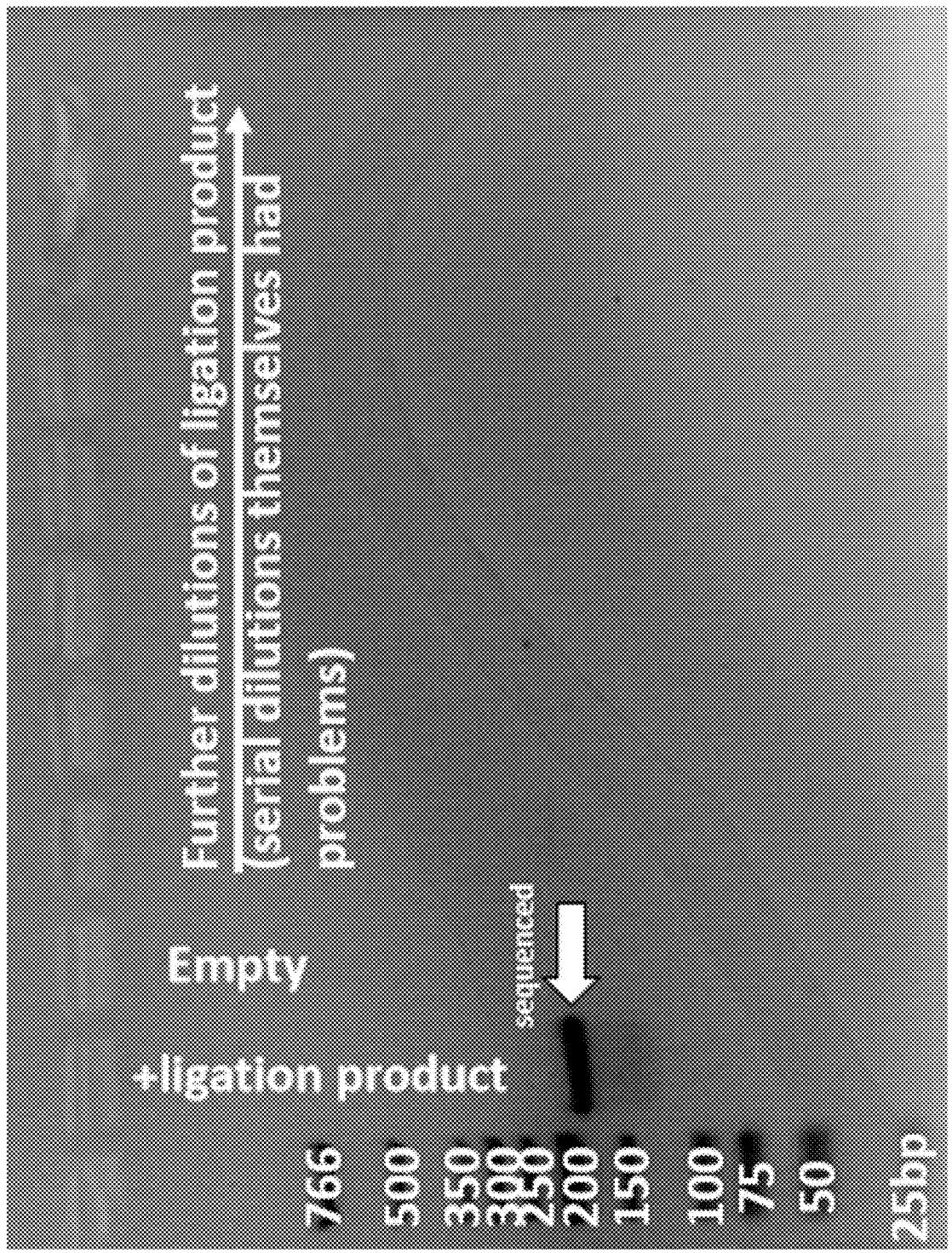

To perform the split-and-pool method, a double label azidolysine peptide was designed and conjugated to oligonucleotides (FIG. 11). To obtain a control (non-split-and-pool) labeling and ligation method to demonstrate that the peptides can be labeled with oligonucleotides and barcoded, the double labeled peptide was isolated by PAGE (FIG. 12C). The presence of peptide was confirmed using a streptavidin shift assay (FIG. 12D). Three rounds of barcode ligation (barcode designs in FIG. 12B) were performed on the labeled peptide and the product was isolated (FIG. 13A). Individual ligation can be seen in FIG. 13A by aliquoting samples after each ligation. Next, PCR was performed to amplify the ligated barcodes and confirm the sequence (FIG. 13B). This product was Sanger sequenced to confirm all three barcodes were correctly ligated.

In more detail, the ligation protocol comprised pre-annealing each round's linker+barcode, ligation of the pre-annealed Round 1 linker-barcode pair to hexynyl oligo by T4 ligase, incubation with Round 1 blocker, repeating ligation & blocking for rounds 2 & 3, and deactivation of the ligase. Barcode, linker, and blocker designs are in FIG. 12B.

Figure 14B:
Figure 14C:
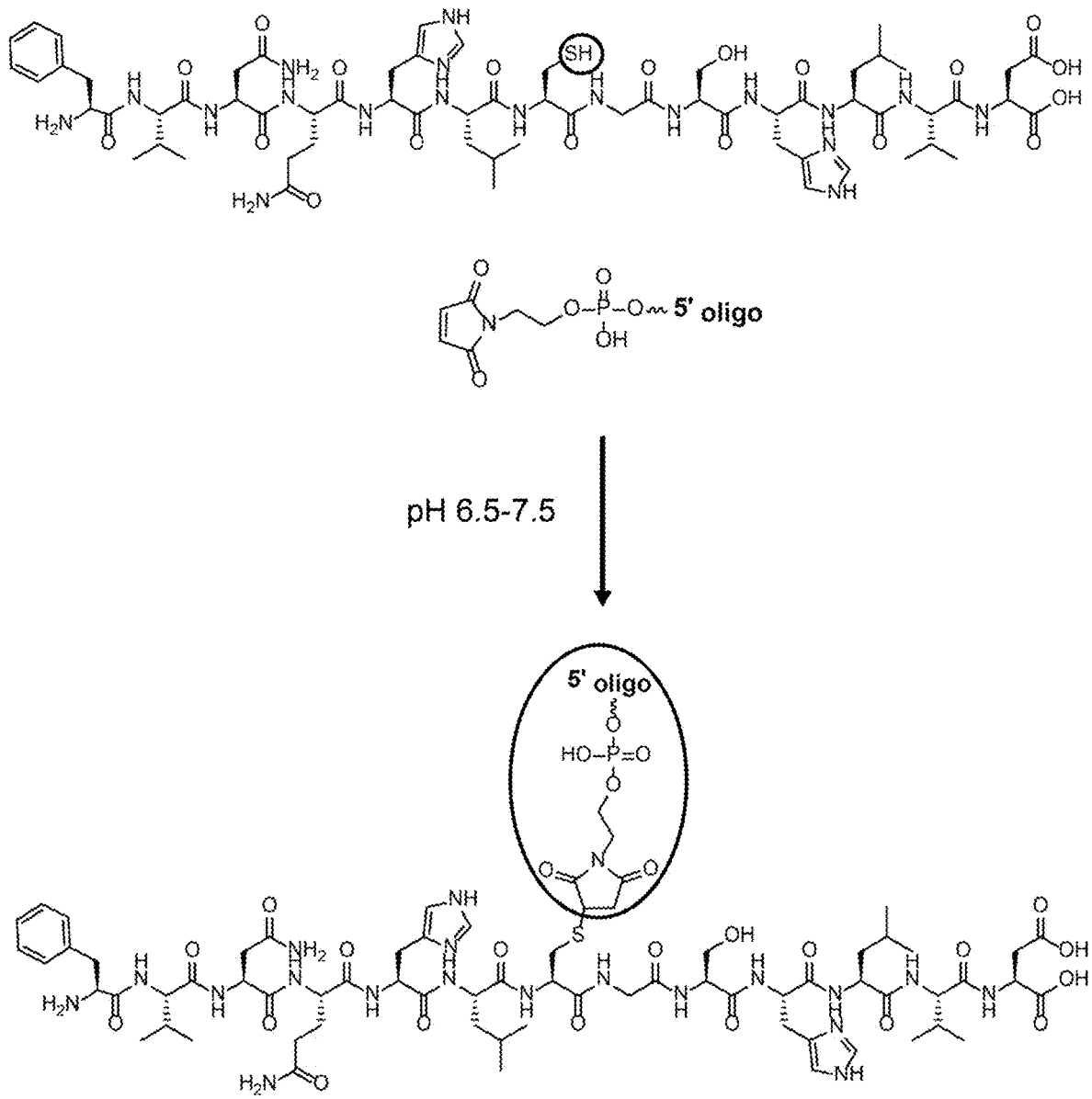
Figure 14C:
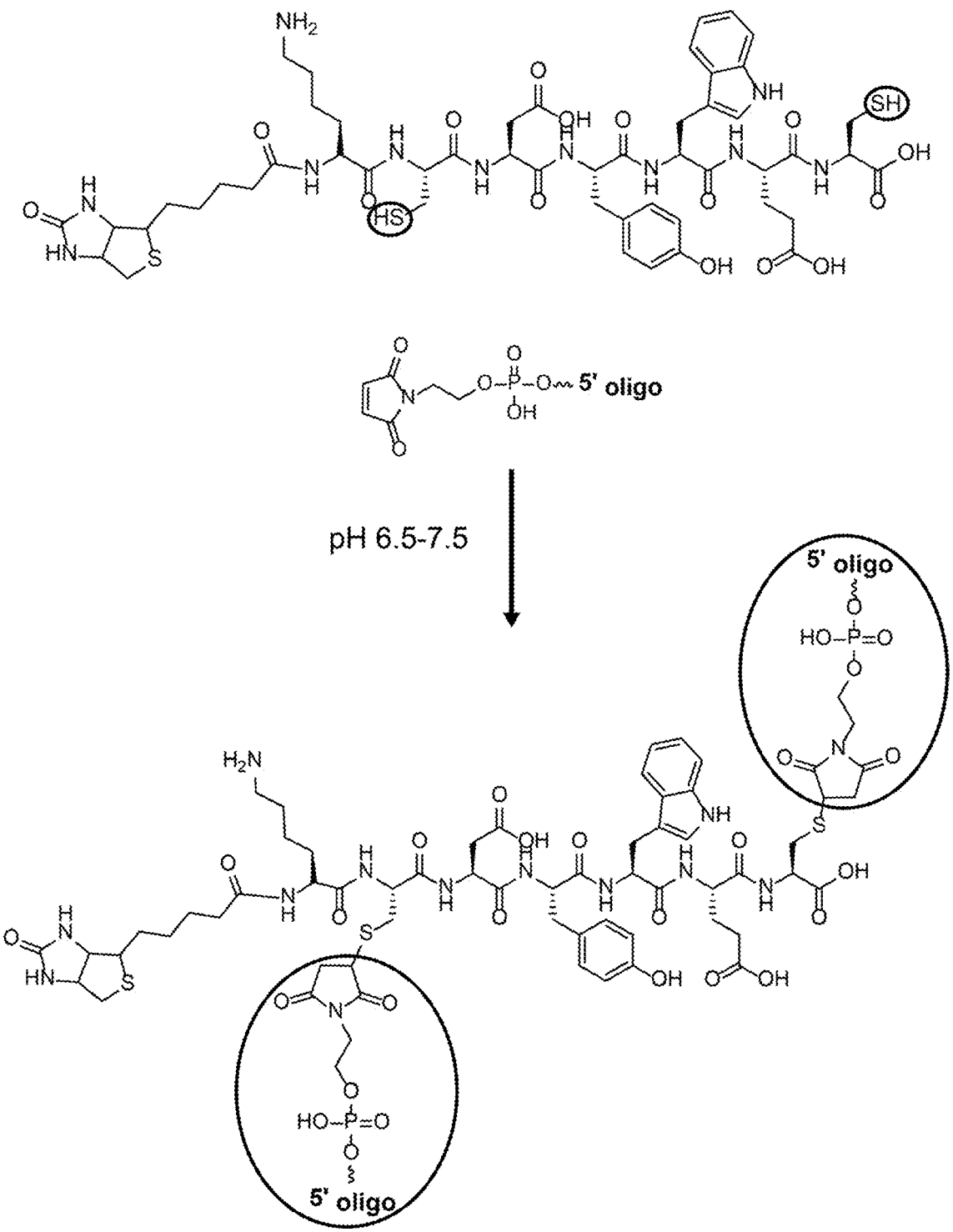
Figure 15A:
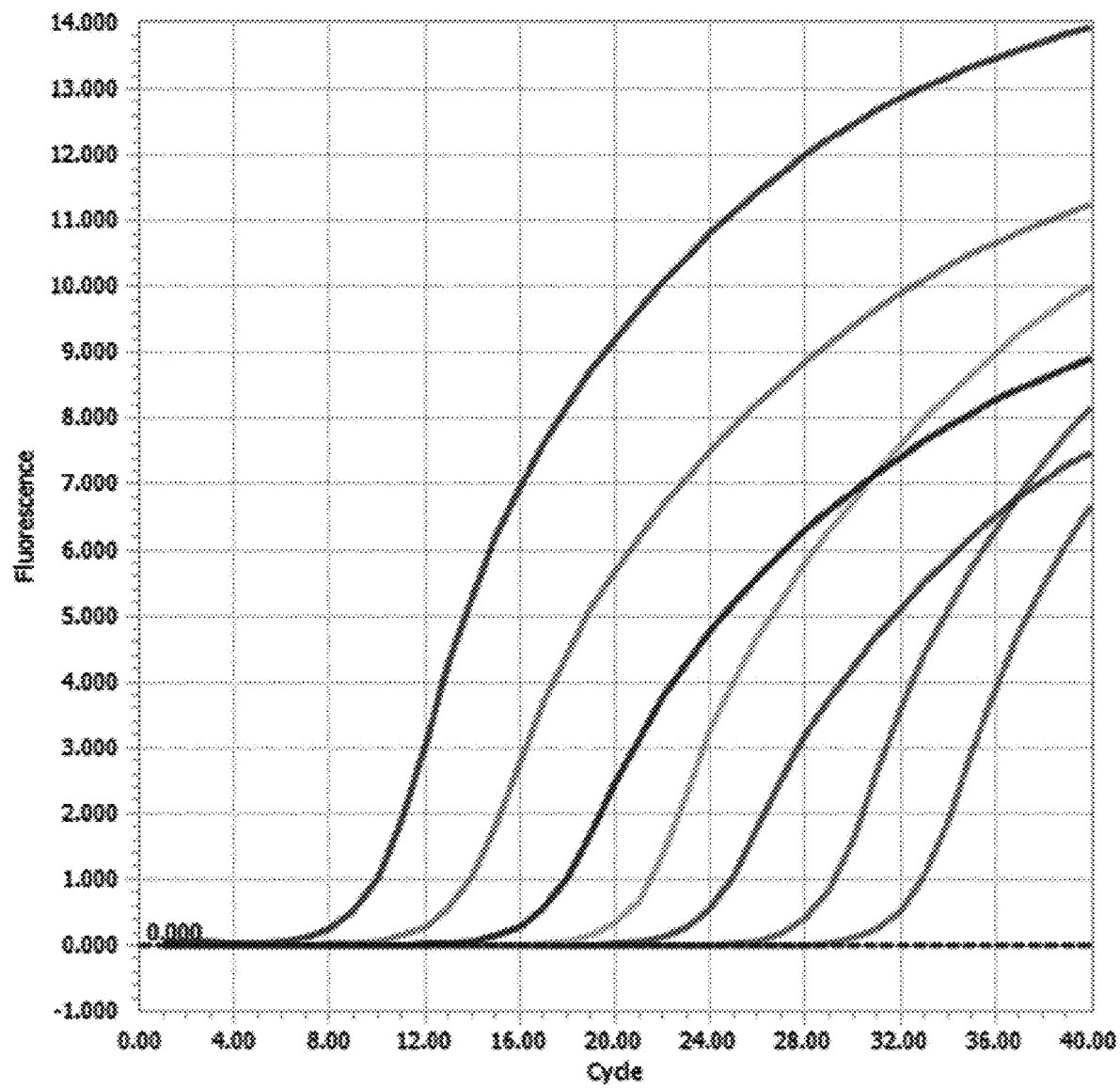
FIGS. 15A-15C: (A) Serially diluted qPCR of purified product. (B) Amplification and Sanger sequencing of purified product. (SEQ ID NOS: 52-55) (C) Sequence quality curves.
Figure 15A:
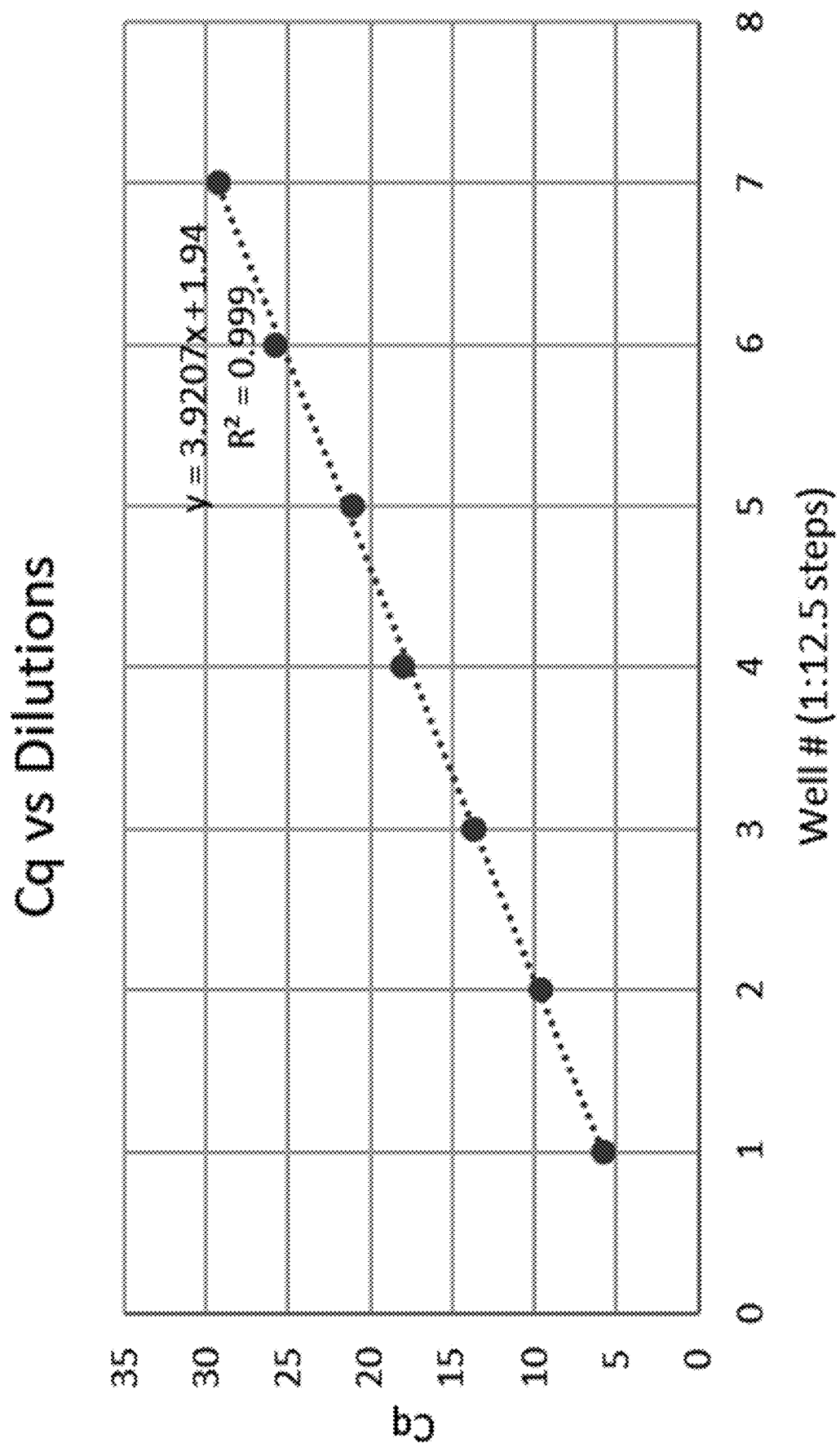
Figure 15A:
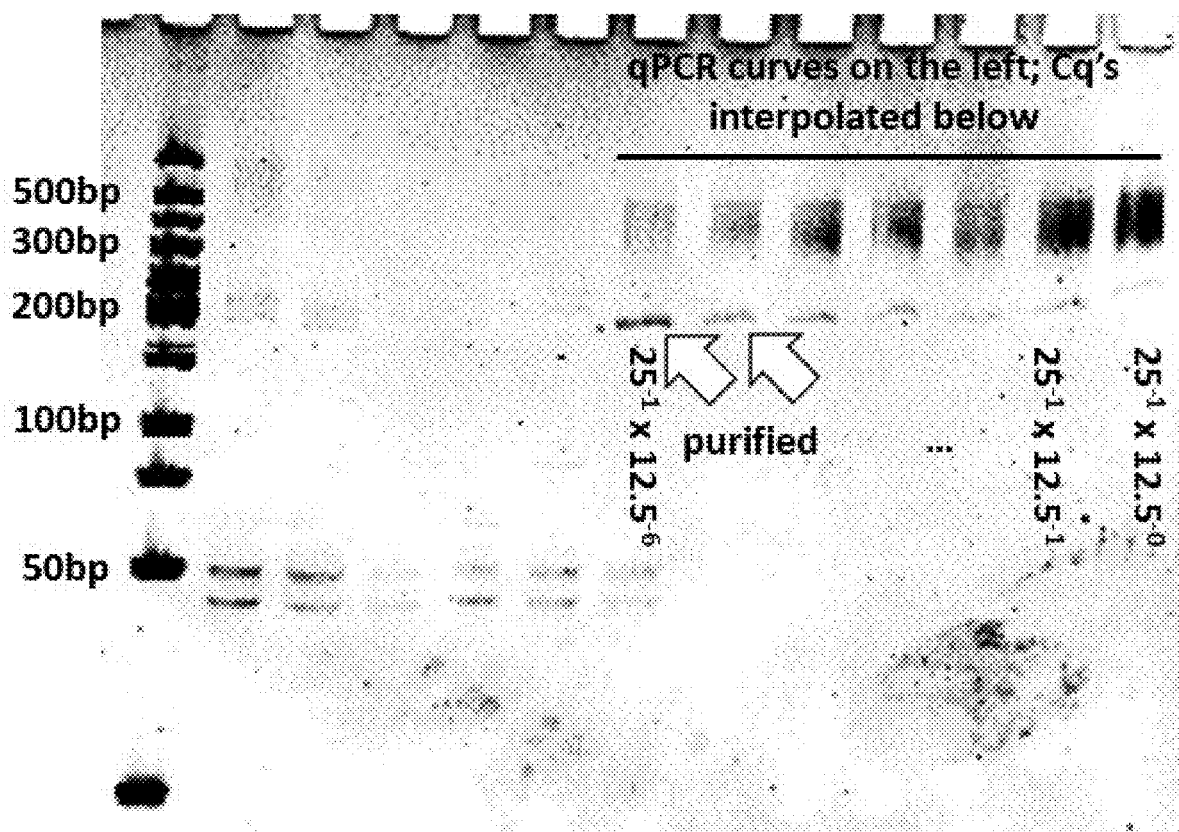

The above experiments were repeated using a split-and-pool of three rounds, with ten barcodes per round. Barcode designs are in FIG. 14A; all linker, blocker, and primer components of the experiment remained identical to FIG. 12B. After three rounds of split-and-pool ligation were performed on purified doubly-labeled peptide and, separately, on hexynyl oligo as a single-label control. Using a doubly-labeled peptide with the 10×10×10 split-pool allows for up to $10^3=1000$ distinct peptides to be identified. Products from both split-and-pool ligations were run on a PAGE gel to confirm size (FIG. 14B) and were PAGE purified. Correct doubly labeled & fully barcoded peptide≈2×46+2× 2×45+2×48=368 bases. The thick band around 150 bases corresponds to the three ligated barcodes not attached to a peptide=45+45+48=138. The top bands were purified. FIG. 15A shows serially diluted qPCR of the purified product. The serial dilution isolates just a few hundred labeled peptides whose barcodes can be sequenced. The linear Cq curve shows the serial dilution was taking place as intended.

Figure 15B:
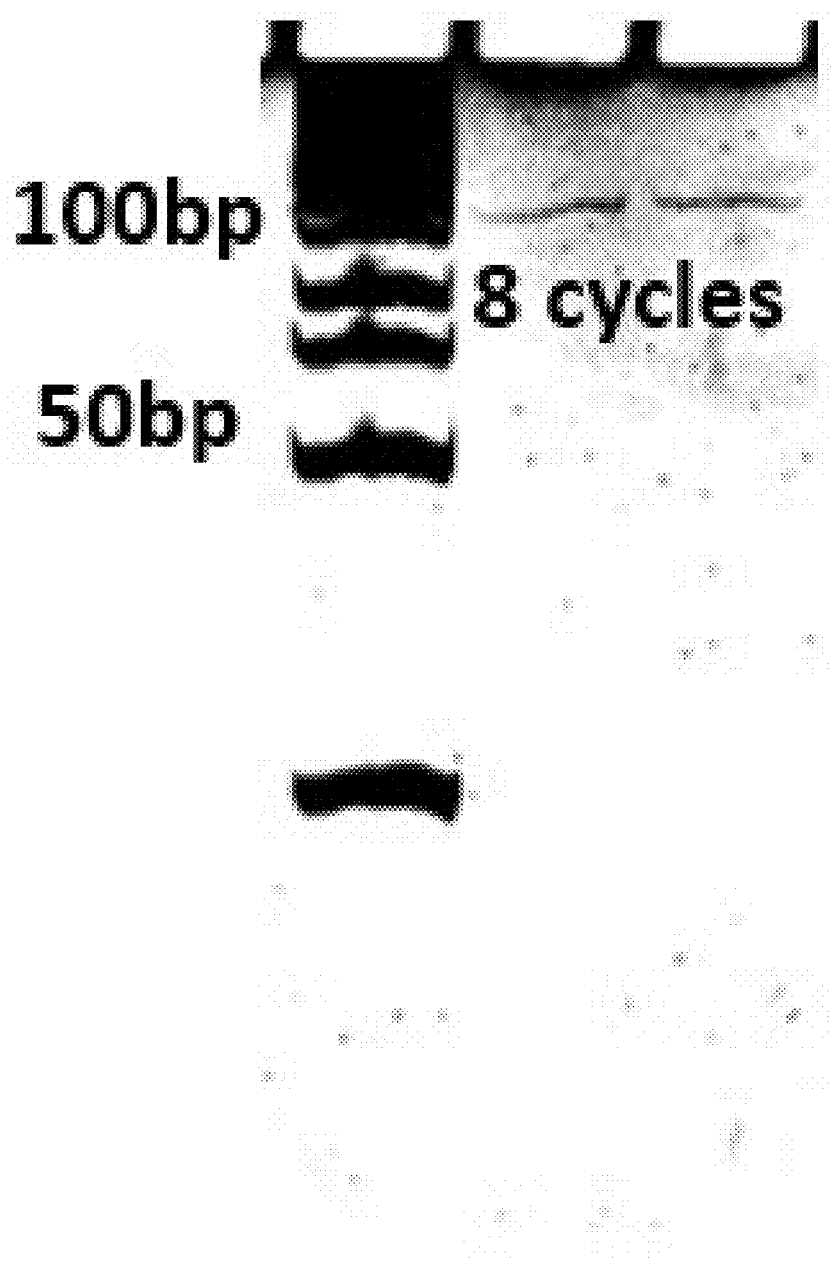
Figure 15C:
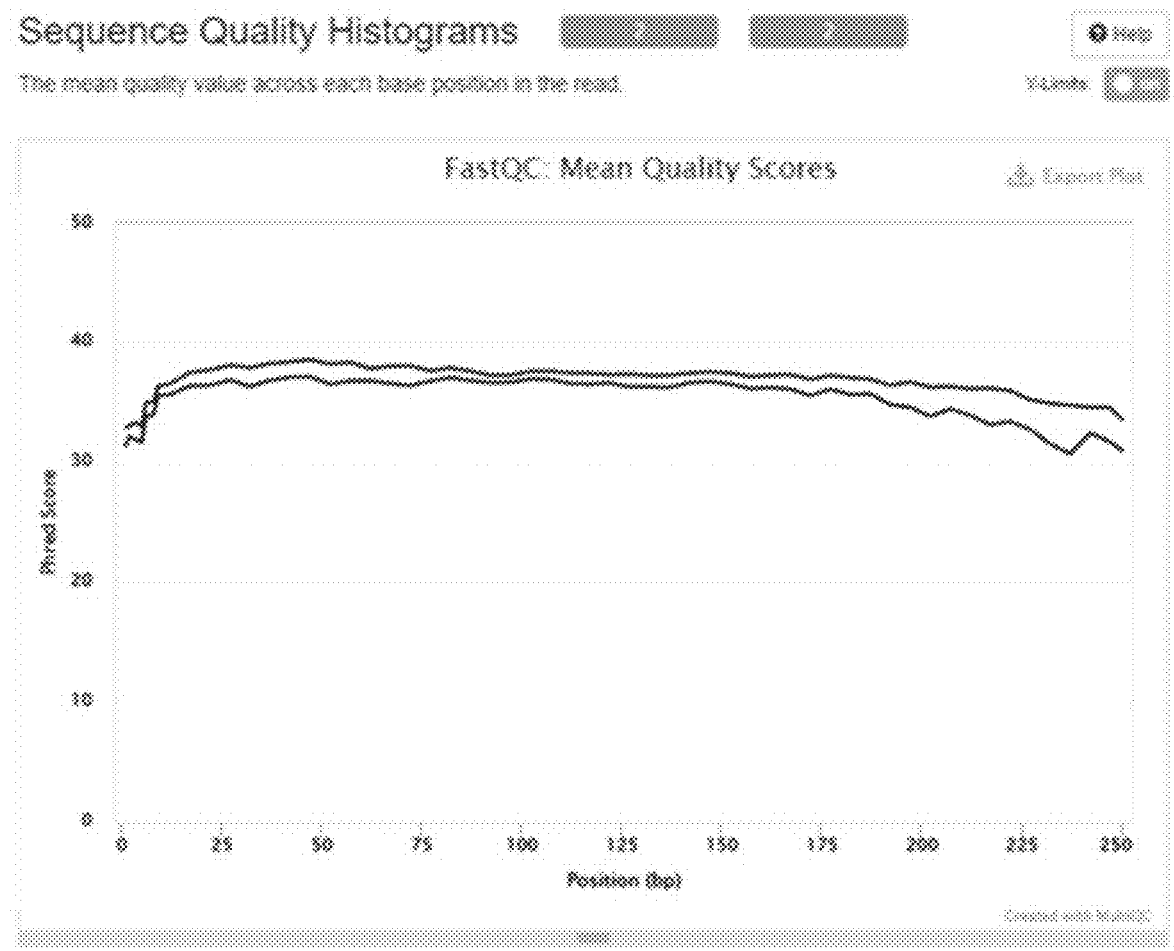
Figure 15C:
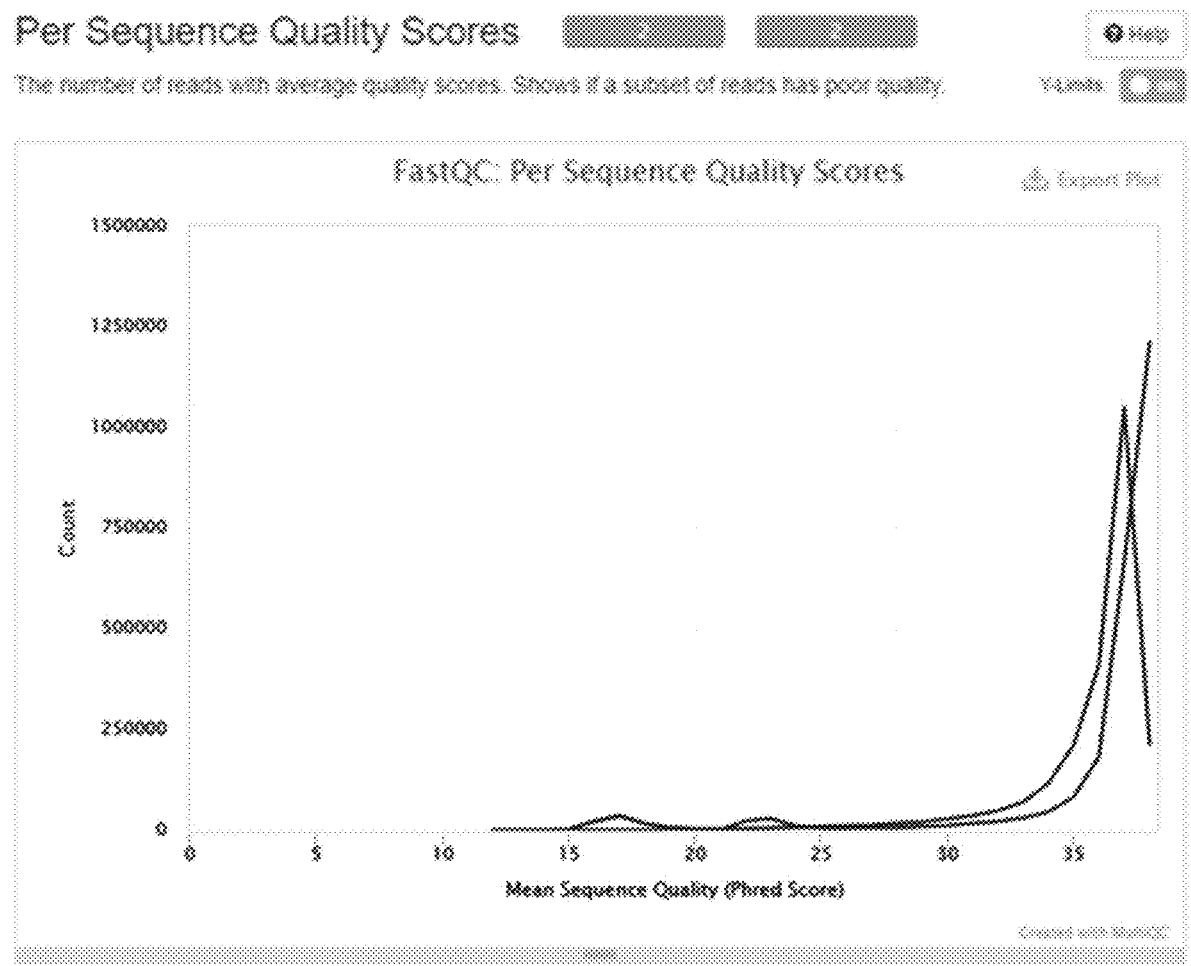

FIG. 15B shows amplification & sanger sequencing of the purified product showing the combinatorial barcodes attached to the peptide. The extra N inserted in the barcode/ UMI regions of the Sanger sequences is an artifact that is not unexpected. Individual molecules were then sequenceed on an Illumina platform and obtained good reads were obtained, i.e. barcodes were captured from labeled peptides. The sequencing had good quality curves and the vast majority of reads align essentially perfectly to their barcode template.

Figure 16A:
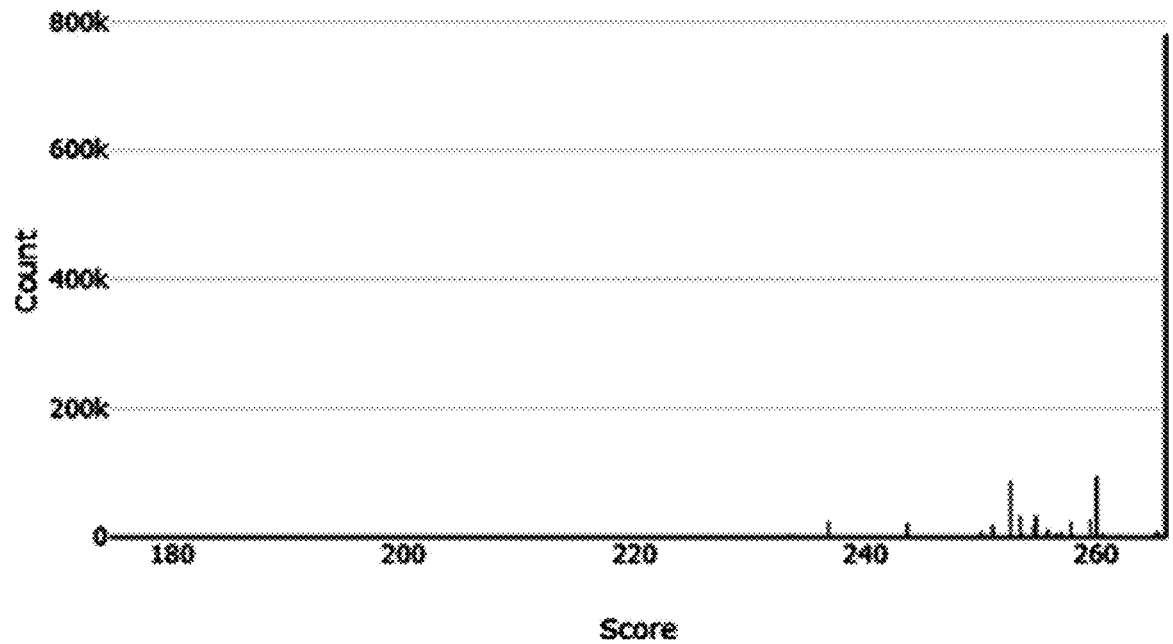
Figure 16B:
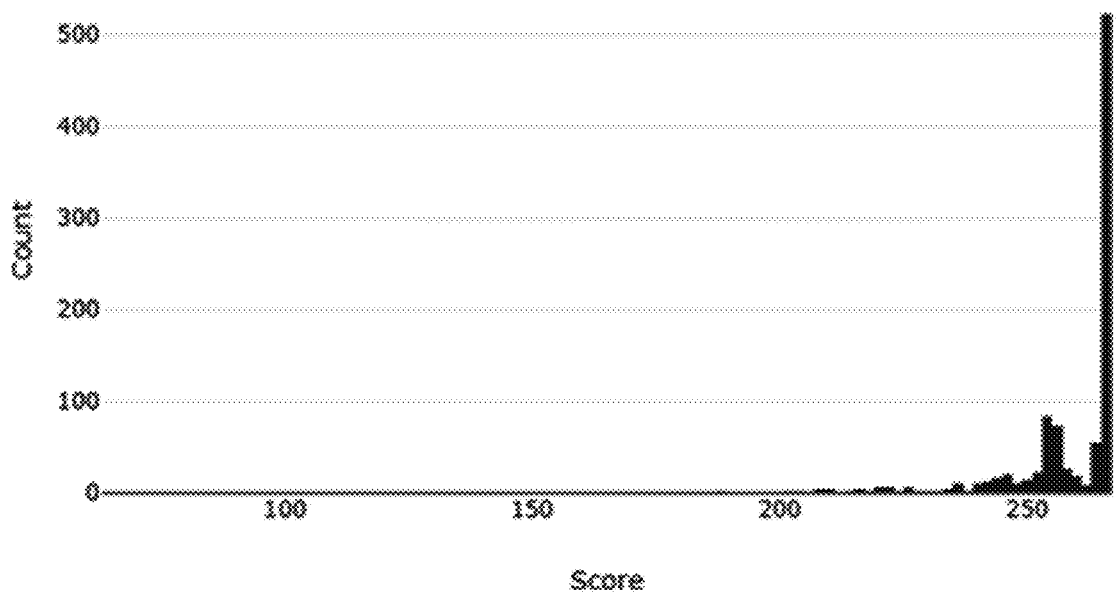
Figure 16D:
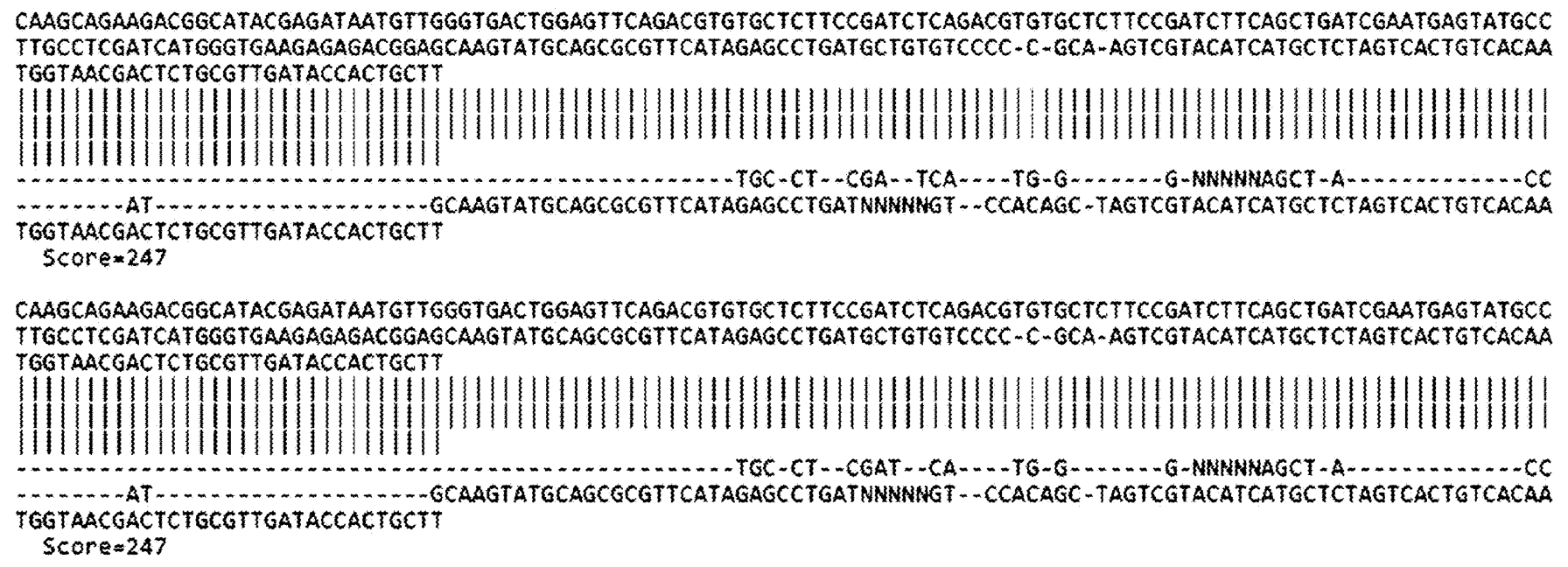

The barcodes were aligned to the reads. The reverse compliment reads were reverse complimented. FIG. 16A shows distribution of the alignment scores with a higher score being better. FIG. 16B shows the best alignment for each combination.

Example 6—Cysteine Labeling

Figure 14D:
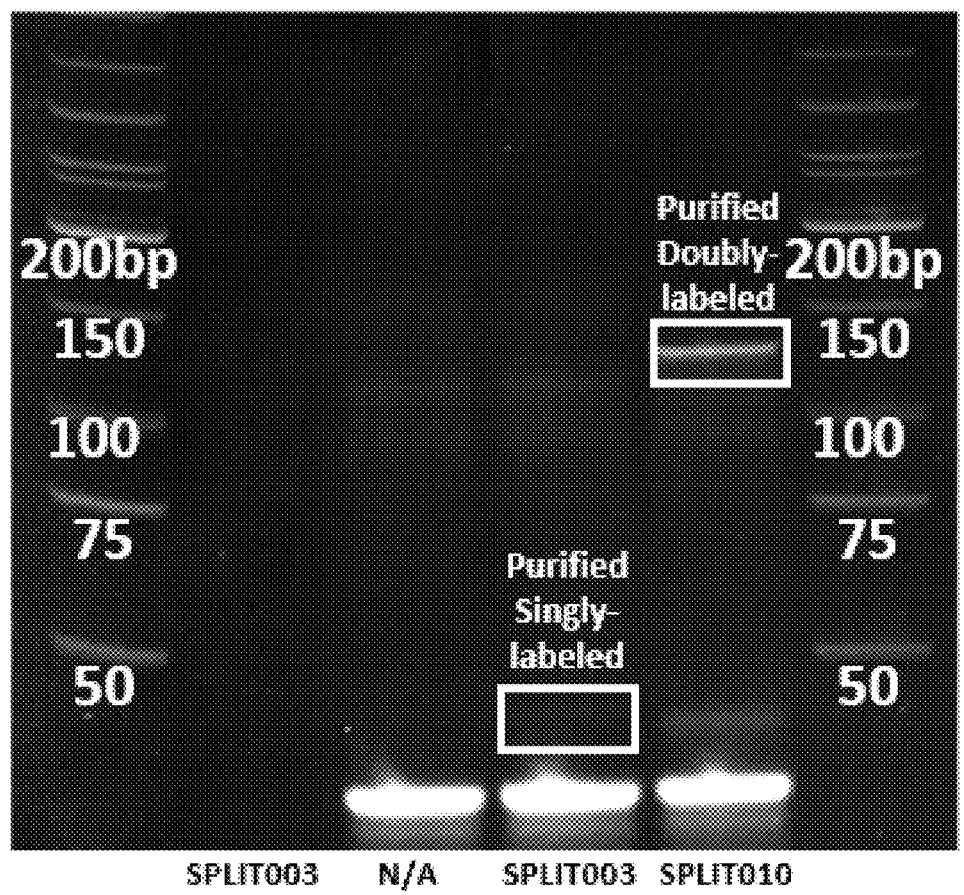
Figure 14E:
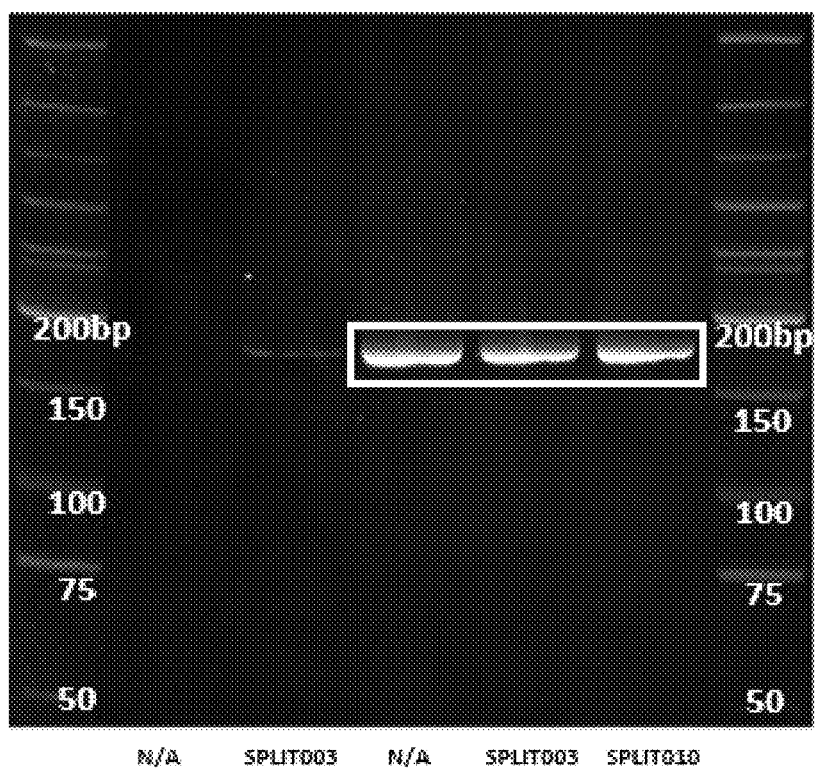

It was demonstrated that cysteine-containing peptides can be labeled with maleimide modified oligonucleotides (FIG. 14D). After purifying these products, three rounds of ligation were performed as above (non-split-and-pool) these successful ligations were confirmed via PCR (FIG. 14E).

All of the methods disclosed and claimed herein can be made and executed without undue experimentation in light of the present disclosure. While the compositions and methods of this disclosure have been described in terms of preferred embodiments, it will be apparent that variations may be applied to the methods and in the processes or in the sequence of processes of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

REFERENCES

The following references, to the extent that they provide procedural or other details supplementary to those set forth herein, are specifically incorporated herein by reference.

Balister, Handbook of Large-Scale Random Networks (eds. Bollobas, B., Kozma, R. & Miklós, D.) 18, 117-142 (Springer Berlin Heidelberg, 2008).

Bhadra & Ellington, *Nucleic Acids Res.* 42, e58-e58 (2014).

Bollobás, *Random graphs*. (Cambridge University Press, 2001).

Buschmann, & Bystrykh, *BMC Bioinformatics* 14, 272 (2013).
Erdös & Rényi. *Acta Math. Acad. Sci. Hung.* 12, 261-267 (1964).
Gansner & North, *Softw. Pract. Exp.* 30, 1203-1233 (2000).
Harary, *Graph theory*. (Perseus Books, 2001).
Hernandez, *New J. Chem.* 41, 462-469 (2017).
Kamada & Kawai, *Inf. Process. Lett.* 31, 7-15 (1989).
Kingman, *Poisson processes*. (Clarendon Press; Oxford University Press, 1993).
Margulies et al. *Nature,* 437, 376-380 (2005).
Penrose, *Random geometric graphs*. (Oxford University Press, 2003).
Pirrung, *Angew. Chem. Int. Ed.* 41, 1276-1289 (2002).
Schaus, *Nat. Commun.* 8, (2017).
Shendure, et al. *Nature* 550, 345-353 (2017).
Soderberg, et al. *Nat. Methods* 3, 995-1000 (2006).
Soni and Meller, *Clin Chem* 53: 1996-2001 (2007).
Swaminathan, *PLOS Comput. Biol.* 11, e1004080 (2015).

What is claimed is:

1. A method for uniquely labeling one or more peptides comprising:
   (a) obtaining a sample comprising a plurality of peptides free in solution;
   (b) attaching oligonucleotide tags comprising unique amino acid-specific barcodes to the plurality of peptides, thereby generating a first plurality of tagged-peptides free in solution;
   (c) splitting the first plurality of tagged-peptides into three or more compartments;
   (d) labeling the first plurality of tagged-peptides with a first compartment-specific oligonucleotide tag, thereby generating a second plurality of tagged-peptides free in solution;
   (e) pooling the second plurality of tagged-peptides from the three or more compartments, and splitting the second plurality of tagged-peptides into three or more compartments; and
   (f) attaching a second compartment-specific oligonucleotide tag to the second plurality of tagged-peptides, thereby obtaining a plurality of uniquely labeled peptides free in solution.

2. The method of claim 1, further comprising another one or more rounds of pooling the uniquely labeled peptides, splitting the uniquely labeled peptides, and attaching additional compartment-specific oligonucleotide tags to obtain further uniquely labeled peptides.

3. The method of claim 1, wherein the unique amino acid-specific barcodes are specific for lysine, cysteine, glutamic acid, aspartic acid, tyrosine, tryptophan, or histidine.

4. The method of claim 1, wherein amino acids in the plurality of peptides free in solution comprise post-translationally modified side chains.

5. The method of claim 4, wherein the post-translationally modified side chains comprise phosphorylation, glycosylation, methylation, citrullination, or any combination thereof.

6. The method of claim 1, wherein the unique amino acid-specific barcodes comprise a functional group to attach the unique amino acid-specific barcodes to amino acids in the plurality of peptides free in solution.

7. The method of claim 6, wherein the functional group is selected from the group consisting of a succinimidyl ester, an iodoacetamide, a maleimide, amines, a 4-phenyl-3H-1,2,4-triazole-3,5 (4H)-dione (PTAD), a 2,4-dinitrobenzenesulfenyl chloride, and a thiol.

8. The method of claim 1, further comprising generating the plurality of peptides free in solution by digesting a protein with an enzyme.

9. The method of claim 8, wherein the digesting is site-specific.

10. The method of claim 8, wherein the enzyme is trypsin.

11. The method of claim 8, wherein the digesting the protein does not remove an N-terminal amino acid.

12. The method of claim 1, wherein the oligonucleotide tags comprising the unique amino acid-specific barcodes, the first compartment-specific oligonucleotide tags, and/or the second compartment-specific oligonucleotide tags are single-stranded.

13. The method of claim 1, wherein the first compartment-specific oligonucleotide tag or the second compartment-specific oligonucleotide tag is single-stranded.

14. The method of claim 1, wherein the labeling or the attaching comprises enzymatic ligation.

15. The method of claim 14, wherein the enzymatic ligation comprises blunt-end ligation.

16. The method of claim 1, further comprising:
   (a) performing next-generation sequencing on the oligonucleotide tags comprising the unique amino acid-specific barcodes, the first compartment specific oligonucleotide tag, and the second compartment-specific oligonucleotide tag; and
   (b) obtaining an amino acid pattern for a single peptide from the next-generation sequencing and comparing the amino acid pattern to a proteome of an organism to identify the uniquely labeled peptide.

17. The method of claim 1, wherein the labeling or the attaching comprises chemical ligation.

18. The method of claim 1, wherein the uniquely labeled peptide comprises a unique ligated barcode.

19. The method of claim 1, further comprising counting a number of amino acids of an amino acid type of the uniquely labeled peptide.

20. The method of claim 1, wherein the first plurality of tagged-peptides free in solution of (c) or the second plurality of tagged-peptides free in solution in (e) is split into 96 or more compartments.

* * * * *

SEQUENCE LISTING

```
<160> NUMBER OF SEQ ID NOS: 59

<210> SEQ ID NO 1
<211> LENGTH: 90
<212> TYPE: DNA
<213> ORGANISM: Artificial sequence
<220> FEATURE:
<223> OTHER INFORMATION: Synthetic probe

<400> SEQUENCE: 1
tttttttttt tttttttttt tttttttttt tttttttttt tttttttttt ttttttttc       60 gcttcaggta gtagtacgtc tatgtatgat                                       90

<210> SEQ ID NO 2
<211> LENGTH: 90
<212> TYPE: DNA
<213> ORGANISM: Artificial sequence
<220> FEATURE:
<223> OTHER INFORMATION: Synthetic probe

<400> SEQUENCE: 2
atcctgtagc attaatactc tcgcagcaca acggtactt tttttttttt tttttttttt       60
tttttttttt tttttttttt tttttttttt                                       90

<210> SEQ ID NO 3
<211> LENGTH: 18
<212> TYPE: DNA
<213> ORGANISM: Artificial sequence
<220> FEATURE:
<223> OTHER INFORMATION: Synthetic connector

<400> SEQUENCE: 3
ctacaggata tcatacat                                                    18

<210> SEQ ID NO 4
<211> LENGTH: 22
<212> TYPE: DNA
<213> ORGANISM: Artificial sequence
<220> FEATURE:
<223> OTHER INFORMATION: Synthetic primer

<400> SEQUENCE: 4
cgcttcaggt agtagtacgt ct                                               22

<210> SEQ ID NO 5
<211> LENGTH: 22
<212> TYPE: DNA
<213> ORGANISM: Artificial sequence
<220> FEATURE:
<223> OTHER INFORMATION: Synthetic primer

<400> SEQUENCE: 5
ccgttgtgct gcgagagtat ta                                               22
```

<210> SEQ ID NO 6
<211> LENGTH: 45
<212> TYPE: DNA
<213> ORGANISM: Artificial sequence
<220> FEATURE:
<223> OTHER INFORMATION: Synthetic nucleic acid

<400> SEQUENCE: 6
caacgtgtgc tcttccgatc ttcagctgat cgaatgagta tgcct            45

<210> SEQ ID NO 7
<211> LENGTH: 30
<212> TYPE: DNA
<213> ORGANISM: Artificial sequence
<220> FEATURE:
<223> OTHER INFORMATION: Synthetic nucleic acid

<400> SEQUENCE: 7
gcttactcat acggaacgga gctagtaccc                              30

<210> SEQ ID NO 8
<211> LENGTH: 30
<212> TYPE: DNA
<213> ORGANISM: Artificial sequence
<220> FEATURE:
<223> OTHER INFORMATION: Synthetic nucleic acid

<400> SEQUENCE: 8
acggagctag tacccgttca tacgtcgcgc                              30

<210> SEQ ID NO 9
<211> LENGTH: 30
<212> TYPE: DNA
<213> ORGANISM: Artificial sequence
<220> FEATURE:
<223> OTHER INFORMATION: Synthetic nucleic acid

<400> SEQUENCE: 9
cgaatgagta tgccttgcct cgatcatggg                              30

<210> SEQ ID NO 10
<211> LENGTH: 30
<212> TYPE: DNA
<213> ORGANISM: Artificial sequence
<220> FEATURE:
<223> OTHER INFORMATION: Synthetic nucleic acid

<400> SEQUENCE: 10
gttcatacgt cgcgcaagta tctcggacta                              30

<210> SEQ ID NO 11
<211> LENGTH: 30
<212> TYPE: DNA
<213> ORGANISM: Artificial sequence
<220> FEATURE:
<223> OTHER INFORMATION: Synthetic nucleic acid

<400> SEQUENCE: 11
aagtatctcg gactatcagc atgtagtacg                              30

<210> SEQ ID NO 12
<211> LENGTH: 30
<212> TYPE: DNA
<213> ORGANISM: Artificial sequence
<220> FEATURE:
<223> OTHER INFORMATION: Synthetic nucleic acid

<400> SEQUENCE: 12
caagtatgca gcgcgttcat agagcctgat                                    30

<210> SEQ ID NO 13
<211> LENGTH: 30
<212> TYPE: DNA
<213> ORGANISM: Artificial sequence
<220> FEATURE:
<223> OTHER INFORMATION: Synthetic nucleic acid

<400> SEQUENCE: 13
tcagcatgta gtacgagatc agtgacagtg                                    30

<210> SEQ ID NO 14
<211> LENGTH: 47
<212> TYPE: DNA
<213> ORGANISM: Artificial sequence
<220> FEATURE:
<223> OTHER INFORMATION: Synthetic nucleic acid

<400> SEQUENCE: 14
agatcaggac agtggtatac cagttgagac gcaactatgg tgacgaa                 47

<210> SEQ ID NO 15
<211> LENGTH: 30
<212> TYPE: DNA
<213> ORGANISM: Artificial sequence
<220> FEATURE:
<223> OTHER INFORMATION: Synthetic nucleic acid

<400> SEQUENCE: 15
agtcgtacat catgctctag tcactgtcac                                    30

<210> SEQ ID NO 16
<211> LENGTH: 22
<212> TYPE: DNA
<213> ORGANISM: Artificial sequence
<220> FEATURE:
<223> OTHER INFORMATION: Synthetic nucleic acid

<400> SEQUENCE: 16
cagacgtgtg ctcttccgat ct                                            22

<210> SEQ ID NO 17
<211> LENGTH: 23
<212> TYPE: DNA
<213> ORGANISM: Artificial sequence
<220> FEATURE:
<223> OTHER INFORMATION: Synthetic nucleic acid

<400> SEQUENCE: 17
ttcgtcacca tagttgcgtc tca                                           23

<210> SEQ ID NO 18
<211> LENGTH: 152
<212> TYPE: DNA
<213> ORGANISM: Artificial sequence
<220> FEATURE:
<223> OTHER INFORMATION: Synthetic nucleic acid

<400> SEQUENCE: 18
gtctgcacac gagaaggcta gaagtcgact agcttactca tacggaacga gctagtaccc    60
gttcatacgt cgcgcaagta tctcggacta tcagcatgta gtacgagatc agtgacaggg   120
tataccagtt gagacgcaac tatggtgacg aa                             152

<210> SEQ ID NO 19
<211> LENGTH: 45
<212> TYPE: DNA
<213> ORGANISM: Artificial sequence
<220> FEATURE:
<223> OTHER INFORMATION: Synthetic nucleic acid
<220> FEATURE:
<221> NAME/KEY: misc_feature
<222> LOCATION: (16)..(20)
<223> OTHER INFORMATION: n is a, c, g, or t

<400> SEQUENCE: 19
tgcctcgatc atgggnnnnn aacaacaacc caagtatgca gcgcg               45

<210> SEQ ID NO 20
<211> LENGTH: 45
<212> TYPE: DNA
<213> ORGANISM: Artificial sequence
<220> FEATURE:
<223> OTHER INFORMATION: Synthetic nucleic acid
<220> FEATURE:
<221> NAME/KEY: misc_feature
<222> LOCATION: (16)..(20)
<223> OTHER INFORMATION: n is a, c, g, or t

<400> SEQUENCE: 20
tgcctcgatc atgggnnnnn aactctcgcc caagtatgca gcgcg               45

<210> SEQ ID NO 21
<211> LENGTH: 45
<212> TYPE: DNA
<213> ORGANISM: Artificial sequence
<220> FEATURE:
<223> OTHER INFORMATION: Synthetic nucleic acid
<220> FEATURE:
<221> NAME/KEY: misc_feature
<222> LOCATION: (16)..(20)
<223> OTHER INFORMATION: n is a, c, g, or t

<400> SEQUENCE: 21
tgcctcgatc atgggnnnnn acagttatgc caagtatgca gcgcg               45

<210> SEQ ID NO 22
<211> LENGTH: 45
<212> TYPE: DNA
<213> ORGANISM: Artificial sequence
<220> FEATURE:
<223> OTHER INFORMATION: Synthetic nucleic acid
<220> FEATURE:
<221> NAME/KEY: misc_feature
<222> LOCATION: (16)..(20)
<223> OTHER INFORMATION: n is a, c, g, or t

<400> SEQUENCE: 22
tgcctcgatc atgggnnnnn agctacgatg caagtatgca gcgcg               45

<210> SEQ ID NO 23
<211> LENGTH: 45
<212> TYPE: DNA
<213> ORGANISM: Artificial sequence
<220> FEATURE:
<223> OTHER INFORMATION: Synthetic nucleic acid
<220> FEATURE:
<221> NAME/KEY: misc_feature
<222> LOCATION: (16)..(20)
<223> OTHER INFORMATION: n is a, c, g, or t

<400> SEQUENCE: 23
tgcctcgatc atgggnnnnn ataagagcac caagtatgca gcgcg    45

<210> SEQ ID NO 24
<211> LENGTH: 45
<212> TYPE: DNA
<213> ORGANISM: Artificial sequence
<220> FEATURE:
<223> OTHER INFORMATION: Synthetic nucleic acid
<220> FEATURE:
<221> NAME/KEY: misc_feature
<222> LOCATION: (16)..(20)
<223> OTHER INFORMATION: n is a, c, g, or t

<400> SEQUENCE: 24
tgcctcgatc atgggnnnnn ccactcgaac caagtatgca gcgcg    45

<210> SEQ ID NO 25
<211> LENGTH: 44
<212> TYPE: DNA
<213> ORGANISM: Artificial sequence
<220> FEATURE:
<223> OTHER INFORMATION: Synthetic nucleic acid
<220> FEATURE:
<221> NAME/KEY: misc_feature
<222> LOCATION: (16)..(20)
<223> OTHER INFORMATION: n is a, c, g, or t

<400> SEQUENCE: 25
tgcctcgatc atgggnnnnn cgagaagaac aagtatgcag cgcg    44

<210> SEQ ID NO 26
<211> LENGTH: 45
<212> TYPE: DNA
<213> ORGANISM: Artificial sequence
<220> FEATURE:
<223> OTHER INFORMATION: Synthetic nucleic acid
<220> FEATURE:
<221> NAME/KEY: misc_feature
<222> LOCATION: (16)..(20)
<223> OTHER INFORMATION: n is a, c, g, or t

<400> SEQUENCE: 26
tgcctcgatc atgggnnnnn ctctatacac caagtatgca gcgcg    45

<210> SEQ ID NO 27
<211> LENGTH: 45
<212> TYPE: DNA
<213> ORGANISM: Artificial sequence
<220> FEATURE:
<223> OTHER INFORMATION: Synthetic nucleic acid
<220> FEATURE:
<221> NAME/KEY: misc_feature
<222> LOCATION: (16)..(20)
<223> OTHER INFORMATION: n is a, c, g, or t

<400> SEQUENCE: 27
tgcctcgatc atgggnnnnn gtagaatcct caagtatgca gcgcg    45

<210> SEQ ID NO 28
<211> LENGTH: 45
<212> TYPE: DNA
<213> ORGANISM: Artificial sequence
<220> FEATURE:
<223> OTHER INFORMATION: Synthetic nucleic acid
<220> FEATURE:
<221> NAME/KEY: misc_feature
<222> LOCATION: (16)..(20)
<223> OTHER INFORMATION: n is a, c, g, or t

<400> SEQUENCE: 28
tgcctcgatc atgggnnnnn tccttaatcc caagtatgca gcgcg            45

<210> SEQ ID NO 29
<211> LENGTH: 45
<212> TYPE: DNA
<213> ORGANISM: Artificial sequence
<220> FEATURE:
<223> OTHER INFORMATION: Synthetic nucleic acid
<220> FEATURE:
<221> NAME/KEY: misc_feature
<222> LOCATION: (16)..(20)
<223> OTHER INFORMATION: n is a, c, g, or t

<400> SEQUENCE: 29
ttcatagagc ctgatnnnnn aacaaggtgg agtcgtacat catgc            45

<210> SEQ ID NO 30
<211> LENGTH: 45
<212> TYPE: DNA
<213> ORGANISM: Artificial sequence
<220> FEATURE:
<223> OTHER INFORMATION: Synthetic nucleic acid
<220> FEATURE:
<221> NAME/KEY: misc_feature
<222> LOCATION: (16)..(20)
<223> OTHER INFORMATION: n is a, c, g, or t

<400> SEQUENCE: 30
ttcatagagc ctgatnnnnn aagactgaga agtcgtacat catgc            45

<210> SEQ ID NO 31
<211> LENGTH: 45
<212> TYPE: DNA
<213> ORGANISM: Artificial sequence
<220> FEATURE:
<223> OTHER INFORMATION: Synthetic nucleic acid
<220> FEATURE:
<221> NAME/KEY: misc_feature
<222> LOCATION: (16)..(20)
<223> OTHER INFORMATION: n is a, c, g, or t

<400> SEQUENCE: 31
ttcatagagc ctgatnnnnn accgcaagac agtcgtacat catgc            45

<210> SEQ ID NO 32
<211> LENGTH: 45
<212> TYPE: DNA
<213> ORGANISM: Artificial sequence
<220> FEATURE:
<223> OTHER INFORMATION: Synthetic nucleic acid
<220> FEATURE:
<221> NAME/KEY: misc_feature
<222> LOCATION: (16)..(20)
<223> OTHER INFORMATION: n is a, c, g, or t

<400> SEQUENCE: 32
ttcatagagc ctgatnnnnn aggaattgcc agtcgtacat catgc            45

<210> SEQ ID NO 33
<211> LENGTH: 45
<212> TYPE: DNA
<213> ORGANISM: Artificial sequence
<220> FEATURE:
<223> OTHER INFORMATION: Synthetic nucleic acid
<220> FEATURE:
<221> NAME/KEY: misc_feature
<222> LOCATION: (16)..(20)
<223> OTHER INFORMATION: n is a, c, g, or t

<400> SEQUENCE: 33
ttcatagagc ctgatnnnnn atcttggagt agtcgtacat catgc                45

<210> SEQ ID NO 34
<211> LENGTH: 45
<212> TYPE: DNA
<213> ORGANISM: Artificial sequence
<220> FEATURE:
<223> OTHER INFORMATION: Synthetic nucleic acid
<220> FEATURE:
<221> NAME/KEY: misc_feature
<222> LOCATION: (16)..(20)
<223> OTHER INFORMATION: n is a, c, g, or t

<400> SEQUENCE: 34
ttcatagagc ctgatnnnnn ccggtagttc agtcgtacat catgc                45

<210> SEQ ID NO 35
<211> LENGTH: 45
<212> TYPE: DNA
<213> ORGANISM: Artificial sequence
<220> FEATURE:
<223> OTHER INFORMATION: Synthetic nucleic acid
<220> FEATURE:
<221> NAME/KEY: misc_feature
<222> LOCATION: (16)..(20)
<223> OTHER INFORMATION: n is a, c, g, or t

<400> SEQUENCE: 35
ttcatagagc ctgatnnnnn cggacaccta agtcgtacat catgc                45

<210> SEQ ID NO 36
<211> LENGTH: 45
<212> TYPE: DNA
<213> ORGANISM: Artificial sequence
<220> FEATURE:
<223> OTHER INFORMATION: Synthetic nucleic acid
<220> FEATURE:
<221> NAME/KEY: misc_feature
<222> LOCATION: (16)..(20)
<223> OTHER INFORMATION: n is a, c, g, or t

<400> SEQUENCE: 36
ttcatagagc ctgatnnnnn gaggttcagc agtcgtacat catgc                45

<210> SEQ ID NO 37
<211> LENGTH: 45
<212> TYPE: DNA
<213> ORGANISM: Artificial sequence
<220> FEATURE:
<223> OTHER INFORMATION: Synthetic nucleic acid
<220> FEATURE:
<221> NAME/KEY: misc_feature
<222> LOCATION: (16)..(20)
<223> OTHER INFORMATION: n is a, c, g, or t

<400> SEQUENCE: 37
ttcatagagc ctgatnnnnn gtccacagct agtcgtacat catgc                45

<210> SEQ ID NO 38
<211> LENGTH: 45
<212> TYPE: DNA
<213> ORGANISM: Artificial sequence
<220> FEATURE:
<223> OTHER INFORMATION: Synthetic nucleic acid
<220> FEATURE:
<221> NAME/KEY: misc_feature
<222> LOCATION: (16)..(20)

<223> OTHER INFORMATION: n is a, c, g, or t

<400> SEQUENCE: 38
ttcatagagc ctgatnnnnn tggtgcataa agtcgtacat catgc          45

<210> SEQ ID NO 39
<211> LENGTH: 48
<212> TYPE: DNA
<213> ORGANISM: Artificial sequence
<220> FEATURE:
<223> OTHER INFORMATION: Synthetic nucleic acid

<400> SEQUENCE: 39
tctagtcact gtcacaaccg attccactct gcgttgatac cactgctt          48

<210> SEQ ID NO 40
<211> LENGTH: 48
<212> TYPE: DNA
<213> ORGANISM: Artificial sequence
<220> FEATURE:
<223> OTHER INFORMATION: Synthetic nucleic acid

<400> SEQUENCE: 40
tctagtcact gtcacaatgg taacgactct gcgttgatac cactgctt          48

<210> SEQ ID NO 41
<211> LENGTH: 48
<212> TYPE: DNA
<213> ORGANISM: Artificial sequence
<220> FEATURE:
<223> OTHER INFORMATION: Synthetic nucleic acid

<400> SEQUENCE: 41
tctagtcact gtcacacgcc tcttaactct gcgttgatac cactgctt          48

<210> SEQ ID NO 42
<211> LENGTH: 48
<212> TYPE: DNA
<213> ORGANISM: Artificial sequence
<220> FEATURE:
<223> OTHER INFORMATION: Synthetic nucleic acid

<400> SEQUENCE: 42
tctagtcact gtcacagtgt ggtccactct gcgttgatac cactgctt          48

<210> SEQ ID NO 43
<211> LENGTH: 48
<212> TYPE: DNA
<213> ORGANISM: Artificial sequence
<220> FEATURE:
<223> OTHER INFORMATION: Synthetic nucleic acid

<400> SEQUENCE: 43
tctagtcact gtcaccaata cgtccactct gcgttgatac cactgctt          48

<210> SEQ ID NO 44
<211> LENGTH: 48
<212> TYPE: DNA
<213> ORGANISM: Artificial sequence
<220> FEATURE:
<223> OTHER INFORMATION: Synthetic nucleic acid

<400> SEQUENCE: 44
tctagtcact gtcaccctca ttgtcactct gcgttgatac cactgctt          48

```
<210> SEQ ID NO 45
<211> LENGTH: 48
<212> TYPE: DNA
<213> ORGANISM: Artificial sequence
<220> FEATURE:
<223> OTHER INFORMATION: Synthetic nucleic acid

<400> SEQUENCE: 45
tctagtcact gtcacctagc gcgttactct gcgttgatac cactgctt           48

<210> SEQ ID NO 46
<211> LENGTH: 48
<212> TYPE: DNA
<213> ORGANISM: Artificial sequence
<220> FEATURE:
<223> OTHER INFORMATION: Synthetic nucleic acid

<400> SEQUENCE: 46
tctagtcact gtcacgcgtc gtgaaactct gcgttgatac cactgctt           48

<210> SEQ ID NO 47
<211> LENGTH: 48
<212> TYPE: DNA
<213> ORGANISM: Artificial sequence
<220> FEATURE:
<223> OTHER INFORMATION: Synthetic nucleic acid

<400> SEQUENCE: 47
tctagtcact gtcaccttac tcggtactct gcgttgatac cactgctt           48

<210> SEQ ID NO 48
<211> LENGTH: 48
<212> TYPE: DNA
<213> ORGANISM: Artificial sequence
<220> FEATURE:
<223> OTHER INFORMATION: Synthetic nucleic acid

<400> SEQUENCE: 48
tctagtcact gtcacttcga tgcggactct gcgttgatac cactgctt           48

<210> SEQ ID NO 49
<211> LENGTH: 8
<212> TYPE: PRT
<213> ORGANISM: Artificial sequence
<220> FEATURE:
<223> OTHER INFORMATION: Synthetic peptide

<400> SEQUENCE: 49

Arg Thr Arg Phe Thr Gly Arg Tyr
1               5

<210> SEQ ID NO 50
<211> LENGTH: 13
<212> TYPE: PRT
<213> ORGANISM: Artificial sequence
<220> FEATURE:
<223> OTHER INFORMATION: Synthetic peptide

<400> SEQUENCE: 50

Phe Val Asn Gln His Leu Cys Gly Ser His Leu Val Asp
1               5                   10

<210> SEQ ID NO 51
<211> LENGTH: 7
<212> TYPE: PRT
<213> ORGANISM: Artificial sequence
<220> FEATURE:
```

<223> OTHER INFORMATION: Synthetic peptide

<400> SEQUENCE: 51

Lys Cys Asp Tyr Trp Glu Cys
1               5

<210> SEQ ID NO 52
<211> LENGTH: 144
<212> TYPE: DNA
<213> ORGANISM: Artificial sequence
<220> FEATURE:
<223> OTHER INFORMATION: Synthetic nucleic acid

<400> SEQUENCE: 52
cagacgtgtg ctcttccgat cttcagctga tcgaatgagt atgccttgcc tcgatcatgg      60
gcaagtatgc agcgcgttca tagagcctga tagtcgtaca tcatgctcta gtcactgtca     120
cactctgcgt tgataccact gctt                                            144

<210> SEQ ID NO 53
<211> LENGTH: 164
<212> TYPE: DNA
<213> ORGANISM: Artificial sequence
<220> FEATURE:
<223> OTHER INFORMATION: Synthetic nucleic acid
<220> FEATURE:
<221> NAME/KEY: misc_feature
<222> LOCATION: (1)..(14)
<223> OTHER INFORMATION: n is a, c, g, or t
<220> FEATURE:
<221> NAME/KEY: misc_feature
<222> LOCATION: (16)..(20)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (40)..(43)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (48)..(50)
<223> OTHER INFORMATION: n is a, c, g, or t
<220> FEATURE:
<221> NAME/KEY: misc_feature
<222> LOCATION: (82)..(82)
<223> OTHER INFORMATION: n is a, c, g, or t
<220> FEATURE:
<221> NAME/KEY: misc_feature
<222> LOCATION: (85)..(85)
<223> OTHER INFORMATION: n is a, c, g, or t
<220> FEATURE:
<221> NAME/KEY: misc_feature
<222> LOCATION: (88)..(88)
<223> OTHER INFORMATION: n is a, c, g, or t
<220> FEATURE:
<221> NAME/KEY: misc_feature
<222> LOCATION: (91)..(91)
<223> OTHER INFORMATION: n is a, c, g, or t
<220> FEATURE:
<221> NAME/KEY: misc_feature
<222> LOCATION: (93)..(93)
<223> OTHER INFORMATION: n is a, c, g, or t
<220> FEATURE:
<221> NAME/KEY: misc_feature
<222> LOCATION: (95)..(96)
<223> OTHER INFORMATION: n is a, c, g, or t
<220> FEATURE:

```
<221> NAME/KEY: misc_feature
<222> LOCATION: (128)..(136)
<223> OTHER INFORMATION: n is a, c, g, or t
<220> FEATURE:
<221> NAME/KEY: misc_feature
<222> LOCATION: (156)..(157)
<223> OTHER INFORMATION: n is a, c, g, or t
<220> FEATURE:
<221> NAME/KEY: misc_feature
<222> LOCATION: (160)..(162)
<223> OTHER INFORMATION: n is a, c, g, or t
<220> FEATURE:
<221> NAME/KEY: misc_feature
<222> LOCATION: (164)..(164)
<223> OTHER INFORMATION: n is a, c, g, or t

<400> SEQUENCE: 53
nnnnnnnnnn nnnnannnnn cttgcctcgn tcatgggtgn nnnanaannn ccaagtatgc      60
agcgcgttca tagagcctga tnggnganga nangnnagtc gtacatcatg ctctagtcac     120
tgtcaccnnn nnnnnnactc tgcgttgata ccactnnttn nnan                     164

<210> SEQ ID NO 54
<211> LENGTH: 152
<212> TYPE: DNA
<213> ORGANISM: Artificial sequence
<220> FEATURE:
<223> OTHER INFORMATION: Synthetic nucleic acid

<400> SEQUENCE: 54
aagcagtggt atcaacgcag agtgtgacag tgactagagc atgatgtacg actatcaggc     60
tctatgaacg cgctgcatac ttgcccatga tcgaggcaag gcatactcat tcgatcagct    120
gaagatcgga agatcggaag agcacacgtc tg                                  152

<210> SEQ ID NO 55
<211> LENGTH: 158
<212> TYPE: DNA
<213> ORGANISM: Artificial sequence
<220> FEATURE:
<223> OTHER INFORMATION: Synthetic nucleic acid
<220> FEATURE:
<221> NAME/KEY: misc_feature
<222> LOCATION: (1)..(14)
<223> OTHER INFORMATION: n is a, c, g, or t
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (42)..(43)
<223> OTHER INFORMATION: n is a, c, g, or t
<220> FEATURE:
<221> NAME/KEY: misc_feature
<222> LOCATION: (45)..(48)
<223> OTHER INFORMATION: n is a, c, g, or t
<220> FEATURE:
<221> NAME/KEY: misc_feature
<222> LOCATION: (50)..(52)
<223> OTHER INFORMATION: n is a, c, g, or t
<220> FEATURE:
<221> NAME/KEY: misc_feature
<222> LOCATION: (84)..(88)
<223> OTHER INFORMATION: n is a, c, g, or t
```

```
<220> FEATURE:
<221> NAME/KEY: misc_feature
<222> LOCATION: (92)..(92)
<223> OTHER INFORMATION: n is a, c, g, or t
<220> FEATURE:
<221> NAME/KEY: misc_feature
<222> LOCATION: (95)..(97)
<223> OTHER INFORMATION: n is a, c, g, or t
<220> FEATURE:
<221> NAME/KEY: misc_feature
<222> LOCATION: (158)..(158)
<223> OTHER INFORMATION: n is a, c, g, or t

<400> SEQUENCE: 55
nnnnnnnnnn nnnngnntag agcntgatgt acgactgnng tnncnnnncn nnatcaggct      60
ctatgaacgc gctgcatact tggnnnnnct gnccnnnccc atgatcgagg caaggcatac     120
tcattcgatc agctgaagat cggaagagca cacgctgn                             158

<210> SEQ ID NO 56
<211> LENGTH: 250
<212> TYPE: DNA
<213> ORGANISM: Artificial sequence
<220> FEATURE:
<223> OTHER INFORMATION: Synthetic nucleic acid

<400> SEQUENCE: 56
cagacgtgtg ctcttccgat cttcagctga tcgaatgagt atgccttgcc tcgatcatgg      60
gcctgcagct accatgcagt atgcagcgcg ttcatagagc ctgatgctgt gtccacagct     120
agtcgtacat catgctctag tcactgtcac aatggtaacg actctgcgtt gataccactg     180
cttagatcgg aagagcacac gtctgaactc cagtcaccca acattatctc gtatgccgtc     240
ttctgcttga                                                            250

<210> SEQ ID NO 57
<211> LENGTH: 138
<212> TYPE: DNA
<213> ORGANISM: Artificial sequence
<220> FEATURE:
<223> OTHER INFORMATION: Synthetic nucleic acid
<220> FEATURE:
<221> NAME/KEY: misc_feature
<222> LOCATION: (16)..(20)
<223> OTHER INFORMATION: n is a, c, g, or t
<220> FEATURE:
<221> NAME/KEY: misc_feature
<222> LOCATION: (61)..(65)
<223> OTHER INFORMATION: n is a, c, g, or t

<400> SEQUENCE: 57
tgcctcgatc atgggnnnnn agctaccatg caagtatgca gcgcgttcat agagcctgat      60
nnnnngtcca cagctagtcg tacatcatgc tctagtcact gtcacaatgg taacgactct     120
gcgttgatac cactgctt                                                   138

<210> SEQ ID NO 58
<211> LENGTH: 250
<212> TYPE: DNA
<213> ORGANISM: Artificial sequence
<220> FEATURE:
<223> OTHER INFORMATION: Synthetic nucleic acid

<400> SEQUENCE: 58
caagcagaag acggcatacg agataatgtt gggtgactgg agttcagacg tgtgctcttc      60
cgatctcaga cgtgtgctct tccgatcttc agctgatcga atgagtatgc cttgcctcga    120
```

```
tcatgggtga agagagacgg agcaagtatg cagcgcgttc atagagcctg atgctgtgtc      180
ccccgcaagt cgtacatcat gctctagtca ctgtcacaat ggtaacgact ctgcgttgat      240
accactgctt                                                             250

<210> SEQ ID NO 59
<211> LENGTH: 138
<212> TYPE: DNA
<213> ORGANISM: Artificial sequence
<220> FEATURE:
<223> OTHER INFORMATION: Synthetic nucleic acid
<220> FEATURE:
<221> NAME/KEY: misc_feature
<222> LOCATION: (16)..(20)
<223> OTHER INFORMATION: n is a, c, g, or t
<220> FEATURE:
<221> NAME/KEY: misc_feature
<222> LOCATION: (61)..(65)
<223> OTHER INFORMATION: n is a, c, g, or t

<400> SEQUENCE: 59
tgcctcgatc atgggnnnnn agctaccatg caagtatgca gcgcgttcat agagcctgat      60
nnnnngtcca cagctagtcg tacatcatgc tctagtcact gtcacaatgg taacgactct      120
gcgttgatac cactgctt                                                    138
```